United States Patent
Schenker et al.

(10) Patent No.: US 10,350,358 B2
(45) Date of Patent: Jul. 16, 2019

(54) INJECTION DEVICE HAVING A DOSE INDICATING ELEMENT THAT CAN BE MOVED RELATIVE TO A HOUSING

(71) Applicant: TecPharma Licensing AG, Burgdorf (CH)

(72) Inventors: Susanne Schenker, Langenthal (CH); Ursina Streit, Schonbuhl (CH)

(73) Assignee: TecPharma Licensing AG, Burgdorf (CH)

( * ) Notice: Subject to any disclaimer, the term of this patent is extended or adjusted under 35 U.S.C. 154(b) by 91 days.

(21) Appl. No.: 14/502,317

(22) Filed: Sep. 30, 2014

(65) Prior Publication Data

US 2015/0018776 A1    Jan. 15, 2015

Related U.S. Application Data

(63) Continuation of application No. PCT/EP2013/056093, filed on Mar. 22, 2013.

(30) Foreign Application Priority Data

Mar. 30, 2012    (EP) ..................................... 12162777

(51) Int. Cl.
   *A61M 5/31*    (2006.01)
   *A61M 5/315*    (2006.01)
   (Continued)

(52) U.S. Cl.
   CPC .......... *A61M 5/31528* (2013.01); *A61M 5/20* (2013.01); *A61M 5/2033* (2013.01);
   (Continued)

(58) Field of Classification Search
   CPC .. A61M 5/31528; A61M 5/2033; A61M 5/20; A61M 5/31563; A61M 5/31553;
   (Continued)

(56) References Cited

U.S. PATENT DOCUMENTS

| 5,104,380 A | 4/1992 | Holman et al. |
| 2006/0153693 A1* | 7/2006 | Fiechter ............ A61M 5/31553 |
| | | 417/63 |

(Continued)

FOREIGN PATENT DOCUMENTS

| WO | WO 2001/019434 | 3/2001 |
| WO | 2006045528 A1 | 5/2006 |

(Continued)

OTHER PUBLICATIONS

Merriam Webster Dictionary definition for "along", definition 1, available online Jan. 30, 2017 at https://www.merriam-webster.com/dictionary/along.*

(Continued)

*Primary Examiner* — Amber R Stiles
(74) *Attorney, Agent, or Firm* — Dorsey & Whitney LLP

(57) ABSTRACT

A driving and dosing device for an injection device configured for dose setting and dose administration includes: a housing, a dose indicating element including a circumferential dose scale, a pointing device and a dosing element gripped by a user. In order to set the dose to be administered, the dosing element is rotatable such that the dose indicating element is rotatable or screwable about an axis of rotation relative to the pointing device, and a value of the dose scale that corresponds to the set dose is readable by means of the pointing device. A bearing element, with which the dose indicating element is in an engagement, causes the rotational or screwing motion of the dose indicating element relative to the pointing device, characterized in that the bearing element can be moved together with the dose indicating element relative to the housing and along the axis of rotation.

26 Claims, 30 Drawing Sheets

(51) Int. Cl.
*A61M 5/20* (2006.01)
*A61M 5/24* (2006.01)

(52) U.S. Cl.
CPC .... *A61M 5/31553* (2013.01); *A61M 5/31563* (2013.01); *A61M 5/3157* (2013.01); *A61M 5/31541* (2013.01); *A61M 5/31583* (2013.01); *A61M 2005/2407* (2013.01); *A61M 2005/3126* (2013.01); *A61M 2205/581* (2013.01); *A61M 2205/582* (2013.01)

(58) Field of Classification Search
CPC ........ A61M 5/31541; A61M 2205/582; A61M 2005/3126; A61M 5/3157; A61M 5/31583; A61M 2005/2407; A61M 2205/581
See application file for complete search history.

(56) References Cited

U.S. PATENT DOCUMENTS

| | | | |
|---|---|---|---|
| 2006/0206057 A1* | 9/2006 | DeRuntz | A61M 5/31551 604/224 |
| 2006/0276753 A1 | 12/2006 | Kronestedt | |
| 2008/0306445 A1 | 12/2008 | Burren | |
| 2009/0012479 A1 | 1/2009 | Moller | |
| 2009/0054839 A1 | 2/2009 | Moller | |
| 2010/0168677 A1* | 7/2010 | Gabriel | A61M 5/31551 604/189 |
| 2010/0268171 A1* | 10/2010 | Moller | A61M 5/31551 604/246 |
| 2010/0274198 A1* | 10/2010 | Bechtold | A61M 5/31551 604/189 |
| 2010/0324493 A1* | 12/2010 | Plumptre | A61M 5/31541 604/207 |
| 2012/0010575 A1* | 1/2012 | Jones | A61M 5/31555 604/211 |
| 2016/0184530 A1 | 6/2016 | Schenker | |

FOREIGN PATENT DOCUMENTS

| | | |
|---|---|---|
| WO | WO 2006/077466 | 7/2006 |
| WO | WO 2008/031237 | 3/2008 |
| WO | WO 2008/087071 | 7/2008 |
| WO | WO 2010/081489 | 7/2010 |
| WO | WO 2010/115670 | 10/2010 |
| WO | WO 2010/149209 | 12/2010 |
| WO | 2011045611 A2 | 4/2011 |
| WO | WO 2012/037938 | 3/2012 |
| WO | 2012067582 A1 | 5/2012 |

OTHER PUBLICATIONS

"European Search Report", from European Application No. 12162777.2, dated Jan. 11, 2013, 6 pages.
"International Preliminary Report on Patentability", from PCT/EP2013/056093, dated Oct. 1, 2014, 6 pages (English translation included).

* cited by examiner

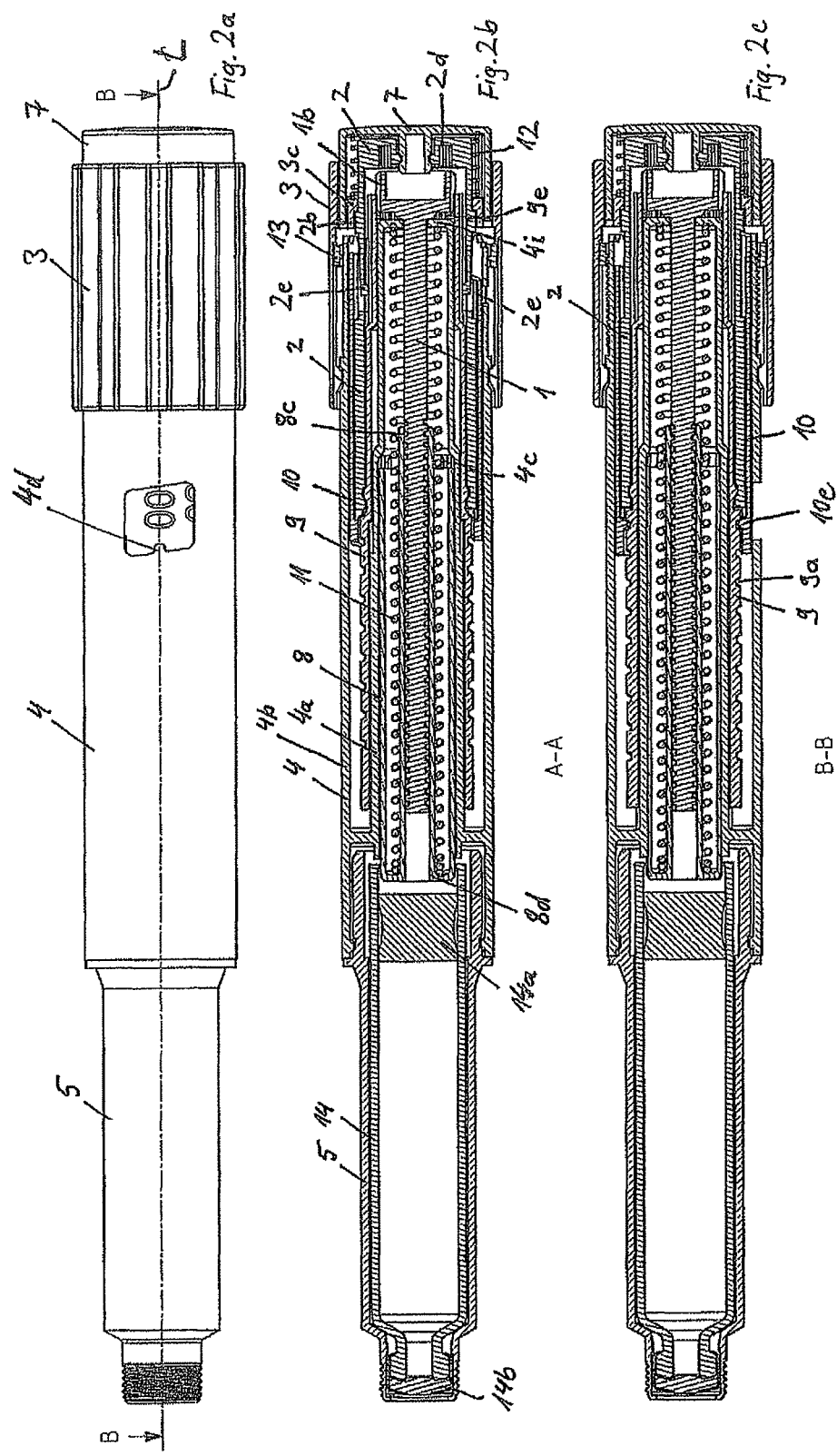

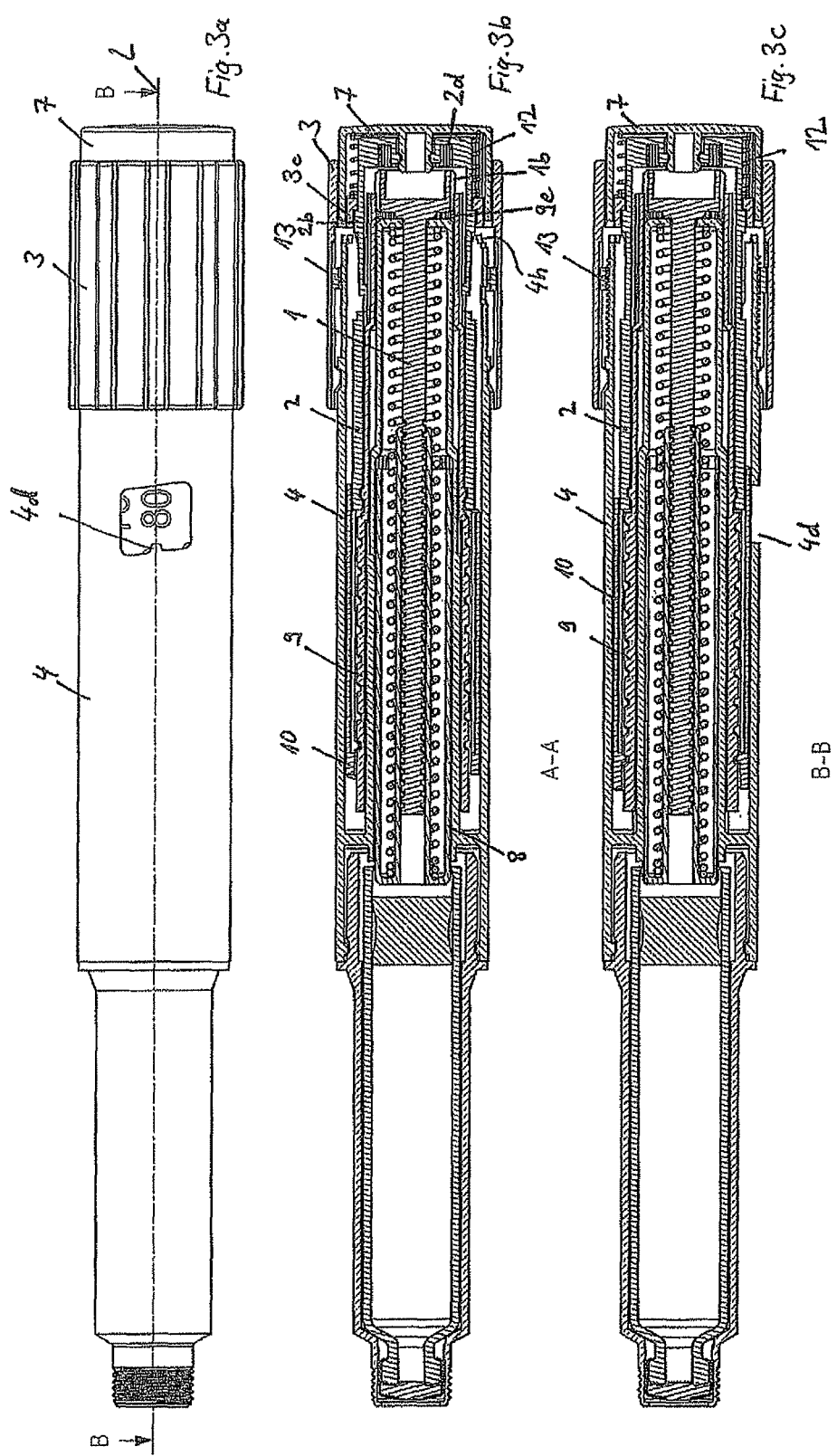

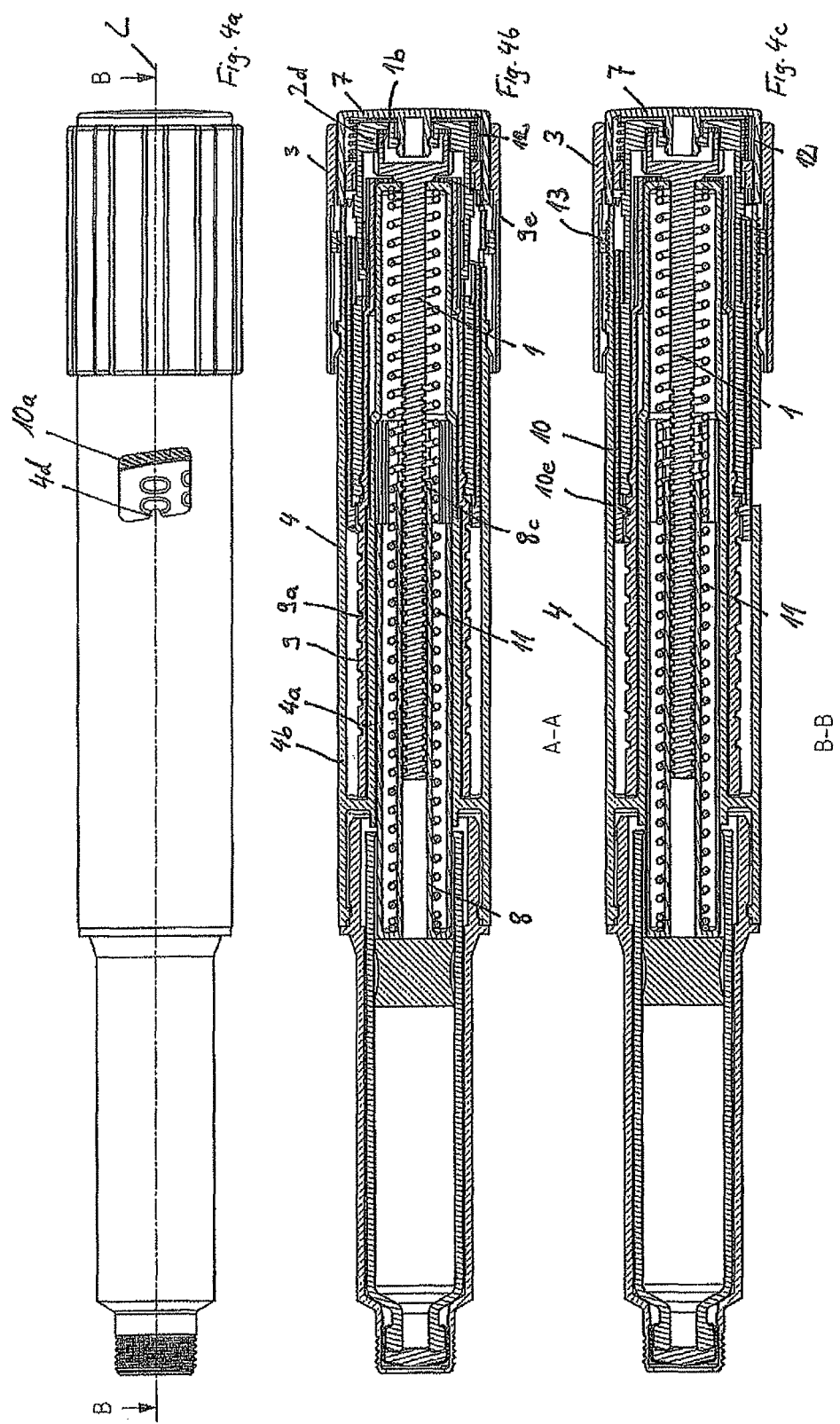

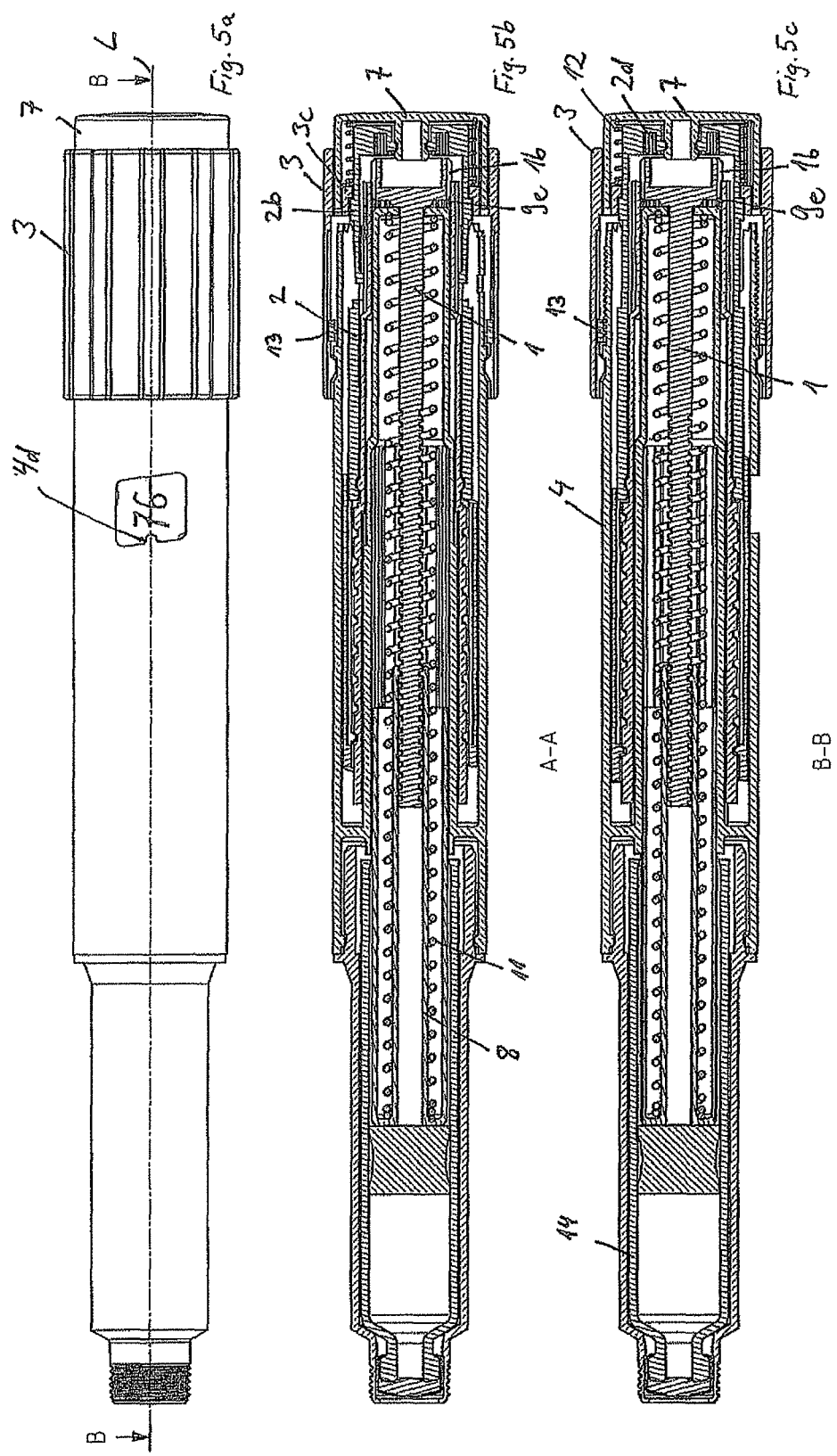

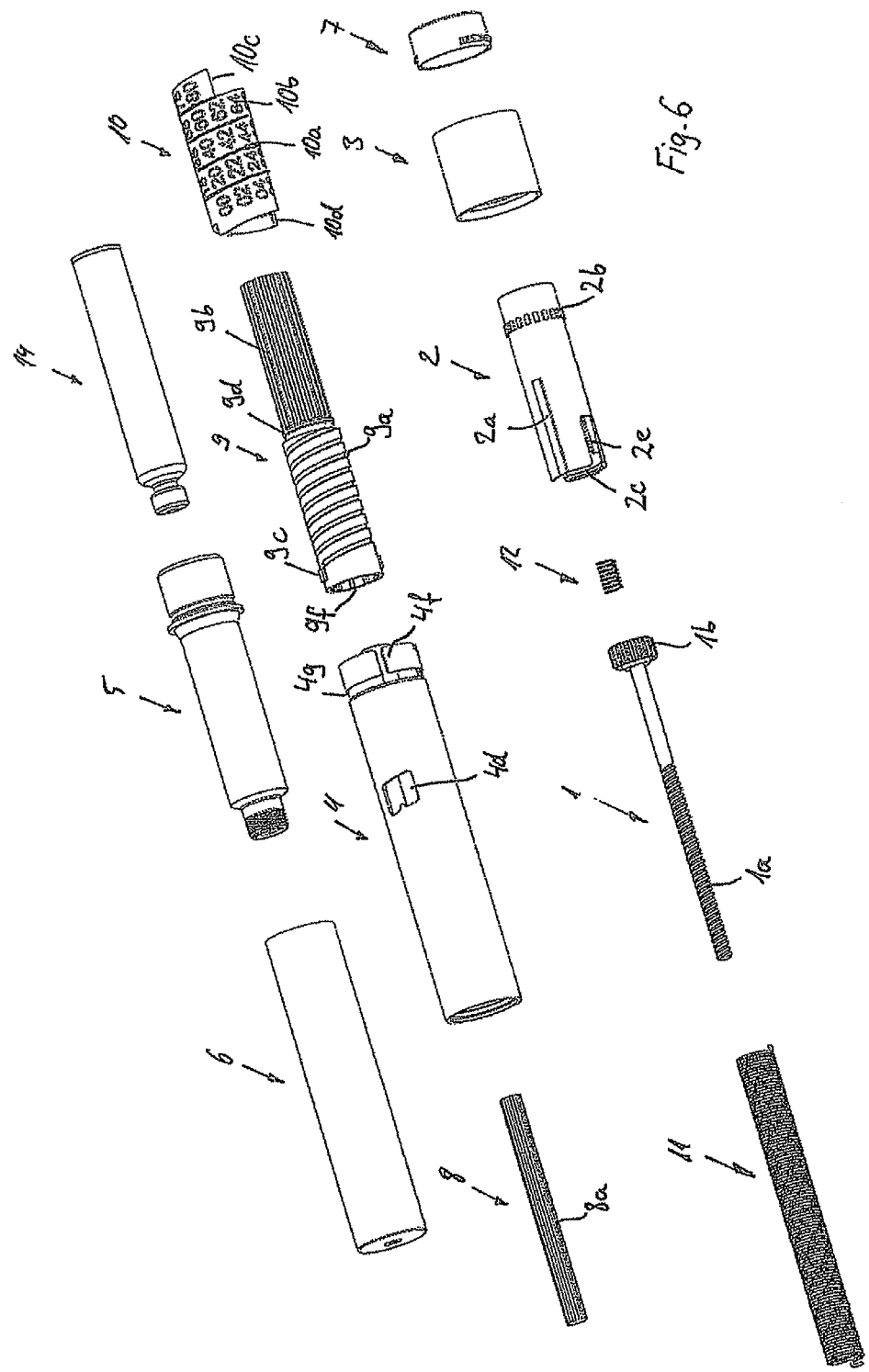

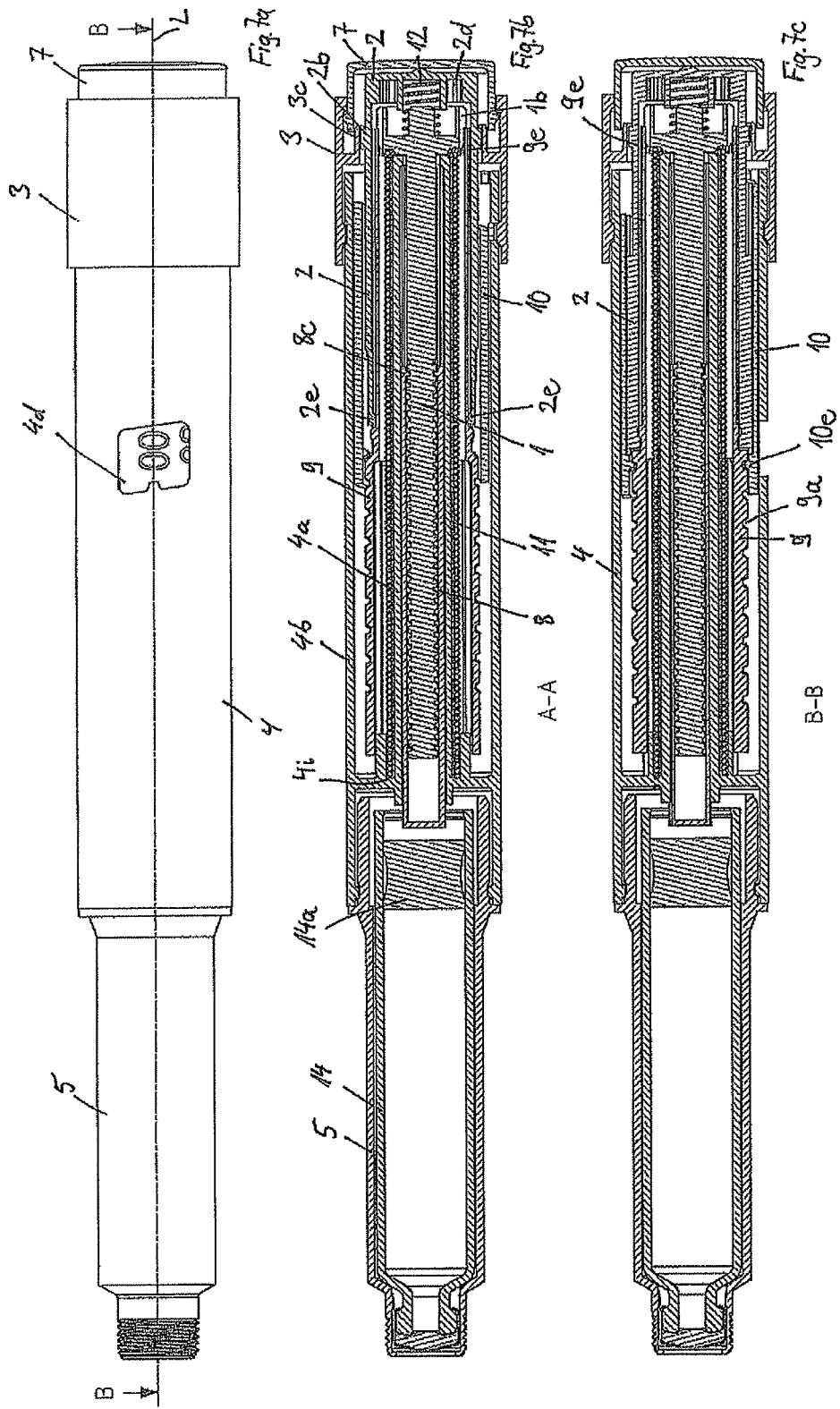

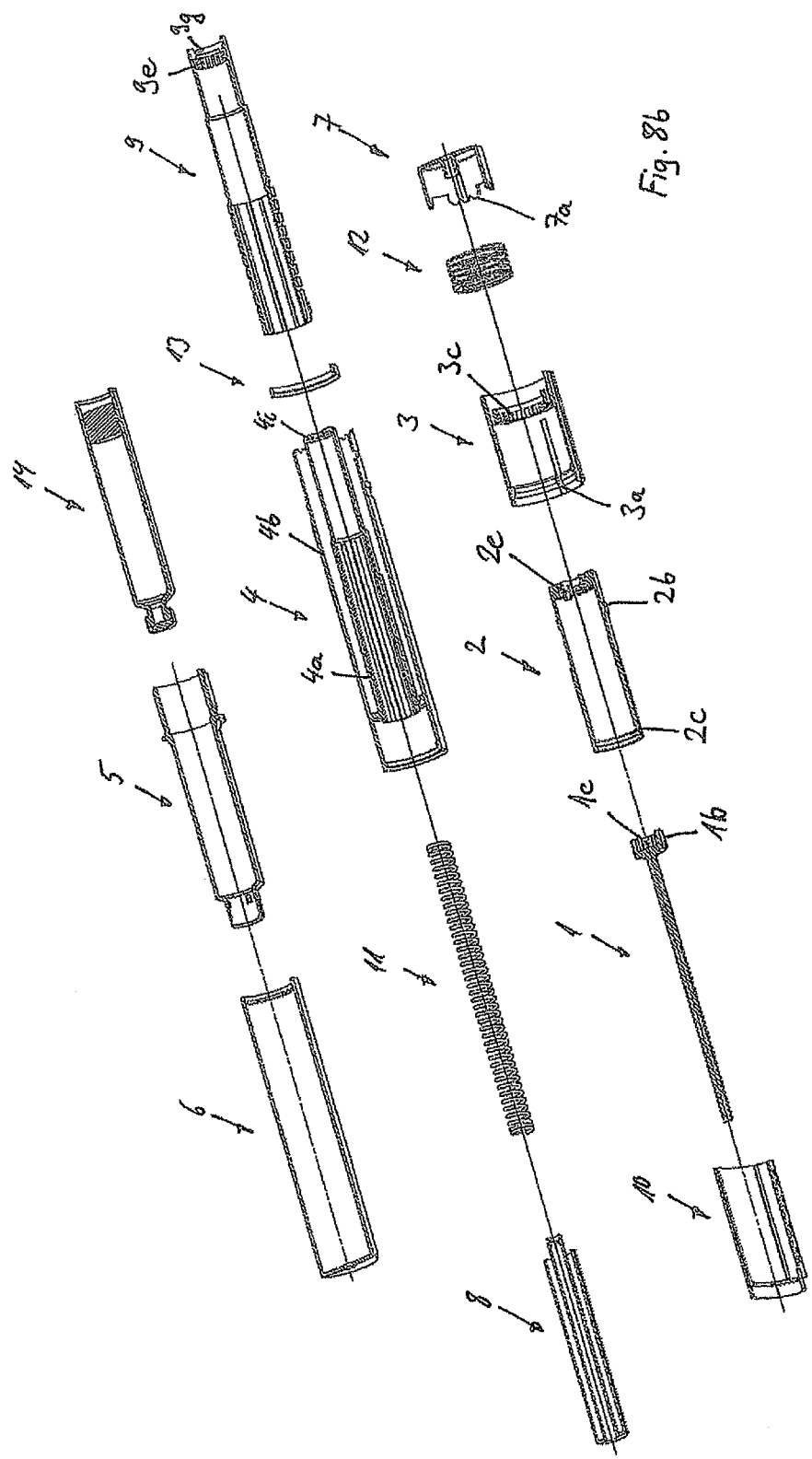

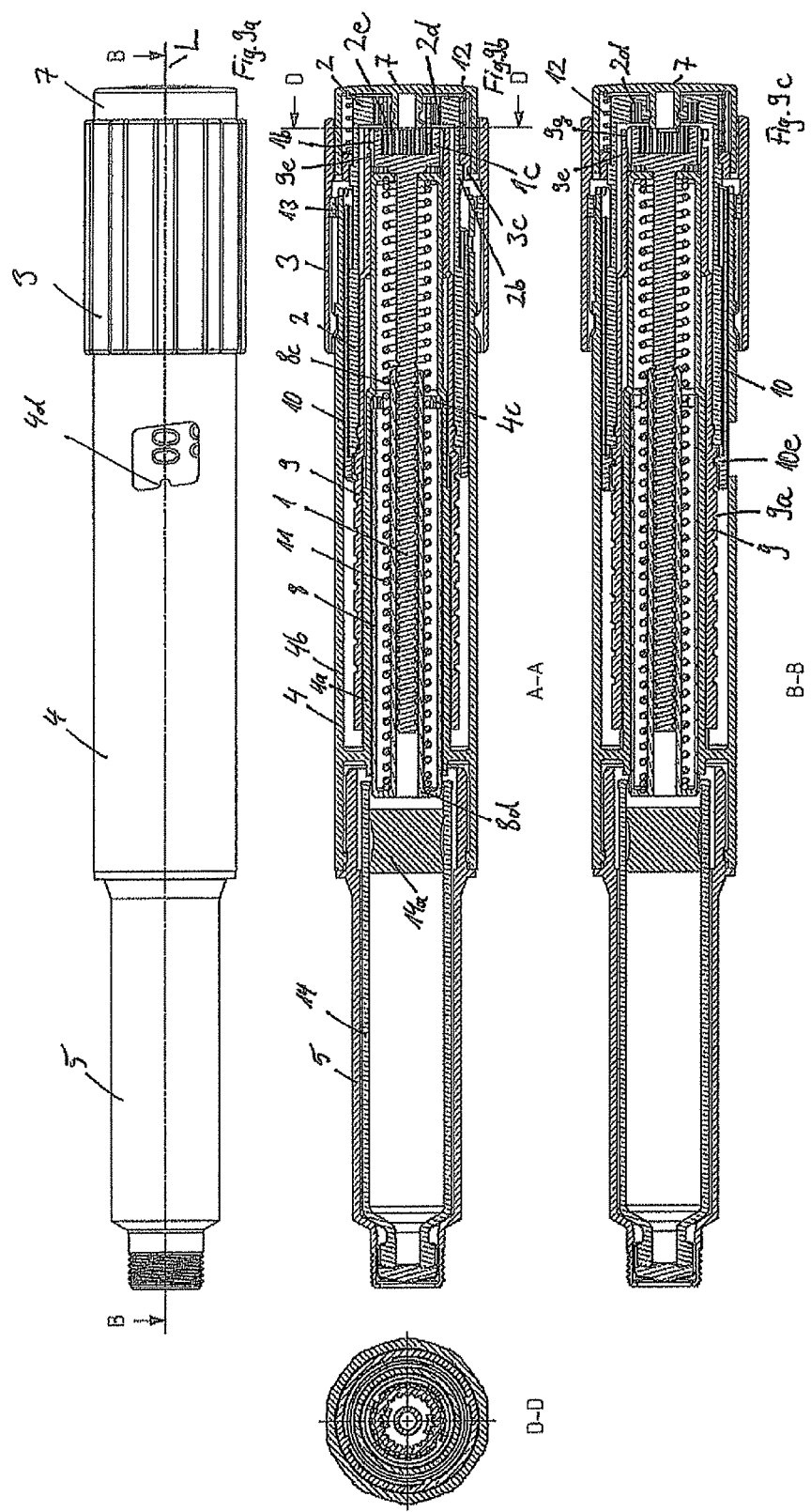

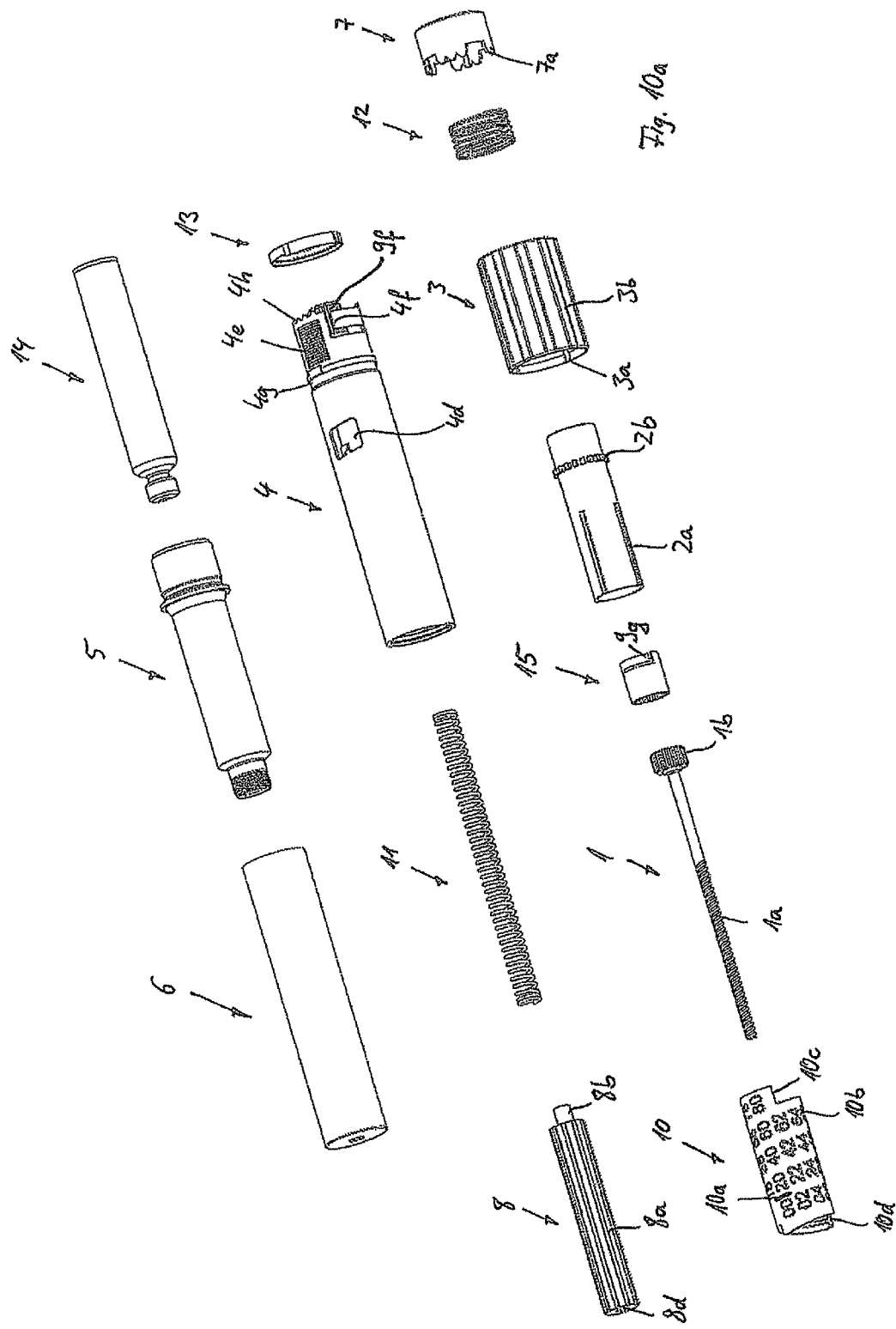

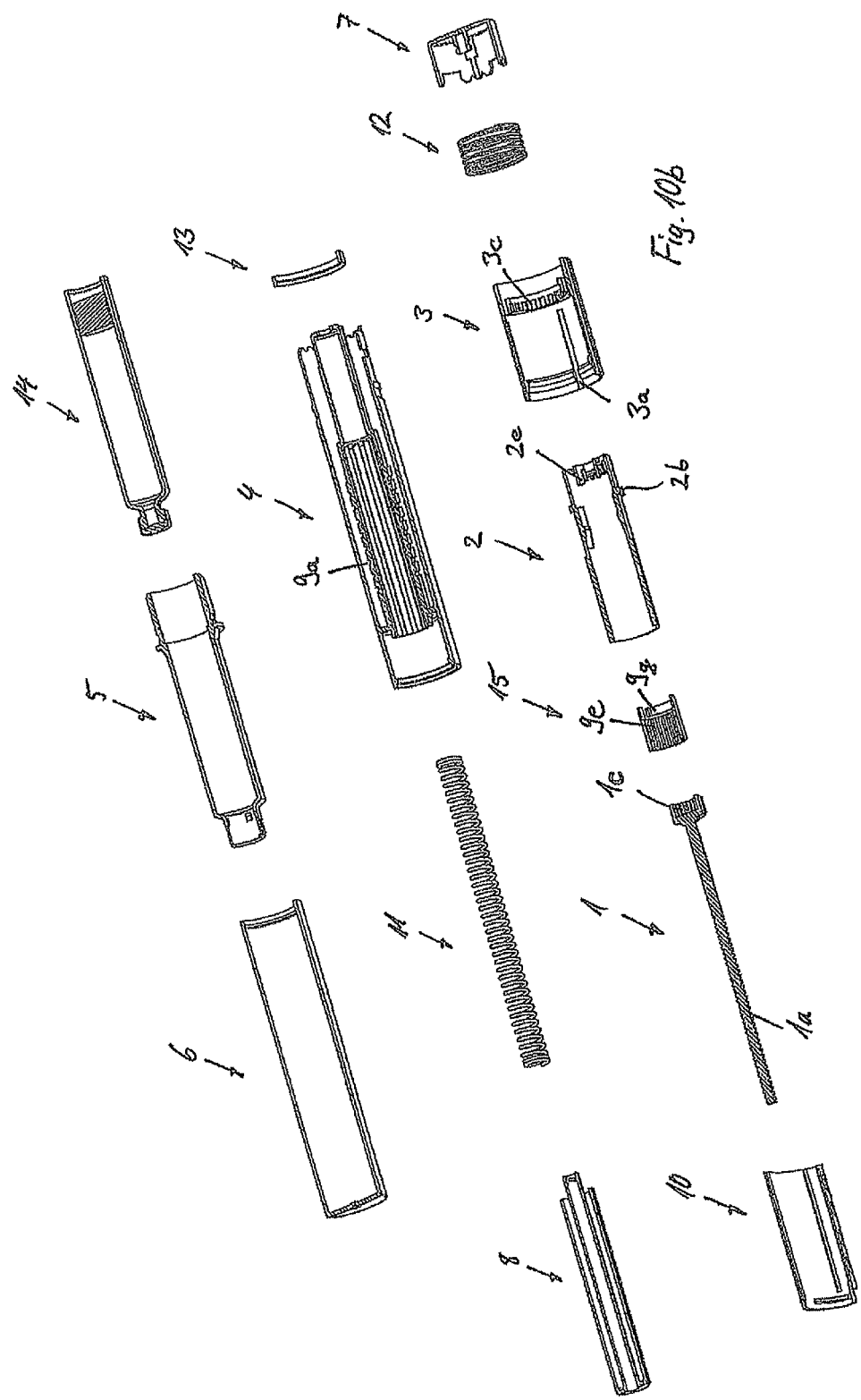

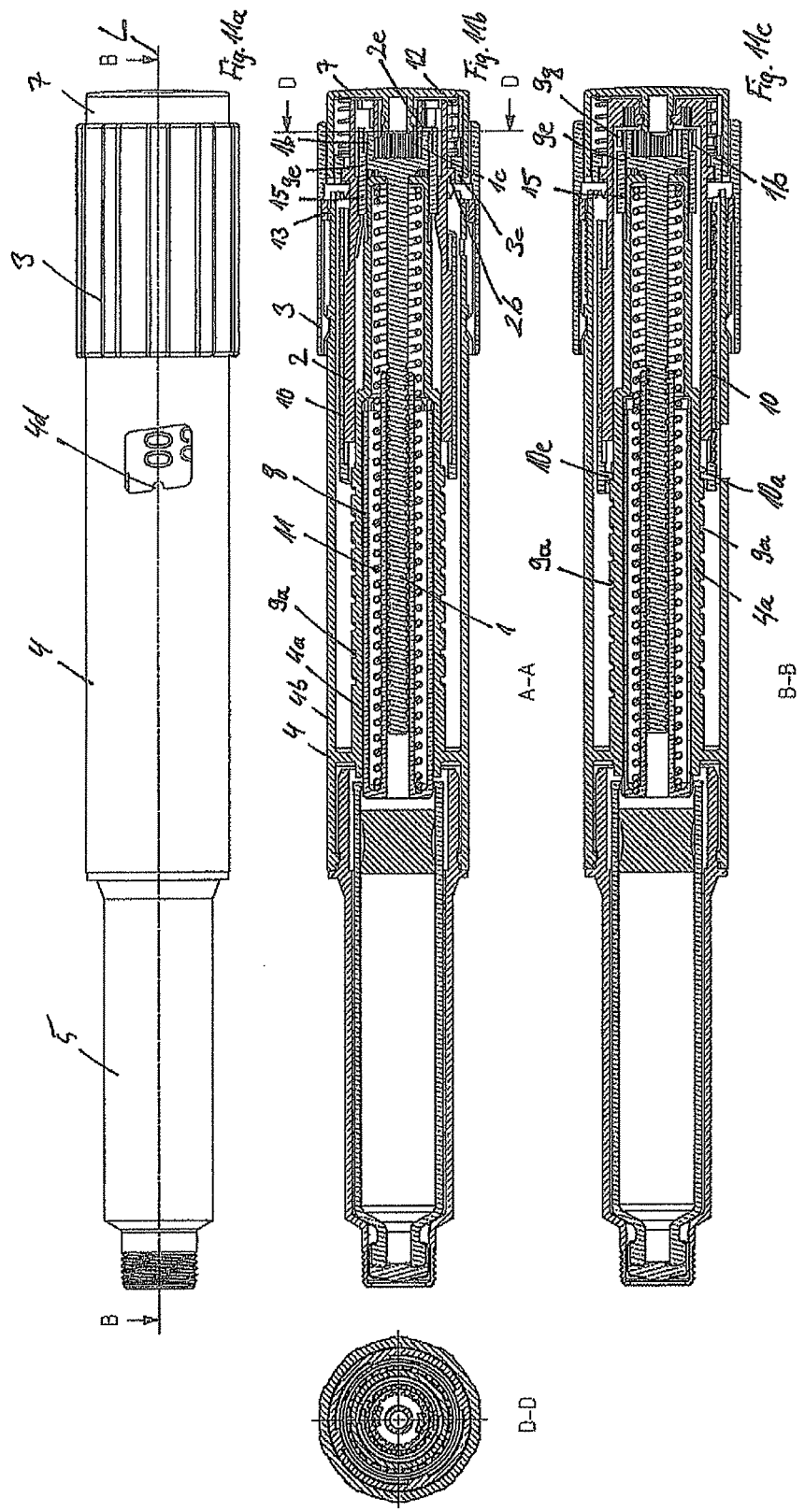

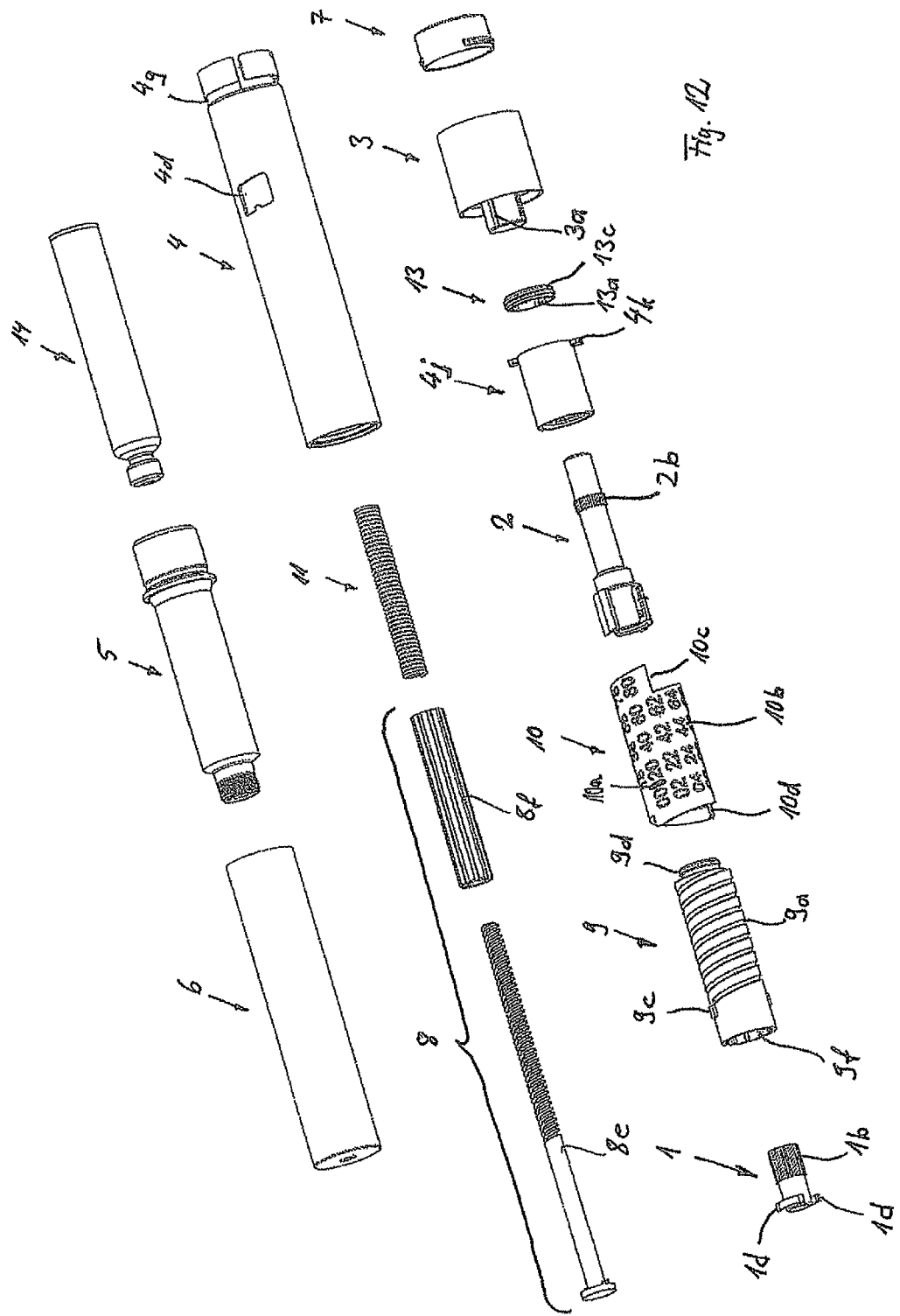

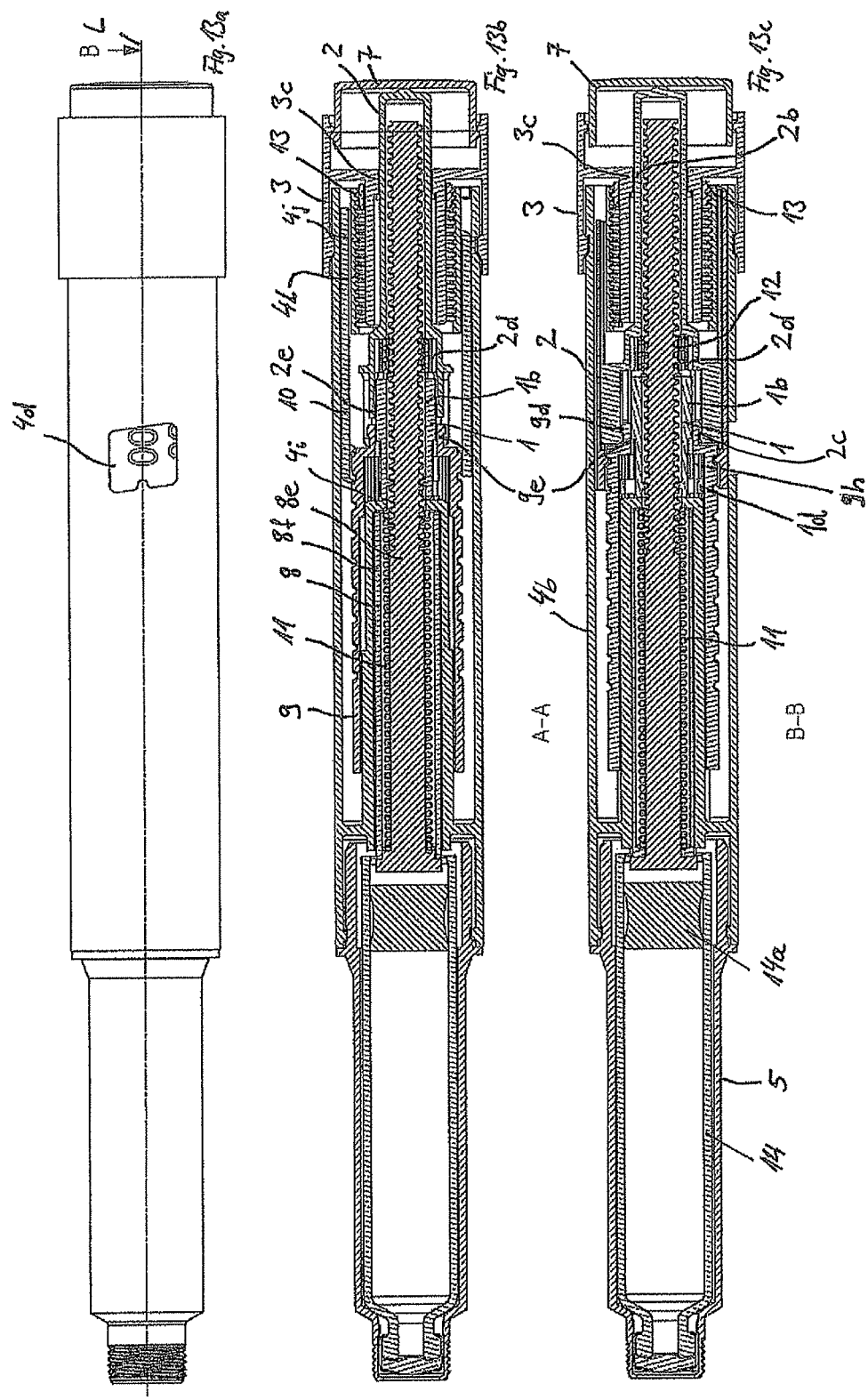

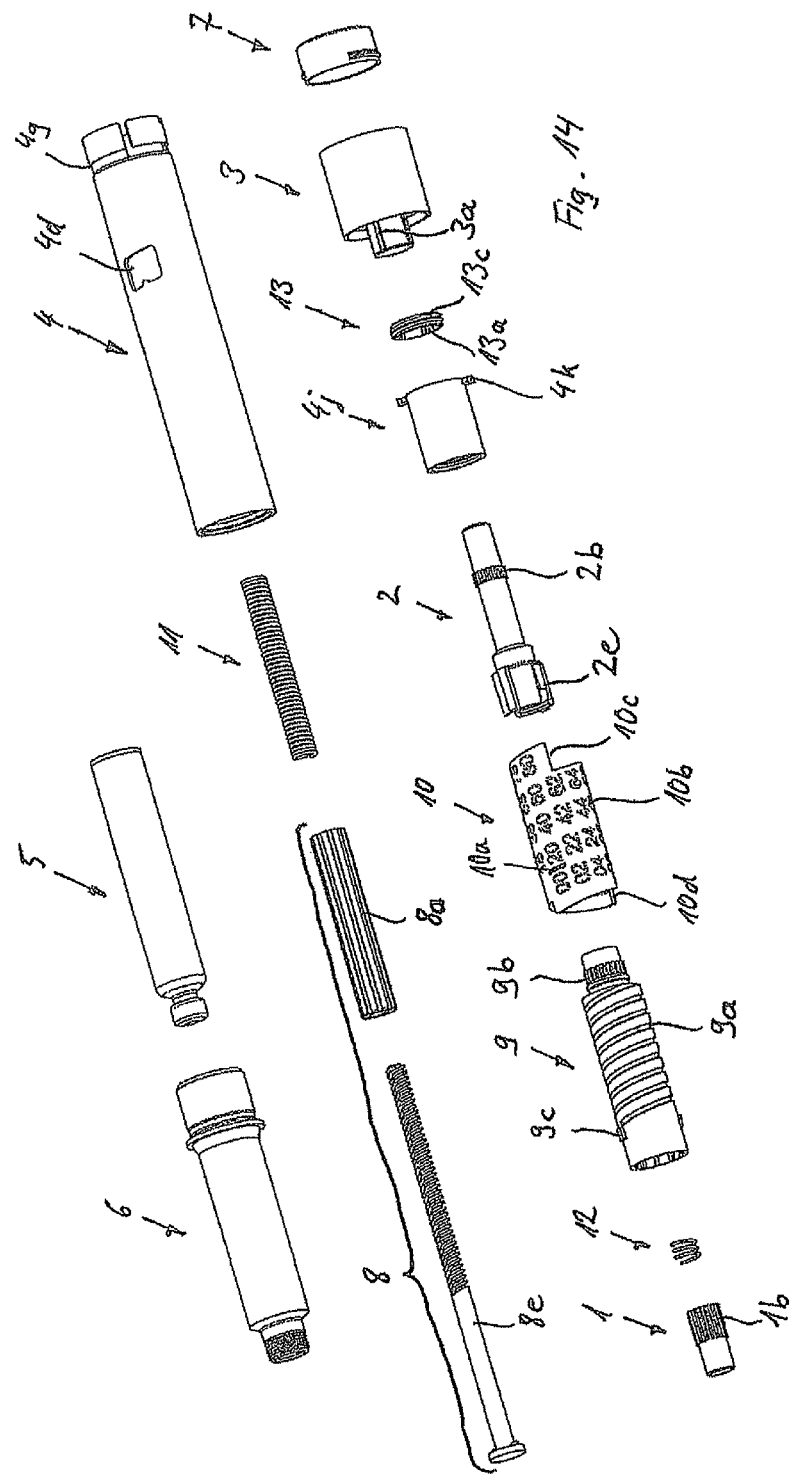

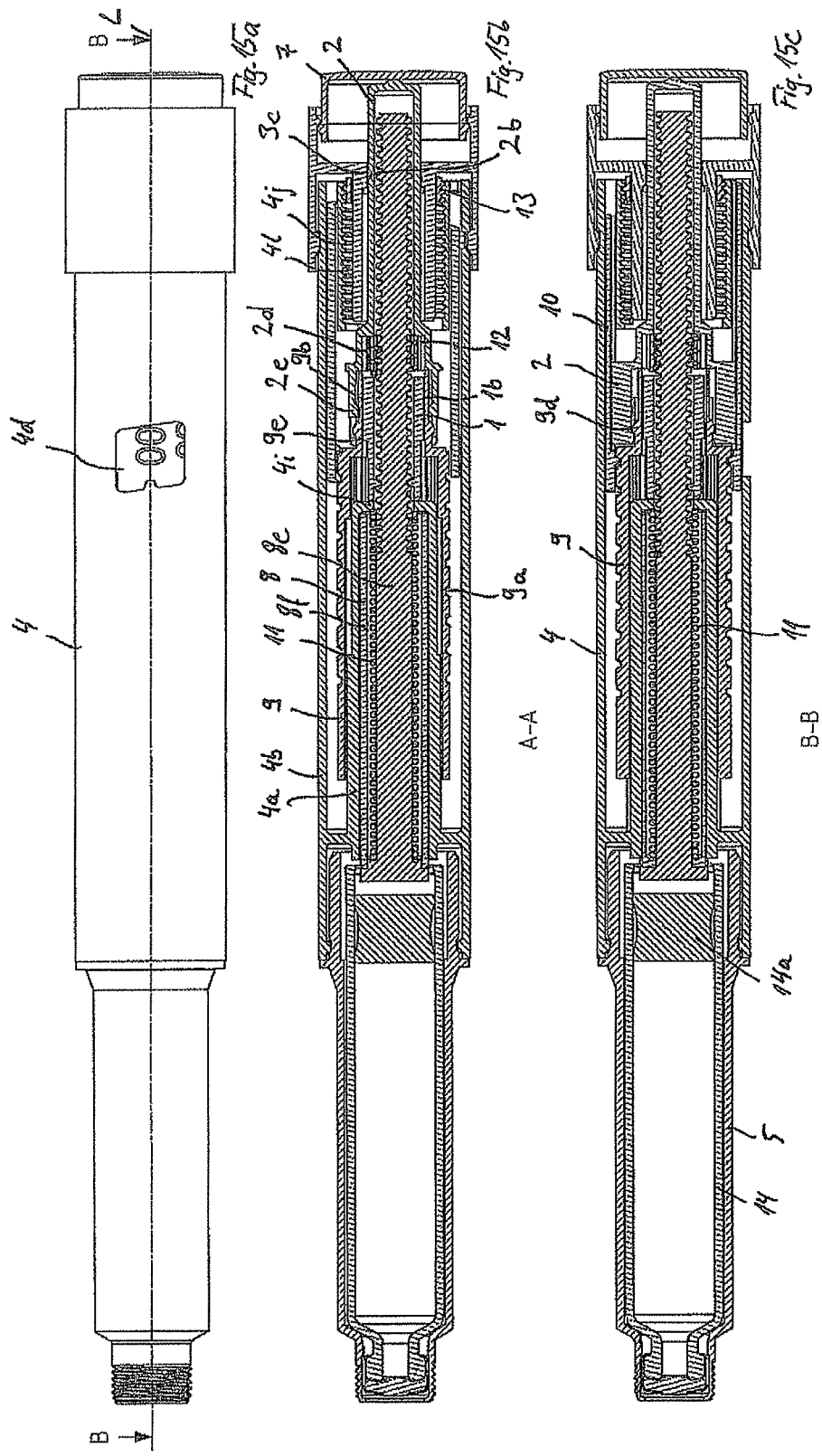

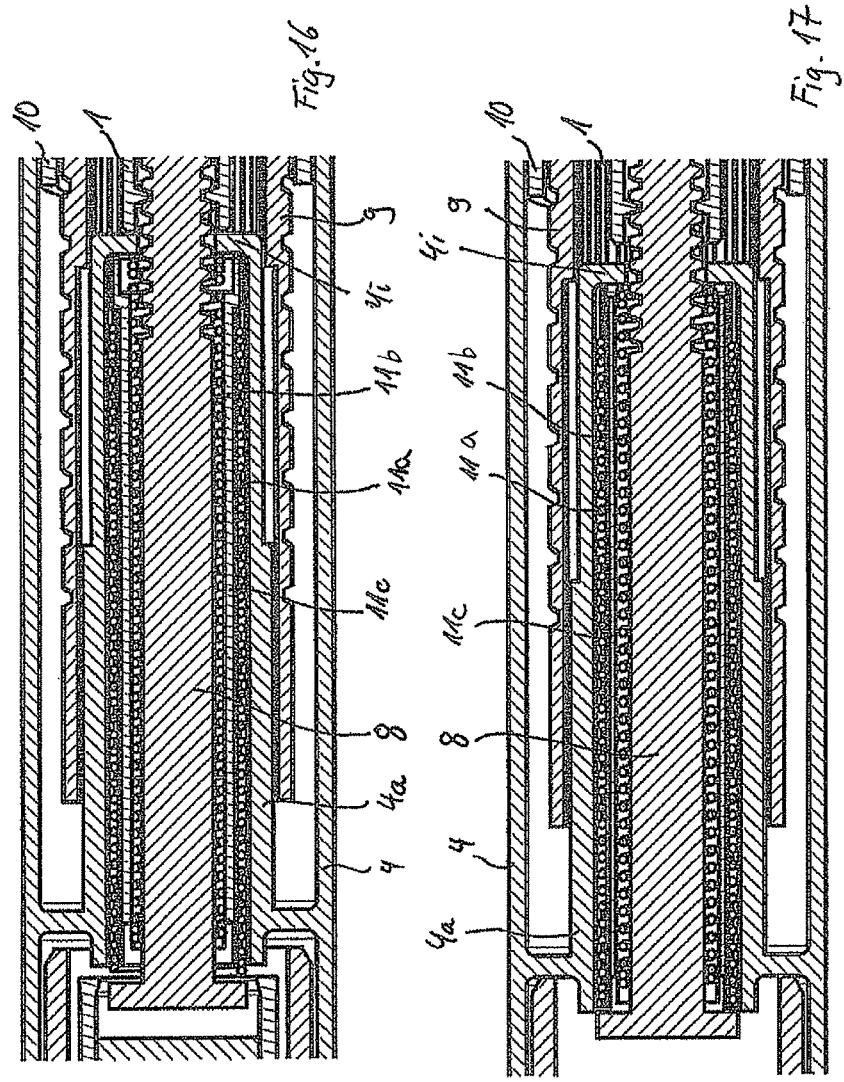

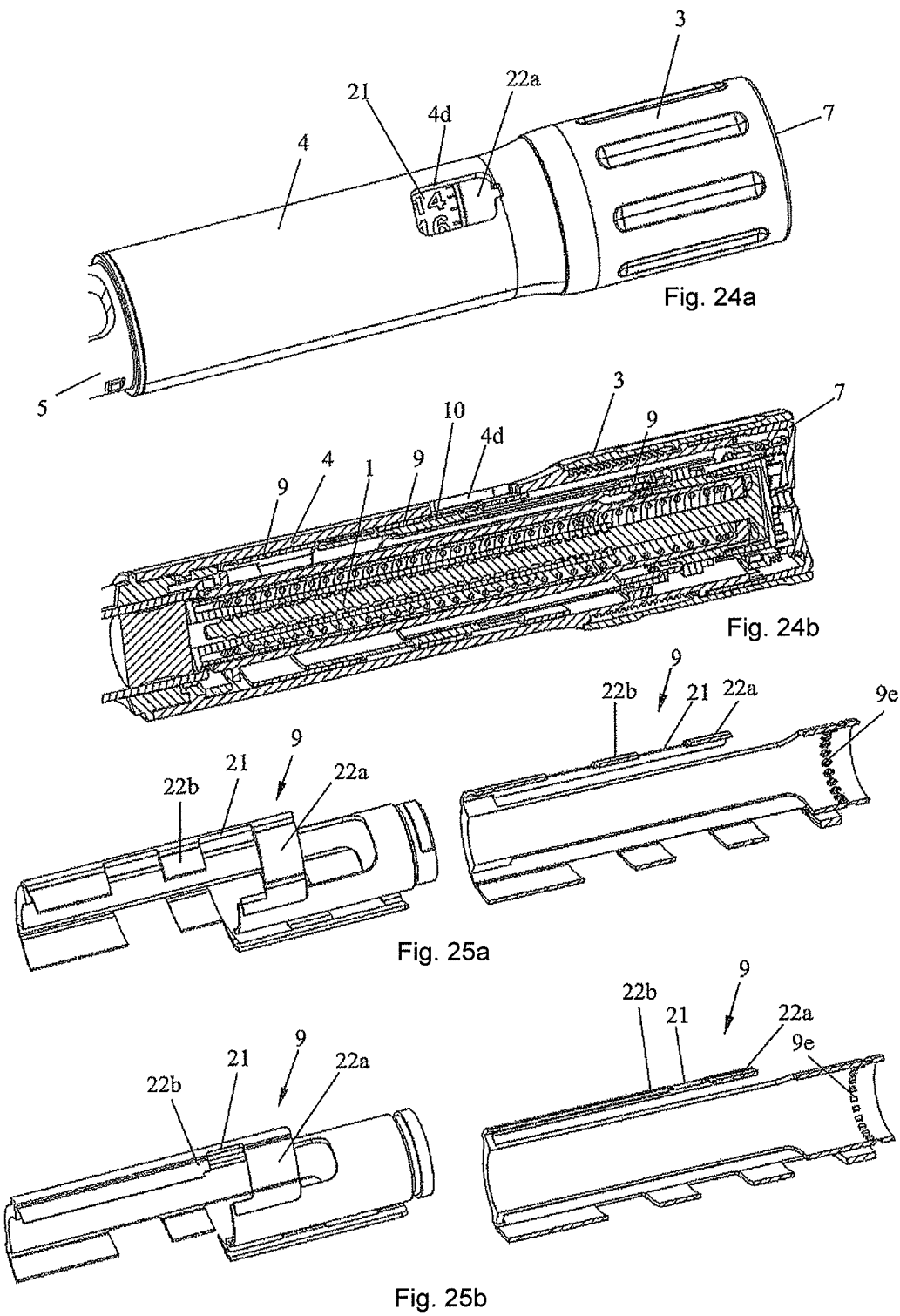

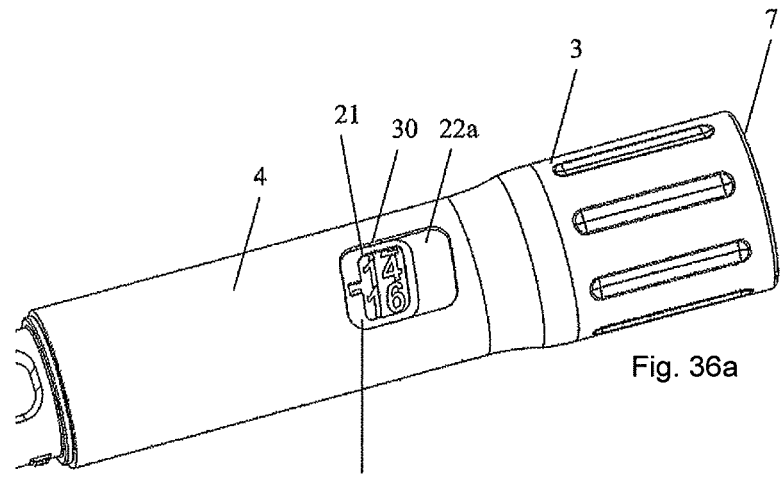
Fig. 36a
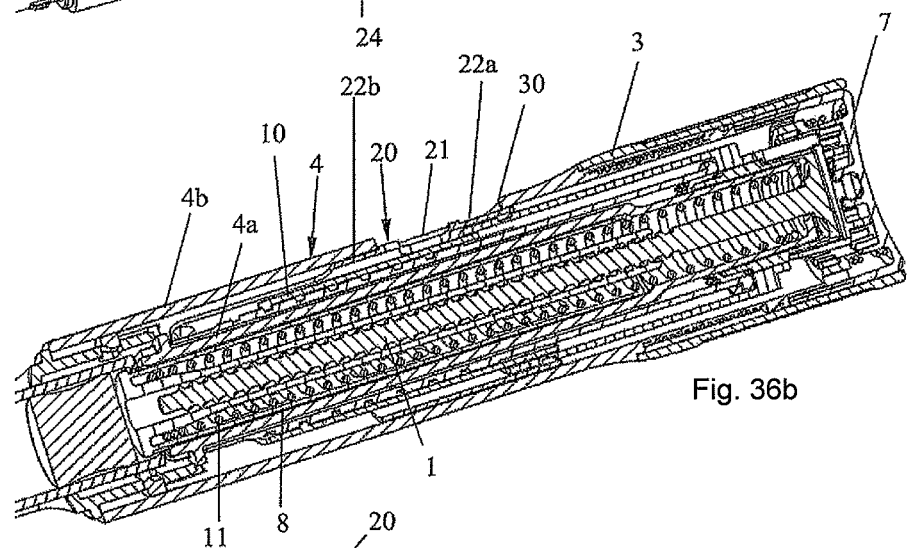
Fig. 36b
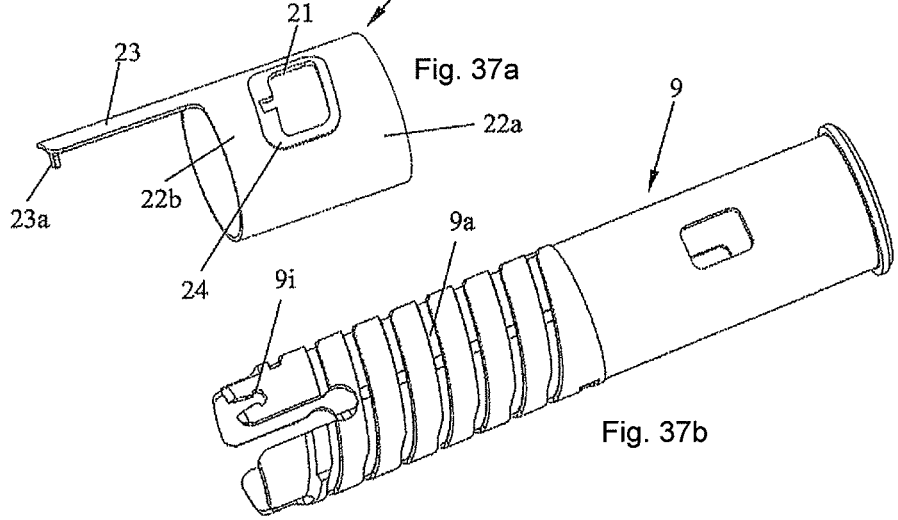
Fig. 37a
Fig. 37b

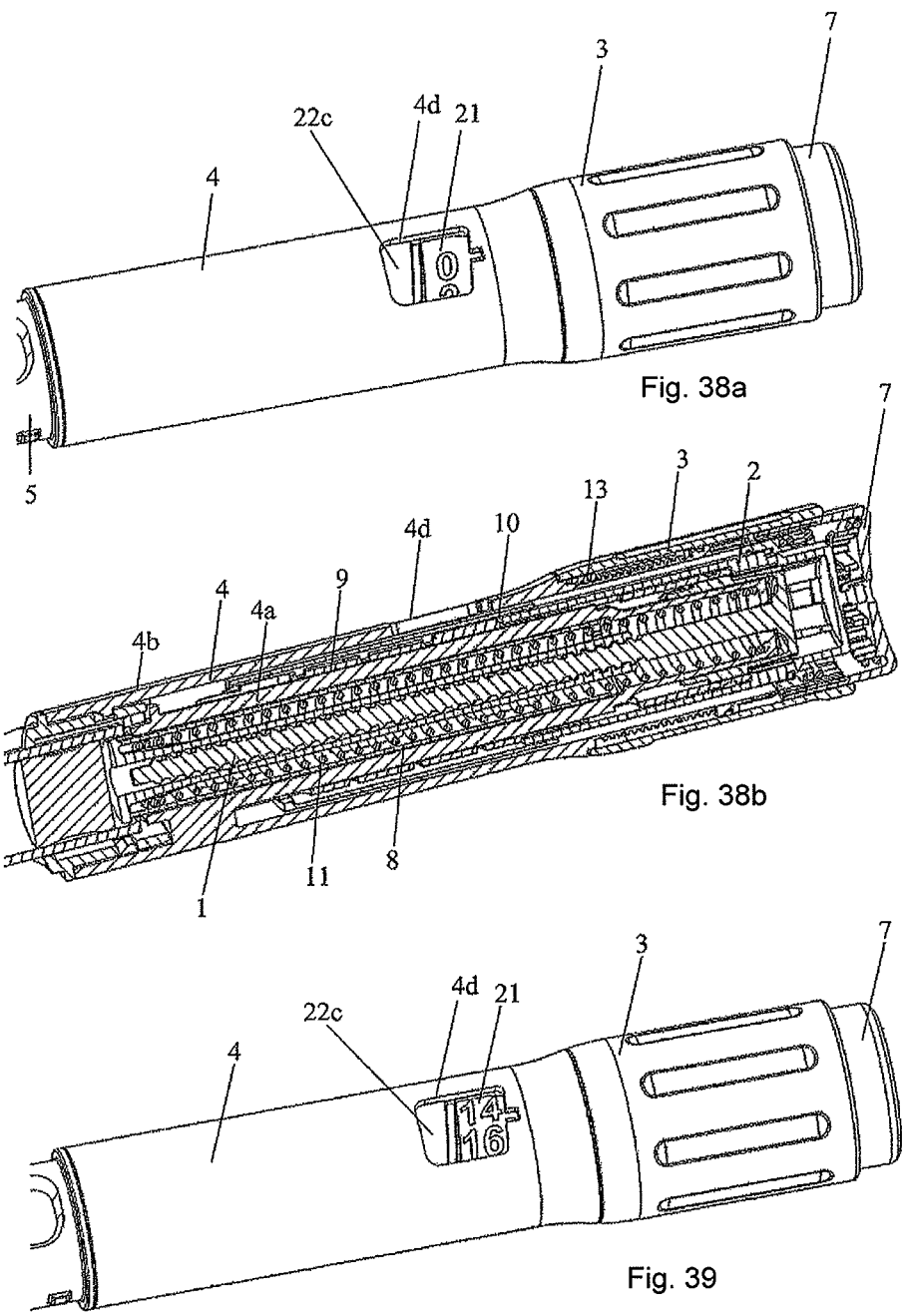

even pages.

INJECTION DEVICE HAVING A DOSE INDICATING ELEMENT THAT CAN BE MOVED RELATIVE TO A HOUSING

CROSS-REFERENCE TO RELATED APPLICATIONS

This application is a Continuation of International Patent Application No. PCT/EP2013/056093 filed Mar. 22, 2013, which claims priority to European Patent Application No. EP 12 162 777.2 filed Mar. 30, 2012, the entire contents of each are incorporated herein by reference.

BACKGROUND

The invention relates to an injection device for administering a liquid product, particularly a medicine, such as insulin for diabetes therapy. In particular, the invention relates to a driving and dosing device for such an injection device.

An injection device having a dose indicating drum and a drive spring is known from the prior art, namely WO 2008/031237 A1. The drive spring is a coiled spring, which is wound in a spiral shape from a strip-shaped material. When the product dose is being set, the spring is tensioned with a rotational movement. In order to inject a dose, a piston rod is coupled to the spring by means of an actuating button at the proximal end of the device, whereby the spring can output the energy stored therein to the piston rod, whereby the piston rod is moved in the discharge direction. To set a new dose, the spring is again cocked by rotating the dosing knob, and so on. This is repeated until the product container has been emptied.

An injection device with a helical spring is also known from U.S. Pat. No. 5,104,380 A, the spring being likewise cocked rotationally during dosing, so that the helical spring can also be referred to as a torsion spring. The spring, cocked by rotation before each product discharge, transfers its energy to the piston rod in order to propel the piston rod.

WO 2006/77466 A2 discloses an injection device that has a direct mechanical drive between the person applying the injection force and the piston rod, which is displaced in the distal direction for the injection of the medicine.

SUMMARY

One problem addressed by the invention is that of specifying a driving and dosing device for an injection device with an improved dose indication and which in particular gives the user of the device better information about the operating condition of the device.

This problem is solved by the features and refinements of the claims, the description and the figures.

One problem addressed, particularly in an advantageous refinement of the invention, is that of indicating a driving and dosing device for an injection device used to administer a liquid product, which enables easier usage of the device for the user, in particular a simpler setting of the dose. This problem is solved particularly by the features of the second aspect described herein.

The invention proceeds from a drive mechanism for an injection device for administering a liquid medicine or product. The drive mechanism has a housing. The housing is preferably sleeve-shaped and/or elongated in shape. The housing can extend along a longitudinal axis, for example.

The housing can optionally accommodate a product container or can itself constitute the product container. The housing can be in one or more parts. For example, the housing can form a proximal housing part that comprises or has the driving and dosage device. The housing can additionally have a product container holder, which receives the product container such as a carpule and is connected to the housing or the proximal housing part. This connection can be such that the product container holder and the housing or the proximal housing part is non-detachable after connection, i.e. only detachable by destroying connecting elements. Such a solution is particularly advantageous for single-use injection devices, which can be disposed of as a whole after the product contained in the product container has been completely discharged. Alternatively, the product container holder can also be detachably connected to the housing, whereby it is possible, although also less preferred, to use the driving and dosing device several times if necessary, i.e. to replace an empty product container with a filled product container.

The housing is principally used in order to be gripped by the user of the device. In particular, the housing can have a substantially cylindrical shape. The housing can have a pointing device, particularly a window, by means of which or through which the currently set dosage can be read out, preferably from a scale of the dose setting element.

In a first aspect, the driving and dosing device, which in particular forms an injection device together with the container, comprises a dose indicating element, across the periphery of which a dose scale is arranged, in addition to a housing. The dose indicating element can be annular in cross section, for example. The dose indicating element can be a dose indicating drum or a dose indicating ring, for example. The dose scale can extend over the periphery of the dose indicating element, preferably in a helical shape. The dose scale preferably comprises a plurality of values, which are arranged one after another and produce the dose scale. These are preferably numerical values that indicate the desired product dose in international units (IU).

Alternatively, the dose scale can be arranged without a pitch over the periphery of the dose indicating element, such as the dose indicating ring, in which case the scale values then repeat after a revolution of the dose indicating element. In a dose scale with a pitch, i.e. a helical dose scale, the dose indicating element, particularly the dose indicating drum, can be rotated more than one revolution without the scale values repeating, whereby higher or more scale values can advantageously be represented.

The driving and dosing device further comprises a pointing device, wherein the dose indicating element, in order to set the dose, can be rotated relative to the pointing device and particularly about a rotational axis that preferably corresponds to the longitudinal axis of the driving and dosing device and/or the dose indicating element. This movement can be a purely rotational movement, i.e. a rotational movement without superimposed axial movement. Preferably an axial movement is superimposed on the rotational movement, whereby the dose indicating element is screwable relative to the pointing device in order to set the dose to be administered. A screwable dose indicating element can be advantageously combined with a helical dose scale, the screwing movement and the dose scale preferably having the same pitch. A dose indicating element without axial movement can be advantageously combined with a pitch-free dose scale.

A value of the dose scale, which corresponds to the set dose, can be read by means of the pointing device, which can be formed on the housing or a body that is movable or displaceable along the longitudinal axis relative to the housing. The pointing device can be a window for example, which can be formed by an opening in the housing or in the body or by a transparent insert or region in the housing or in the body. Alternatively or optionally, the pointing device can be an arrow or have an arrow, which marks the value of the dose scale corresponding to the set dose in addition to the window. This is advantageous if a second value appears in the window, at least partially, in order to ensure an unambiguous choice of dose, for example. The pointer can be a protrusion or an imprint or a notch or the like on the housing or the body.

The driving and dosing device comprises a dosing element, which can be formed as a dosing knob for example, and can optionally be referred to as a setting element. The dosing element can preferably be gripped by the user (patient, physician, medical assistance personnel) of the driving and dosing device and preferably constitutes an external, more particularly externally accessible, surface of the driving and dosing device. To adjust the dose to be discharged or administered, the dosing element is preferably gripped by the user and rotated relative to the housing, and in particular to the pointing device, about an axis of rotation, which preferably corresponds to the longitudinal axis of the driving and dosing device, which is designed in an elongated shape for example. The dosing element is preferably connected axially fixedly to the housing, more particularly secured against displacement along a longitudinal axis of the housing, whereby the intuitive handling of the device by the user is advantageously facilitated, because the user needs only to carry out a rotational movement of the dosing element to adjust the dose.

In particular, the dose indicating element can be secured against rotation relative to the dosing element at least during the dose-setting, but connected or coupled to the dosing element so as to be axially displaceable. For intuitive operation, it is advantageous if, when the dosing element is rotated by a given angle of rotation, the dose indicating element is rotated by the same angle of rotation and the two may be slaved in rotation.

The driving and dosing device can have an actuating element, e.g. in the form of an actuating button. The actuating element can form an outer surface of the driving and dosing device and/or can be accessible from the outside. The actuating element can be formed on the proximal end, in particular the rear end, of the driving and dosing device or can constitute this end. In this manner, the actuating element can advantageously be actuated, particularly pressed, with the thumb of the hand that is gripping the housing. The actuation can be ended by releasing the actuating element. "Actuating" is understood to mean the displacement of the actuating element into the driving and dosing device, more particularly in the distal direction, which can affect the discharging of a product. The actuating element is advantageously displaceable relative to the dosing element and in particular can be received by the dosing element so as to be displaceable axially.

The actuating element can advantageously be displaceable, more particularly actuatable, against the force of a spring, particularly a return or coupling spring, whereby this spring is cocked. By being released, this spring can reset the actuating element, more particularly displace it relative to the dosing element, specifically in the proximal direction or out of the driving and dosing device.

The driving and dosing device further comprises a bearing element, with which the dose indicating element is engaged. This engagement advantageously effects the rotational or screwing movement of the dose indicating element relative to the pointing device. For example, the engagement between the dose indicating element and the bearing element can be a threaded engagement. In particular, the bearing element can have an external thread and the dose indicating element an internal thread, or vice versa, these threads engaging with one another and thereby causing the dose indicating element to be screwable relative to the bearing element.

The dose indicating element can be rotated or screwed between a maximum dose position and a zero dose position. In the zero dose position, the dose or the digit "0" can advantageously be readable in the pointing device. In the maximum dose position, the maximum product dose that can be discharged with the driving and dosing device can advantageously be readable.

The dose indicating element can be blocked in the zero dose position against rotation in one rotational direction, namely the rotational direction that would cause a dose of less than zero to be set. In the zero position, the display element can preferably only be rotated in a direction of rotation that causes an increase of the dose. In the maximum dose position, the dose indicating element is preferably blocked against rotation in one rotational direction, namely the rotational direction that would cause the setting of a dose greater than the maximum settable dose. Preferably, the dose indicating element in the maximum dose position can only be rotated in the direction that causes a reduction of the product dose.

For example the dose indicating element can have a stop that strikes against a mating stop in the zero dose position and thus prevents rotation in one rotational direction. The same or an additional stop on the dose indicating element can prevent rotation of the dose indicating element past the maximum dose. In particular, an additional mating stop, namely a maximum dose mating stop, can be provided for this purpose. The other mating stop can accordingly be referred to as the zero dose mating stop. Thus the dose indicating element can have a zero dose stop for the zero dose mating stop and a maximum dose stop for the maximum dose mating stop. The stop or the stops are preferably active in the circumferential direction and/or in the axial direction.

The driving and dosing device is characterized in a first aspect in that the bearing element, together with the dose indicating element, is displaceable relative to the housing and along the axis of rotation, particularly in the distal direction. This aspect can advantageously improve the driving and dosing device according to a second aspect described herein. Alternatively the dose indicating element can have a thread that is engaged with the housing. Thereby the dose indicating element can be displaced back and forth relative to the housing but not independently of the screwing movement, particularly not with a purely axial movement.

The actuating element is preferably coupled to the bearing element, via a clutch element for example, in such a manner that a displacement of the actuating element relative to the housing and/or the dosing element causes a displacement of the bearing element relative to the housing and/or the dosing element, particularly along the longitudinal axis of the driving and dosing device.

Because the dose indicating element is engaged according to the invention with the bearing element and the bearing element can be displaced relative to the housing and along the axis of rotation, the dose indicating element can also be displaced relative to the housing and along the axis of rotation independently of the rotating or screwing movement that the dose indicating element undergoes during setting of the dose. The driving and dosing device according to the second aspect can basically also be combined advantageously with the alternative dose indicating element, which is in threaded engagement with the housing or an element fixed relative to the housing. In this alternative, the bearing element can be formed by the housing or be a part of the housing, wherein the bearing element can then be secured rotationally and axially in relation to the remainder of the housing.

The fact that the bearing element has been displaced together with the dose indicating element can advantageously be read out on the pointing device or the dose indicating element. In this way, the user can monitor the operating status of the driving and display device, i.e. whether the driving and display device, and in particular the actuating element, is or is not actuated for a discharge.

In variants that refine the invention, the actuating element and/or the bearing element can be displaceable together with the dose indicating element relative to the pointing device, the housing and along the axis of rotation. In the area of the pointing device, particularly in the window of the pointing device formed on the housing, a marking different from the dose scale can appear when the bearing element has been displaced. The marking is preferably arranged on the dose indicating element. If the bearing element has not been displaced, more particularly the driving and dosing device has not been actuated for discharging the product, the marking can be arranged outside the pointing device, for example concealed by a housing or some other element. If the bearing element has been displaced, in particular if the driving and dosing device has been actuated for discharging the product, the marking can emerge from the covered area, so that it appears or is readable on or in the pointing device. If the actuation of the driving and dosing device has been interrupted or terminated, the bearing element can return to the original position, whereby the marking preferably is removed from the area of the pointing device and in particular is concealed.

In alternative variants that refine the invention, the actuating element and/or the bearing element can be displaced relative to the housing and along the axis of rotation together with the dose indicating element and the pointing device, preferably formed by or on a body. The pointing device can be a screen for example or at least perform the function of a screen. For example the pointing device can be connected to the bearing element at least axially fixedly, preferably also rotationally fixedly or rotatable together with the bearing element. Basically the bearing element can form the pointing device, for example the body forming the pointing device. It is of course also possible for the body forming the pointing device to be a part separate from the bearing element. The body forming the pointing device can be sleeve-shaped or shell-shaped, for example.

In these variants, the displacement of the bearing element can cause a marking, which is arranged or formed alongside or on top of the pointing device or the body and differs from the dose scale, to appear in the area of the pointing device. For example, the pointing device or the body forming a pointing device can be arranged inside the housing. The marking of the pointing device can be concealed by the housing or another element in the non-actuated state of the driving and dosing device. If the driving and dosing device, more particularly the actuating element, is actuated and thus the dose indicating element is displaced together with the pointing device, the marking can emerge from its covering, so that the marking is visible or readable. If the actuation is interrupted or terminated, the dose indicating element, together with the pointing device and the bearing element, can be displaced back into its initial position and therefore the marking is again arranged under the cover. As stated, the marking is only optional.

In the alternative variants, the housing can have a window (housing window), particularly an opening or a window made of a transparent material that allows a view by the user or patient from the outside, i.e. from the surroundings, into the interior of the device and onto the pointing device. Preferably the window is larger than the pointing device visible through it, so that when looking through the window, the pointing device, more particularly a window or a region with a first color, a region proximally adjoining the pointing device and/or a region distally adjoining the pointing device is also recognizable. The proximal and distal regions are formed by the body that forms the pointing device. In every position of the actuating element, at least one of the regions proximal and distal to the pointing device is visible through the housing window in addition to the pointing device. The proximal region can have the above-mentioned marking for example.

The pointing device can be arranged between the housing window and the dose indicating element. The body forming the pointing device can be arranged between the dose indicating element and the housing. If the pointing device is arranged between the housing window and the dose indicating device, it is preferably designed such that it allows or permits a view from the exterior onto the dose indicating element. The user then looks through the housing window and the pointing device onto the dose indicating element, particularly the outer periphery and/or the dose scale thereof The pointing device is arranged between the proximal and distal regions. The proximal and distal regions adjoining the pointing device can be opaque. Thereby only the value of the dose scale that is present in the pointing device can be read. The pointing device formed in this manner has the effect of a screen. The values of the dose scale that are not to be visible are covered or screened out by means of the distal and/or proximal region.

The body forming the pointing device can be formed by the clutch element, for example, or the bearing element or a part separate from the clutch element and/or bearing element.

For example, the body that forms the pointing device can be formed or produced from an opaque material, particularly plastic. The pointing device can be a window, particularly an opening, or can be formed from a transparent material, particularly plastic. The opaque material surrounding or adjoining the pointing device forms the distal and proximal regions.

The body that forms the pointing device can alternatively be formed or produced from a transparent, particularly a completely transparent, material, in which case the distal and/or proximal region is an imprint, a coating or a processed region of the transparent material, the processing having rendered the transparent material opaque. An example for such a processing is radiation with an energy beam such as a laser.

The dose indicating device and the body that forms the pointing device interpenetrate one another by means of a threaded connection, the body being indirectly or directly connected to the bearing element at least in such a manner that it follows the movement of the bearing element along the longitudinal axis.

If the pointing device is formed by the clutch element, it is preferred that the pointing device extends annularly or across the periphery of the sleeve-shaped clutch element.

The clutch element is rotatable relative to the housing, so that the pointing device is likewise rotatable relative to the housing or is rotated during dose setting. The proximal and distal regions advantageously likewise extend annularly or across the circumference of the sleeve-shaped clutch element. The clutch element can be produced from a transparent or opaque material for example.

If the body forming the pointing device is formed from the bearing element in a monolithic manner, for example, a gap in which the dose indicating element is arranged can be formed between the portion forming the body and a sleeve like portion of the bearing element. The portions can be connected via a radial connecting web that is arranged distally from the dose indicating element.

If the pointing device is formed by a body separate from the bearing element, this body can penetrate into the bearing element in such a manner that the body and the bearing element are at least axially fixed relative to one another and preferably also fixed against rotation about the longitudinal axis. A gap in which the dose indicating element is arranged can be formed between the body and the bearing element. The body and the bearing element can be connected via a radial connecting web arranged downstream of the dose indicating element. The body in this case can be sleeve-shaped for example, and the dose indicating element can surround it on the periphery.

If the body forming the pointing device is a part separate from the bearing element, the body can be secured against rotation about the longitudinal axis by the housing or a housing insert and can be guided displaceably along the longitudinal axis. If a housing insert is present, it can form the housing window. The housing insert is inserted into a cutout of the housing and joined to the housing, particularly welded, glued or snap-fit. The advantage of the housing insert is that it facilitates the assembly of the device. The housing insert can be fixed to the housing in one of the final production steps. The housing or the housing insert forming the housing window can form a guide, which guides the body forming the pointing device secured against rotation along the longitudinal axis. The guide can surround the body along its flanks, which run parallel to the longitudinal axis, for example. This is particularly advantageous if a housing insert forms the guides, in order to prevent the body from detaching from the housing insert when the latter is handled during assembly. The housing insert and the body can thus advantageously be handled as a unit.

The body separate from the bearing element can be mounted axially fixedly and rotatably on the clutch element or penetrate into the clutch element. The clutch element can thus be rotated relative to the body. For this purpose, one of the two elements consisting of the clutch element and the body can have a peripherally extended, e.g. annular groove, the other of the two elements engaging in this groove.

Alternatively, the dose indicating element can have an external thread on its outer periphery for example, with which the body forming the pointing device engages. The dose indicating element can additionally form an internal thread that engages with the external thread of the bearing element. The external thread and the internal thread of the dose indicating element preferably have the same thread pitch, more particularly the pitch of the helical scale. This causes the dose indicating element to be screwed to the same extent on the body and on the bearing element while setting the dose, so that the body remains fixed in relation to the housing during the dose setting and is only displaced along the longitudinal axis during actuation of the actuating element, by being driven by the dose indicating element.

Alternatively, the body forming the pointing device can be connected axially fixedly and preferably also rotationally fixedly to the bearing element, and can in particular be engaged with the bearing element or consist of a single piece with the bearing element, as already described above.

In additional embodiments, the dose indicating element can be arranged between the pointing device and the housing window. The dose indicating element can consist of a transparent material, particularly plastic, wherein the symbols that form the dose scale have a symbol color. In the area of the housing window, a first region, forming the pointing device and having a first color, and a second region, having a second color, are arranged behind the dose indicating element. The second region can surround the first region, for example. The first region is behind a part of the dose scale, i.e. the first region is arranged behind the dose scale in the direction of view, and the second region is behind another part of the dose scale, i.e. the second region is arranged behind the dose scale in the direction of view. The contrast between the symbol color and the first color is greater than the contrast between the symbol color and the second color. This has the advantageous effect that the part of the dose scale arranged in front of the first region can be recognized better by the user than the part of the dose scale arranged in front of the second region. For example, if the symbol color is black and the color of the first region is white and the color of the second region is anthracite or black, there is a better contrast between black and white than between black and anthracite or black and black. This of course also works with other color combinations.

The first region and the second region can preferably be connected indirectly or directly to the bearing element at least in such a manner that they follow the movement of the bearing element along the longitudinal axis. For example, the bearing element can form the first and second regions. The bearing element can consist of a plastic dyed with the second color, for example, while the first color for forming the first region or the pointing device can, in particular, be printed onto the bearing element. Alternatively, the first and second regions can be printed, in which case the color of the plastic is unimportant.

The clutch element is connected rotationally fixedly and axially displaceably to the dose indicating element. The dose indicating element is in threaded engagement with the bearing element, which is mounted rotationally fixedly and axially displaceably on the housing. The clutch element is connected axially fixedly and rotatably to the bearing element. A rotation of the clutch element relative to the bearing element thus causes the dose indicating element to be screwed along the bearing element, whereby the desired dose is set and displayed.

It is generally preferred that a spring, particularly a coupling or return spring, is cocked for actuating the driving and dosing device in order to discharge a product. In other words, the bearing element can be displaced during actuation against the force of the spring, particularly a spring of this type, from a non-actuated position into an actuated position. The spring can be a helical spring or a coil spring, for example, acting as a compression spring. This spring has the further effect of resetting the bearing element to the starting position or non-actuated position if the actuation is interrupted or ended. In particular, the bearing element is displaced in the distal direction during actuation. The bearing element is pushed back into its original position by means of the spring if the actuation is interrupted or ended.

Actuating the actuating element has the effect in particular of displacing the bearing element together with the dose indicating element relative to the housing and along the axis of rotation. In the broader sense, the actuation of the actuating element can displace a propulsion element, the distal end of which is provided to act in the distal direction, more particularly the discharging direction, on a piston of the product container mounted .or mountable on the driving and dosing device. The actuating element can be arranged at the proximal end, i.e. rear end, of the driving and dosing device or can form the proximal end of the driving and dosing device. Alternatively, the actuating element can be arranged laterally on the housing and/or between the distal end and the proximal end of the driving and dosing device. In general, the actuating element can be formed in the manner of an actuating button. During actuation, the actuating element is preferably displaced relative to the housing or the dosing element. In particular, the user of the device can advantageously actuate the actuating element with the thumb of the hand that is gripping the housing of the driving and dosing device, for example.

The actuating element is preferably connected to the bearing element in such a manner that it displaces the bearing element during actuation, more particularly via a clutch element which can be connected axially fixedly and rotatably to the bearing element for example.

In generally preferred embodiments, the actuation of the actuating element can cause the dose indicating element to be rotated, particularly screwed, relative to or on the bearing element or the housing, more particularly in a direction such that the values moving past the pointing device during the rotational movement count down on the dose scale. The angle of rotation of the dose indicating element and the discharge stroke of the propulsion element preferably have a proportional relationship, more particularly at every point during the dose discharging. This makes it possible to implement a real-time display, which counts down during dose discharging until it finally reaches the value 0, at which point the discharging of the dose in question is complete. If the actuation for discharging is interrupted during the back-rotation of the dose indicating element, the dose indicating element indicates the remaining amount necessary for the discharging of this dose.

In one variant, the drive and dosing device can be designed such that the energy required for the back-rotation of the dose indicating element and/or the displacement of the propulsion element in the distal direction must be applied manually, more particularly by a force exerted on the actuating element by the user. For example, the dose-setting element, more particularly the dosing knob, can be screwed out of the housing for setting the dose, being screwed back into the housing for dose discharging by actuation of the actuating element.

In a preferred alternative variant, the drive and dosing device can be designed such that the energy required for the back-rotation of the dose indicating element and/or the displacement of the propulsion element in the distal direction is exerted automatically, more particularly by means of a spring contained in the driving and dosing device, in particular a discharge spring, in which the required energy is or can be stored. For example, the spring energy stored in the discharge spring can be output upon actuation of the actuating element to the dose indicating element and/or the propulsion element, so that the dose indicating element is rotated back and the propulsion element is displaced in the distal direction. The discharge spring can be coupled to the dosing element for example in such a manner that a rotation of the dosing element cocks the discharge spring during the dose-setting. The spring can then store the energy required for the set dosage.

In a preferred alternative, the spring can already be cocked with sufficient energy upon delivery of the driving and dosing device that the energy suffices for several discharges of the product dose, in particular for discharging the entire product that can be discharged from the product container. In this alternative, the dosing element can be decoupled from the spring during dose-setting, i.e. not coupled to the discharge spring in such a manner that a rotation of the dosing element cocks the spring. In this manner the dosing element can be rotated by the user to set the dose with considerably less force exertion.

The dosing element, more particularly the dosing knob, can surround or receive the actuating element, specifically the actuating button. Thus the dosing element and the actuating element can form the proximal end of the driving and dosing device. The actuating element is preferably displaceable relative to the dosing element for actuation.

In embodiments in which the energy required for the discharging is automatically provided, the dosing element can preferably be arranged axially fixedly or rotatably relative to, and in particular on, the housing.

In a second aspect, which can be combined with features of the first aspect, particularly with or without the feature that the bearing element is displaceable together with the dose indicating element relative to the housing and along the rotational axis, the driving and dosing device can have a propulsion element, the distal end of which acts on a piston, more particularly indirectly or preferably directly. The piston can be part of a product container such as a carpule mounted or mountable on the driving and dosing device. In a broader sense, the propulsion element can be considered a piston rod, wherein the propulsion element need not necessarily be solid, but can also be hollow, e.g. sleeve-shaped. A flange, rotatable for example, that presses against the piston, can optionally be arranged at the distal end of the propulsion element. It is generally preferred that the distal end of the propulsion element presses against the piston. The propulsion element is preferably displaceable relative to the housing along the longitudinal axis of the driving and dosing device.

The driving and dosing device can have an abutment and preferably a guide, wherein the propulsion element is displaceable relative to the abutment and preferably also relative to the guide in a direction, more particularly the distal direction or the discharging direction, in order to bring about the discharging of the set product dose. The propulsion element can preferably be moved by means of or on the guide along the longitudinal direction of the driving and dosing device in a straight line or axially. In particular, the propulsion element can be rotationally fixed relative to the abutment and/or the guide and/or the housing. In an alternative embodiment, the propulsion element can be rotatable relative to the abutment for the housing combined with a longitudinal movement, i.e. screwable relative to the abutment, although this is less preferred. In general, the guide and/or the abutment can be formed from the housing, particularly a sleeve-shaped housing part or a sleeve-shaped element fixed to the housing, for example.

The propulsion element and the guide, formed in particular by the housing, can be in an engagement that prevents a rotation of the propulsion element relative to the abutment or the housing, but allows an axial movement or a screwing movement of the propulsion element relative to the abutment of the housing. The guide can be an axial guide or a thread with a non-self-locking thread pitch.

The guide or the housing section, more particularly an inner sleeve the forms the abutment and/or the guide, can preferably surround the propulsion element, in a sleeve-like manner, and/or can be fixed relative to the housing or formed by the housing. An annular gap can be formed between this sleeve-shaped housing part and the external, preferably also sleeve-shaped, housing part, which brings the advantage that an optionally present dose indicating element, particularly an indicating drum, can be received therein. This results in that the length of the driving and dosing device can be kept small.

According to the second aspect, the driving and dosing device can have at least one, e.g. exactly one, two or three, discharge springs acting between the propulsion element or a rotation element and the abutment and in particular arranged between them. The at least one spring can be supported on the propulsion element and/or the abutment, for example. The single discharge spring, for example, can be supported at its distal end on the propulsion element, and at its proximal end, on the abutment. In particular, the at least one discharge spring can be arranged inside the guide or the sleeve-shaped housing part forming the guide. If the propulsion element is sleeve-shaped, the at least one discharge spring can be arranged inside the propulsion element. Alternatively, a first discharge spring and a second discharge spring can be arranged kinematically between the propulsion element and the guide or the sleeve-shaped housing part forming the guide. The first discharge spring can surround the second discharge spring, for example, or vice versa. In particular, the second discharge spring can be arranged concentrically with the first discharge spring. The first discharge spring and the second discharge spring can be connected in parallel or in series for example. Springs connected in parallel means in particular that the first and the second discharge springs are each supported at their distal end on the propulsion element and on the abutment at their proximal end. Thereby the spring constants of the first and second discharge springs can be added up to a total spring constant. Springs connected in series means in particular that the distal end of either the first or the second discharge spring is braced against the proximal end of the other of the first and second discharge springs, particularly directly or preferably indirectly, such as via an intermediate element. For example, the first discharge spring can be supported on the abutment and the intermediate element, and the second discharge spring can be supported on the intermediate element and the propulsion element. The distal end of the first discharge spring can be arranged distally from the proximal end of the second discharge spring, for instance. Due to the intermediate element, the spring force of the first spring can be transmitted from its distal end onto the proximal end of the second discharge spring. In particular, the intermediate element can be sleeve-shaped and arranged in an annular gap between the first and second discharge springs. Springs connected in series make it possible to have a spring force that remains equal over a relatively long spring travel.

For example, the at least one discharge spring, more particularly the first and second discharge springs, can be a coil or helical spring that acts as a compression spring or torsion spring. The at least one discharge spring is cocked and acts on the propulsion element in such a manner that it attempts to displace the propulsion element in the distal direction, i.e. discharge direction, relative to the abutment. The at least one discharge spring is cocked with sufficient energy in the delivery state of the driving and dosing device that it can discharge the maximum or total quantity of injectable product in the product container in multiple individual discharges, i.e. in multiple discharges of individual product doses. The driving and dosing device is designed such that the next dose to be discharged is reset after each individual discharge or product dose discharge. In contrast to embodiments in which a discharge spring must be recocked for every dose adjustment, easier dose adjustment can be achieved with the spring cocked to the energy required for discharging the maximum product quantity injectable from the product container, since the dosing element, which is rotatable relative to the housing for setting the dose, is then easier to rotate because the spring does not need to be cocked while adjusting the dose. This increases the convenience of using the device.

The driving and dosing device can additionally comprise a rotation element, the location of which has the effect that the spring outputs energy to the propulsion element, whereby the propulsion element is moved in the distal direction. The rotation element preferably takes on the function of a control element, wherein the rotation of the rotation element by a defined angle of rotation causes the advancement of the propulsion element by a defined discharge stroke. By selectively releasing or blocking rotation of the rotation element relative to the housing, the spring can be allowed to move the propulsion element in the distal direction relative to the abutment, or not to move it. In particular, the rotation element can be coupled to the actuating element such that, upon actuation of the actuating element for a product discharge, the rotation element is released for a rotation relative to the housing in order to discharge the product, and it is blocked from rotation relative to the housing if the actuating element is not actuated. In particular, a clutch that effects the release and locking of rotation of the rotation element relative to the housing can be arranged between the actuating element and the rotation element.

The clutch can advantageously release the rotation of the rotation element relative to the housing if the actuating element is actuated, and can block the rotation of the rotation element relative to the housing when the actuating element is released.

The discharge spring is preferably arranged kinematically between the piston of the product container and the rotation element. In this way, it is possible to prevent the discharging energy provided by the discharge spring from having to run largely via the rotation element as would be the case if the rotation element were arranged kinematically between the discharge spring and the piston. Thereby the rotation element can be designed more simply In particular this can cause the at least one discharge spring to drive the propulsion element and the propulsion element to drive the rotation element. In particular, the propulsion element can be arranged kinematically between the discharge spring and the rotation element.

In particular, the angle of rotation of the rotation element can be proportional to the discharge stroke of the piston or the propulsion element. This can be achieved by selectively blocking or releasing the rotation element.

The rotation element can advantageously be in an engagement, particularly a threaded engagement, with the propulsion element. The thread pitch of this threaded engagement has the effect that in case of a complete revolution of the rotation element relative to the housing, the propulsion element can be displaced by the discharge spring by an amount that corresponds to the thread pitch, for example.

The rotation element can be a threaded rod, for example, and the propulsion element can have or be a threaded nut, wherein the thread of the threaded nut engages with the thread of the threaded rod.

In an alternative example, the rotation element can be a threaded nut and the propulsion element can have or be a threaded rod, wherein the thread of the threaded nut engages with the thread of the threaded rod.

The rotational element is preferably axially fixed in relation to the housing, or can at least be supported axially fixedly in one direction, preferably the distal direction, on the housing or an element fixed to the housing such as the abutment.

It is advantageous that the rotation element is connected rotationally fixedly to the housing during the setting of a dose, i.e. in the non-actuated state, by means of the clutch in particular, and is rotated or rotatable during the actuation of the device to discharge the product dose. The driving and dosing device can have a dose setting or dose indicating device including a housing, a dose indicating element with a dose scale, a pointing device and a dosing element, and advantageously, but not necessarily, may additionally include a bearing element engaged and functionally operable with the dose indicating element as described herein. The dose indicating element, particularly the dose indicating drum, can also fundamentally be in threaded engagement with the housing or an element arranged fixedly relative to the housing.

The dose indicating element, particularly the dose indicating drum, can be rotatable relative to the rotation element during the setting of a dose, i.e. in the non-actuated state of the driving and dosing device or the actuating element. The dose indicating element is preferably rotationally fixed relative to the rotation element during the actuation of the device in order to discharge the product dose and is axially movable, for example, or is rotationally fixedly connected to the rotation element, in particular with the above-described clutch or some other clutch.

This has the advantageous effect that during discharging of the dose, i.e. during actuation of the actuating element, the discharge spring screws the dose indicating element back into its zero dose position, particularly via the rotation element and preferably via a clutch element, which is preferably arranged rotationally fixedly but axially displaceably in relation to the dose indicating element. In particular, the clutch element and the dose indicating element can be in a rotationally fixed engagement that allows an axial movement between the dose indicating element and the clutch element. This engagement can be effected by means of a longitudinal guide, for example. The clutch element is preferably connected axially fixedly but rotatably to the bearing element.

For example, the driving and dosing device can have a first clutch structure that is rotationally fixed in relation to the housing. The rotation element can have or form a second clutch structure that, when in coupling engagement with the first clutch structure, causes the rotation element to be rotationally fixed in relation to the housing. The first clutch structure can be formed by the housing for example, or an element arranged rotationally fixedly but axially displaceably in relation to the housing, such as the bearing element or a clutch element, particularly a sleeve-shaped one.

The clutch element can have a third clutch structure which, when engaged with the first clutch structure or an additional, fourth clutch structure of the rotation element, causes the dose indicating element to be rotationally fixedly coupled to the rotation element. In the non-actuated state of the device, the rotation element and the housing are rotationally fixed to one another; in particular, the first and second clutch structures are engaged, while the third and second or optionally the third and fourth clutch structures are disengaged. In the actuated state, the third and second, and optionally the third and fourth clutch structures are engaged, while the first and second clutch structures are disengaged from one another.

It is particularly advantageous if the dose indicating element is already rotationally fixedly coupled to the rotation element and the rotation element is still rotationally fixedly coupled to the housing while the actuating element is being pushed onto the housing for actuation. This ensures that the dose indicating element is first coupled securely to the rotation element when the rotation element has been released for a rotation relative to the housing. In other words, there is an intermediate position between the actuated and non-actuated position of the actuating element, in which the rotation element is both coupled rotationally fixedly to the housing and also rotationally fixedly to the dose indicating element. In particular, the first and the second and the third and the second clutch structures, and optionally the third and the fourth, can be simultaneously engaged, namely when the actuating element occupies its intermediate position.

In generally preferred embodiments, the dose indicating element can have a stop, such as a zero dose stop, which is moved away from a mating stop, in particular a mating zero dose stop, whenever a dose is increased and is moved toward the mating stop whenever a dose is reduced, or when the device is actuated for discharging the set product dose.

In particular, the dose indicating element can be at least rotationally decoupled from the rotation element during setting of the product dose, i.e. dose increase and dose reduction and, during actuation of the device for discharging the product dose, can be coupled with the rotation element in such a manner that a rotation of the rotation element has the effect of moving the dose indicating element towards the mating stop, i.e. the zero dose stop is moved towards the zero dose mating stop. If the zero dose stop and the zero dose mating stop are stopped or in contact, this prevents, particularly via the clutch, a rotation of the rotation element and thus prevents further advancement of the propulsion element relative to the housing.

Between the dose setting element and the dose indicating element there can be a dosing clutch, which couples the dose setting element to the dose indicating element rotationally fixedly if the driving and dosing device or the actuating element is non-actuated, and rotationally decouples them if the driving and dosing device or the actuating element is actuated. In other words, the dose indicating element and the dosing element are coupled rotationally fixedly via the dosing clutch whenever the actuating element is non-actuated, and the dose indicating element is rotatable relative to the dose setting element whenever the actuating element is actuated. The dosing clutch is opened by actuation of the actuating element.

In advantageous refinements, the driving and dosing device can comprise a mechanism for preventing the setting of a dose that exceeds the quantity of a medication in the product container. In particular, this mechanism can block rotation of the dosing element in a direction that would cause an increase of the dose, more particularly even if the maximum stop of the dose indicating element and the maximum dose mating stop are not yet engaged or if a dose is displayed in the pointing device that is smaller than the maximum adjustable product dose. The mechanism thus prevents setting a dose that exceeds the remaining amount of product contained in the product container, which reduces the danger of misuse of the driving and dosing device. The mechanism can have a limiter, for example, which is positioned between two parts, of which one rotates relative to the other during dose-setting and does not rotate during actuation, i.e. dose discharging. For example, the limiter can be arranged between the dose-setting element, which can be designed in particular as a dose-setting knob or dose-setting sleeve, and the housing or an element fixed in relation to the housing. The limiter, the dose-setting element and the housing can be coupled to one another in such a manner that a relative rotation, particularly during dose-setting, between the dose-setting element and the housing causes the limiter to move to a stop position in which the limiter prevents setting a dose that exceeds the amount of a product in the product container. Examples of appropriately suitable limiters are disclosed in WO 2010/149209 or in WO 01/19434 A1, particularly in FIG. 3 thereof. For example, the limiter can have an internal thread that is engaged with an external thread of the housing. In particular, the limiter can have a longitudinal guide on its outer side by which it is engaged with the dose-setting element such that the dose-setting element is rotationally fixed relative to the limiter. Alternatively, the housing can have the longitudinal guide for the limiter, so that the limiter is rotationally fixed relative to the housing and the limiter can have a thread, particularly an external thread, that engages with a thread, particularly an internal thread, of the dose-setting element.

The stop position is defined by a stop for the limiter, wherein the stop can be formed by the housing or the dose-setting element or a means fixed relative to the housing at least axially or in the circumferential direction. If the limiter and the stop are in contact, a rotation of the dose-setting element in a direction that would cause an increase of the dose is no longer possible or is blocked.

In generally preferred refinements, particularly of the first and second aspects, the driving and dosing device can have at least one signal generation mechanism, which is adapted to generate an acoustic and/or tactile signal, more particularly mechanically, during the dose-setting and/or the product discharging. Such a signal can be perceived as a click signal. For example a (first) signal generation mechanism can be provided, which generates the signal during the dose-setting and can optionally be referred to as a dose-setting signal generation mechanism. In addition, a further (second) signal generation mechanism can be provided, which generates the signal during the product discharging and can optionally be referred to as a product discharge signal generation mechanism. Alternatively, a (common) signal generation mechanism can be provided, which generates a signal during dose-setting and during product discharging.

In general, the signal generation mechanism can be arranged between two parts that move, more particularly rotate, relative to one another during dose-setting and/or product discharging. One of the parts can have a resiliently arranged catch element for example, which engages with a toothing of the other one of the two parts, arranged across the periphery thereof, for example. If one part is moved relative to the other, the catch element can slide over the toothing and generate the signal. The toothing can be formed by an internal periphery or external periphery or an end face of the part.

In particular, the signal generation mechanism can be formed between the clutch element and the bearing element. The clutch element and the bearing element preferably rotate relative to one another during dose-setting and product discharging, whereby a signal generation mechanism is formed that generates the signal during dose-setting and product discharging.

The signal generation mechanism can be formed in particular between the bearing element and the rotation element, wherein what has been explained for the bearing element applies here as well, at least in the present context, for a switching sleeve described herein. The bearing element and the rotation element preferably rotate relative to one another during, more particularly only during, product discharging, whereby a signal generation mechanism is formed that generates a signal during product discharging.

The signal generation mechanism can be formed in particular between the clutch element and the rotation element. The clutch element and the rotation element preferably rotate relative to one another during, more particularly only during, dose-setting, whereby a signal generation mechanism is formed that generates a signal during dose-setting.

BRIEF DESCRIPTION OF THE DRAWINGS

FIGS. 2a-c show the driving and dosing device from FIG. 1 in an initial or delivery state, wherein FIG. 2b is a sectional view of FIG. 2a and FIG. 2c is a sectional view of FIG. 2a rotated by 90° along the line B-B.

FIGS. 3a-c show the injection device in the views from FIG. 2a in a state in which the maximum adjustable dose has been set.

FIGS. 4a-c show the views from FIGS. 2a-c in which the dose set in FIGS. 3a-c has been completely discharged and an actuating element is still being actuated.

FIGS. 5a-c show the views from FIGS. 2a-c, wherein a driving element of the driving and dosing device has been blocked for a movement to increase the dose, because the dose contained in the product container is smaller than the maximum settable dose.

FIG. 6 shows an exploded view of the individual parts of a second embodiment of a driving and dosing device according to the invention.

FIGS. 7a-c show the driving and dosing device from FIG. 6 in an initial or delivery state, wherein FIG. 7b is a sectional view of FIG. 7a and FIG. 7c is a sectional view of FIG. 7a rotated by 90° along the line B-B.

FIGS. 8a-b show an exploded view of the individual parts of a third embodiment of a driving and dosing device according to the invention, wherein FIG. 8b is a sectional view of FIG. 8a.

FIGS. 9a-c show the driving and dosing device from FIGS. 8a and 8b in an initial or delivery state, wherein FIG. 9b is a sectional view of FIG. 9a and FIG. 9c is a sectional view of FIG. 9a rotated by 90° along the line B-B.

FIGS. 10a-b show an exploded view of the individual parts of a fourth embodiment of a driving and dosing device according to the invention, wherein FIG. 10b is a sectional view of FIG. 10a.

FIGS. 11a-c show the driving and dosing device from FIGS. 10a and 10b in an initial or delivery state, wherein FIG. 11b is a sectional view of FIG. 11a and FIG. 11c is a sectional view of FIG. 11a rotated by 90° along the line B-B.

FIG. 12 shows an exploded view of the individual parts of a fifth embodiment of a driving and dosing device according to the invention.

FIGS. 13a-c show the driving and dosing device from FIG. 12 in an initial or delivery state, wherein FIG. 13b is a sectional view of FIG. 13a and FIG. 13c is a sectional view of FIG. 13a rotated by 90° along the line B-B.

FIG. 14 shows an exploded view of the individual parts of a sixth embodiment of a driving and dosing device according to the invention.

FIGS. 15a-c show the driving and dosing device from FIG. 14 in an initial or delivery state, wherein FIG. 15b is a sectional view of FIG. 15a and FIG. 15c is a sectional view of FIG. 15a rotated by 90° along the line B-B.

FIG. 16 shows a modified arrangement of discharge springs.

FIG. 17 shows another modified arrangement of discharge springs.

FIGS. 18a-20b show a seventh embodiment of the driving and dosing device in an initial state, a dose-set state and a discharged state, wherein FIG. 18b is a sectional view of FIG. 18a and FIG. 20b is a sectional view of FIG. 20a.

FIG. 21b shows an alternative for the single part from FIG. 21a.

FIGS. 22a-24b show an eighth embodiment of the driving and dosing device in an initial state, a dose-set state and a discharged state, wherein FIG. 22b is a sectional view of FIG. 22a and FIG. 24b is a sectional view of FIG. 24a.

FIG. 25a shows a single part, i.e. a bearing element, for the device from FIGS. 22a-24b.

FIG. 25b shows an alternative for the single part from FIG. 25a.

FIGS. 26a-28b show a ninth embodiment of the driving and dosing device in an initial state, a dose-set state and a discharged state, wherein FIG. 26b is a sectional view of FIG. 26a and FIG. 28b is a sectional view of FIG. 28a.

FIGS. 30a-32b show a tenth embodiment of the driving and dosing device in an initial state, a dose-set state and a discharged state, wherein FIG. 30b is a sectional view of FIG. 30a and FIG. 32b is a sectional view of FIG. 32a.

FIGS. 34a-36b show an eleventh embodiment of the driving and dosing device in an initial state, a dose-set state and a discharged state, wherein FIG. 34b is a sectional view of FIG. 34a and FIG. 36b is a sectional view of FIG. 36a.

FIG. 37a shows a single part, i.e. a body forming a pointing device, for the device from FIGS. 34a-36b.

FIG. 37b shows a single part, i.e. a bearing element, for the device from FIGS. 34a-36b.

FIGS. 38a-40b show a twelfth embodiment of the driving and dosing device in an initial state, a dose-set state and a discharged state, wherein FIG. 38b is a sectional view of FIG. 38a and FIG. 40b is a sectional view of FIG. 40a.

DETAILED DESCRIPTION

Figure 1:
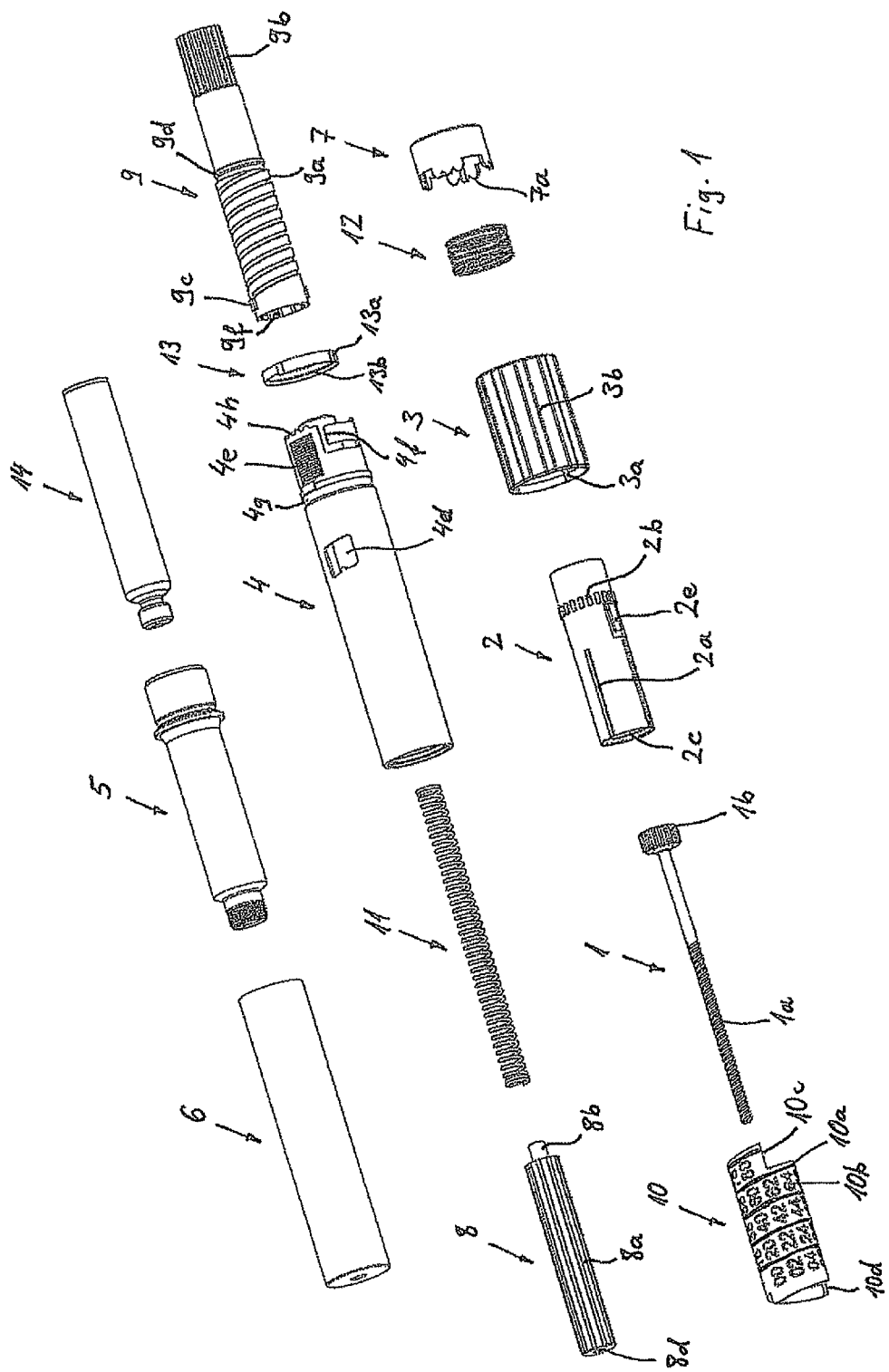
FIG. 1 shows an exploded view of the individual parts of a first embodiment of a driving and dosing device according to the invention.
Figure 8A:
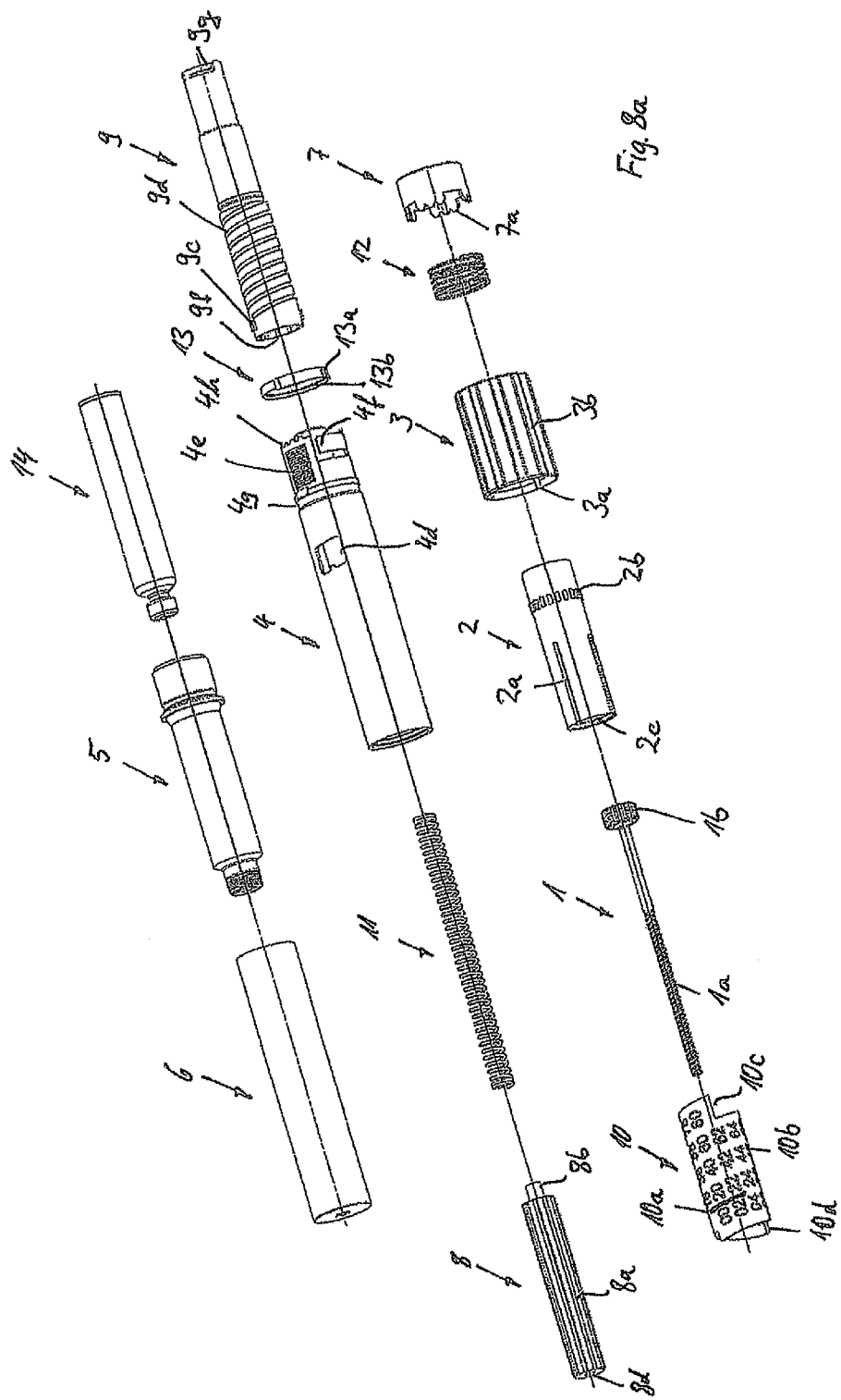
Figure 18A:
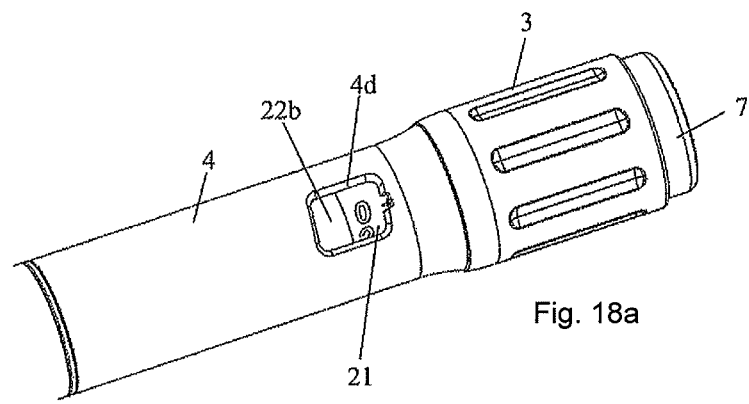
Figure 18B:
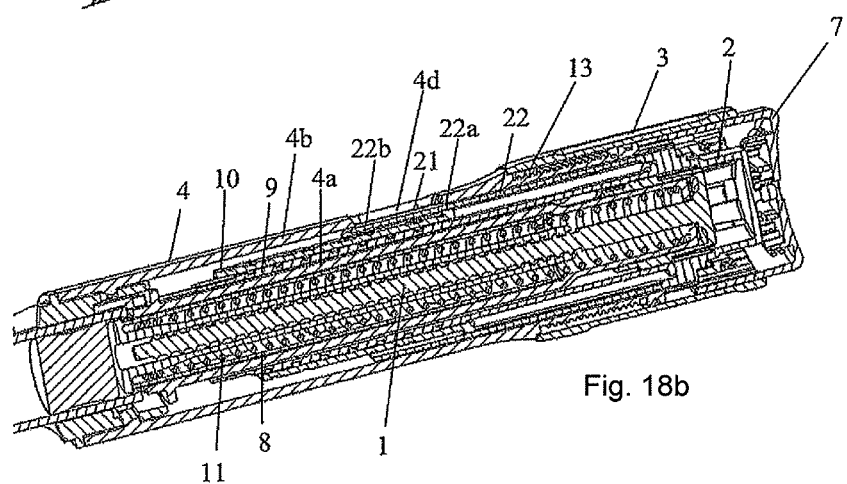

In a first embodiment, as can be seen in FIGS. 1 and 2a-2c, for example, the driving and dosing device comprises a sleeve-like housing 4 that has an outer sleeve 4b that can be gripped by the user with one hand. As can be recognized best from FIG. 2b, the housing 4 further comprises an inner sleeve 4a, which forms an abutment 4i and is arranged concentrically to the outer sleeve 4b. Inner sleeve 4a and outer sleeve 4b are connected to one another via an annular web. Between the outer sleeve 4b and the inner sleeve 4a, an annular gap is formed, in which are arranged a dose indicating element 10, which is formed in particular as a dose indicating drum, i.e. in a sleeve-shape, a bearing element 9, and a clutch element 2, which is sleeve-shaped and can also be referred to more particularly as a display clutch.

At the distal end of the housing 4, a sleeve-shaped product container receptacle 5 made from a preferably transparent material is arranged, in which a product container 14 in the form of a carpule is received. The product container 14 is non-detachably connected to the housing 4 by means of the product receptacle 5, so that the driving and dosing device, together with the product container receptacle 5 and the product container 14, forms a disposable injection device, which is, as a whole, disposable after complete emptying of the product container 14. At its distal end, the product container 14 has a septum 14b, which can be penetrated by a needle that can be positioned at the distal end of the product container 14 or the product container receptacle 5.

A piston 14a is arranged in the product container 14, wherein the product to be discharged is arranged between the septum 14b and the piston 14a. A displacement of the piston 14a in the direction of the septum, or in the distal direction, i.e. the discharging direction, thus effects a discharge of the product contained in the product container 14. Also shown in FIG. 1 is a protective cap 6, which can be placed over the product container receptacle 5 and is removed before injection of a dose.

The housing 4, particularly the inner sleeve 4a, is engaged with a sleeve-shaped propulsion element 8, which can also be referred to as a plunger. The propulsion element 8 is rotationally fixed relative to the housing 4 and is axially displaceable along the longitudinal axis L (FIG. 2a). Between the inner sleeve 4a and the propulsion element 8, a guide is formed by means of a longitudinal rib 8a and at least one longitudinal guide 4c, which prevents a rotation of the propulsion element 8 relative to the housing 4 and allows an axial movement of the propulsion element 8 relative to the housing 4. The longitudinal rib 8a is preferably formed by an outer sleeve of the propulsion element 8. The propulsion element 8 has an inner sleeve 8b, which in this example has an internal thread 8c at its proximal end that engages with an external thread 1a of a rotation element 1 embodied as a threaded rod. The propulsion element 8 is arranged such that its distal end 8d can act on the piston 14a, in particular can press against the piston 14a.

The housing 4, in particular the proximal end of the inner sleeve 4a, forms an abutment 4i for a discharge spring 11, which is supported on the abutment 4i and in the area of the distal end of the propulsion element 8. The spring 11 is supported at its distal end on an annular web of the propulsion element 8, which connects the outer sleeve and the inner sleeve of the propulsion element 8. At its proximal end, the spring 11 is supported on the annular web formed by the housing 4 and protruding inward, which forms the abutment 4i.

The discharge spring 11 is formed as a helical or coil spring, which acts as a compression spring and attempts to press the abutment 4i and the propulsion element 8 apart, i.e. to displace the propulsion element 8 in the distal direction relative to the housing 4. At delivery of the driving and dosing device, i.e. in the initial state thereof, the discharge spring 11 is sufficiently preloaded that the energy stored in it is sufficient to discharge the product contained in the product container 14 substantially completely, in particular with a number of individual discharges, between each of which a new dose setting is made. The advantage of such a strongly preloaded spring is that the spring 11 does not have to be cocked during dose-setting, whereby a strength-saving, i e simpler dose-setting is possible for the user of the device.

The threaded engagement between the propulsion element 8 and the rotation element 1 is sufficiently strong that no self-locking of the threaded engagement occurs, i.e. the rotation element 1 is turnable or rotatable relative to the propulsion element 8 about the longitudinal axis L due to the axial force of the discharge spring 11.

The rotation element 1 is constructed as a threaded rod, which forms the external thread 1a and has an enlarged diameter at its proximal end, more particularly in the shape of a broadened head. Teeth 1b are formed parallel to the longitudinal axis L on the head and act as a second clutch structure, as will be described below. An annular friction surface area with a diameter reduced in comparison to the head is arranged on the head and is in contact with the inward-protruding annular web of the housing 4 that constitutes the abutment 4i. Due to the reduced diameter of the annular friction surface, the point of attack of the resulting friction is shifted closer to the longitudinal axis L, whereby the frictional moment between the rotation element 1 and the housing 4 is reduced.

By rotating the rotation element 1 relative to the housing 4 and the propulsion element 8, the spring 11 can displace the propulsion element 8 by a discharge stroke in the distal direction that is proportional to the angle of rotation of the rotation element 1. By selectively blocking and releasing the rotation element 1, which can be accomplished by actuating an actuation element 7 constructed as an actuating button, the movement of the propulsion element 8 relative to the housing 4, i.e. the discharge stroke of the propulsion element 8, can be controlled in an advantageous manner.

The driving and dosing device further comprises a bearing element 9, which can also be referred to as an indicating drum bearing element and is arranged rotationally fixedly relative to the housing 4 but displaceably along the longitudinal axis L. The bearing element 9 is sleeve-shaped and preferably surrounds the inner sleeve 4a of the housing 4, wherein the outer sleeve 4b in particular surrounds the bearing element 9. The bearing element 9 is engaged with the housing 4, more particularly the inner sleeve 4a, which permits a longitudinal movement of the bearing element 9 relative to the housing 4, but prevents a rotational movement. The engagement can be formed by a longitudinal guide 9f between the bearing element 9 and the inner sleeve 4a.

The bearing element 9 has a thread 9a, in particular an external thread with which a thread 10e, more particularity an internal thread, of the dose indicating element 10 engages. The dose indicating element 10 is screwable relative to the bearing element 9 due to this threaded engagement, which guides the rotational or screwing movement of the dose indicating element 10.

The first embodiment further comprises a signal generation mechanism 2e, 9b that generates an acoustic and/or tactile signal during dose-setting and product discharging. The signal generation mechanism 2e, 9b is arranged between the clutch element 2 and the bearing element 9 and comprises in particular a catch element 2e and a toothing 9b. The bearing element 9 has a toothing 9b extending over the periphery, in particular the outer periphery. The clutch element 2 has the resiliently arranged catch element 2e engaging with the toothing 9b.

At the proximal end of the bearing element 9, the bearing element has the toothing 9b extending over its circumference, the teeth of which are used, for example, for setting discrete dose-proportional angular steps and/or for producing a slight resistance during dose-setting and/or for generating an acoustic and/or tactile signal, e.g. an audible and tangible click during dose-setting and product discharging. Two catch elements 2e, which are resiliently arranged on catch arms and are formed by the clutch element 2, engage with the toothing 9b. The clutch element 2 is connected axially fixedly to the bearing element 9 and rotatably relative to the bearing element 9. For this purpose, the clutch element 2 engages by means of an annular groove 2c with a protrusion 9d extending across the periphery of the bearing element 9. A rotation of the sleeve-shaped clutch element 2 relative to the bearing element 9 causes the catch elements 2e to snap over the toothing 9b and produce the acoustic and/or tactile signal.

The dose indicating element 10 is rotationally fixedly but axially displaceably connected to the clutch element 2, more particularly engaged therewith. This engagement comprises a longitudinal guide 2a, which causes the dose indicating element 10 to be rotationally fixed relative to the clutch element 2, but axially displaceable. Because of the rotationally fixed connection between clutch element 2 and dose indicating element 10, a rotation of the clutch element 2 relative to the bearing element 9 causes the dose indicating element 10 to likewise be rotated and, due to the threaded engagement with the thread 9a, to be screwed along the bearing element 9, in particular, in addition to the clicking sounds produced by the catch elements 2e.

The dose indicating element 10 has a dose scale 10b comprising a plurality of successively arranged scale values, that extends helically, corresponding to the pitch of the thread 10e, over the outer periphery of the dose indicating element. In the example shown, a maximum dose of 80 IU can be set, the scale extending from 0 to 80 with dose values indicated in increments of two.

Likewise corresponding to the pitch of thread 10e, a marking 10a is arranged in a helical shape over the outer periphery of the dose indicating element 10. This marking 10a is used, as will be described below, to indicate whether the device is actuated or not actuated. The marking 10a is an optional device. It can extend along the entire dose scale 10b or only parts or only a single scale value. In particular, it is only visible toward the end of product discharging or in the zero position when the driving and dosing device is actuated.

At its proximal end, for example, the dose indicating element 10 has a stop surface 10c pointing and acting in the circumferential direction, which is referred to as the zero dose stop. At the distal end, opposite the proximal end, the dose indicating element 10 has a stop surface 10d pointing and acting in the circumferential direction, which is referred to as the maximum dose stop.

The dose indicating element 10 can be screwed back and forth on the bearing element 9 between the zero dose position and the maximum dose position. In the zero dose position, the zero dose stop 10c, in cooperation with a zero dose mating stop 4f formed by the housing 4, prevents rotation of the dose indicating element 10 in a first rotational direction, namely the rotational direction that would cause a dose less than zero to be set. In this zero dose position, the dose indicating element 10 is rotatable in the opposite, i.e. second, rotational direction.

In the maximum dose position, shown in FIG. 3a for example, the maximum dose stop 10d, in cooperation with the maximum dose mating stop 9c, which is formed by the bearing element 9, prevents rotation of the dose indicating element 10 in the second rotational direction, which would cause an increase of the dose over the maximum settable value. Rotation in the first rotational direction is possible in the maximum dose position. Although the maximum dose mating stop 9c is formed by the bearing element 9, the maximum dose mating stop 9c can optionally be formed, differing from the present example, by the housing 4. Differing from the example shown, the zero dose mating stop can be formed by the bearing element 9 for example.

The housing 4 has a pointing device 4d in the form of a window, which provides a view of the scale 10b of the dose indicating element 10. A dosing element 3 in the form of a dosing knob is mounted rotatably but axially fixedly on the housing 4. For this purpose, the housing 4 has an annular groove 4g with which an annular shoulder of the dosing element 3 engages. The dosing element 3 has a grip structure 3b across its periphery, which makes it easier for the user of the device to rotate the dosing element 3 relative to the housing 4. In the non-actuated state of the device, a rotation of the dosing element 3 causes a rotation or helical movement of the dose indicating element 10, whereby the desired dose can be set and read out in the pointing device 4d.

An actuating element 7 in the form of an actuating button is arranged on the dosing element 3 and is movable relative to the dosing element 3, in particular along the longitudinal axis L, for actuating the device for product discharging. The actuating element 7 forms the proximal end of the device and can be actuated, in particular displaced relative to the housing 4 and/or the dosing element 3, in an easy manner by the thumb of the hand holding the housing 4. The clutch element 2 is rotatable relative to the actuating element 7, particularly when the dosing clutch 2b, 3c is released, and is axially fixed. The actuating element 7 is preferably snapped together with the clutch element 2 axially fixedly but rotatably.

The driving and dosing device additionally has a reset or clutch spring 12, which is cocked during actuation, more particularly pressing, of the actuating element 7, and which returns the bearing element 9 and/or the actuating element 7 into its non-actuated position when the actuating element 7 is not actuated. Actuating the actuating element 7 causes, in addition to the axial displacement thereof, the axial displacement of the bearing element 9 along the longitudinal axis L. The spring 12 is preferably supported at its distal end on the dosing element 3, and at its proximal end, on the actuating element 7. The spring 12 is preferably a helical spring or a coil spring for example, acting as a compression spring.

The dosing element 3 is rotationally fixed relative to the actuating element 7. The actuating element 7 reaches through an inward-pointing shoulder of the dosing element 3. At the distal end of the preferably pot-shaped actuating element 7, a plurality of teeth are formed, which together form a toothing 7a that, due to the actuation of the actuating element 7, comes into engagement with a toothing 4h formed on the housing 4, particularly at the proximal end of the housing 4, whereby the dosing element 3 is rotationally fixed in relation to the housing 4. The result of this is that setting a dose, i.e. a rotation of the dosing element 3 relative to the housing 4, is not possible, but instead is only possible if the actuating element 7 is non-actuated.

The dosing element 3 forms a clutch structure 3c, more particularly at the inward-protruding shoulder. The clutch structure 3c interacts with a clutch structure 2b on the outer periphery of the clutch element 2 when the actuating element 7 is not actuated. In the non-actuated state of the actuating element 7, the dosing element 3 and the clutch element 2 are rotationally fixed relative to one another due to this clutch engagement. The clutch between the dosing element 3 and the clutch element 2 can also be referred to as a dosing clutch 2b, 3c, which is engaged during dose-setting, i.e. when the actuating element 7 is not actuated, and is disengaged during dose discharging, i.e. when the actuating element 7 is actuated, the clutch transferring torque in the engaged state and not transferring torque in the disengaged state. The dosing clutch 2b, 3c is disengaged or opened by a displacement of the clutch element 2 relative to the housing 4, more particularly by actuation of the actuating element 7.

The proximal end of the bearing element 9 has a first clutch structure 9e on the inner periphery, that is formed by claws or teeth arranged across the periphery that engage with the teeth or claws of the rotation element 1 forming the second clutch structure 1b, more particularly when the actuating element 7 is not actuated. The rotation element 1 is rotationally fixed in relation to the housing 4 by means of this clutch engagement. On the inner periphery of the clutch element 2, there is additionally a third clutch structure 2d, which has a plurality of teeth or claws distributed across the periphery. The third clutch structure 2d is arranged such that, when the actuating element 7 is actuated, the clutch structure comes into a rotationally fixed engagement with the rotation element 1, in particular with the second clutch structure 1b, or alternatively, a fourth clutch structure separate from the second clutch structure 1b, but not shown in this example.

While the actuating element 7 is being pushed for actuation along the longitudinal axis L relative to the dosing element 3, the third clutch structure 2d first comes into engagement with the second clutch structure 1b. By further displacement of the actuating element 7 relative to the dosing element 3, the first clutch structure 9e disengages from the second clutch structure 1b. Before, during or simultaneously with the detachment of the engagement between the first clutch structure 9e and the second clutch structure 1b, the clutch structure 2b disengages from the clutch structure 3c and/or the toothing 7a engages with the teeth 4h.

Particularly due to the fact that the first clutch structure 9e is detached from the second clutch structure 1b, the discharge spring 11 can relax, the rotation element 1 being rotated relative to the housing 4; due to the engagement of the second clutch structure 1b with the third clutch structure 2d, the clutch element 2 and thus also the dose indicating element 10 are rotated relative to the housing 4; thereby the dose indicating element 10 is screwed back into its zero dose position and the propulsion element 8 is displaced, proportionally to the circumferential distance between the zero dose stop 10c and the zero dose mating stop 4f, by a discharge stroke in the distal direction relative to the housing 4. The rotation of the clutch element 2 relative to the bearing element 9 causes the catch elements 2e to snap over the toothing 9b, more particularly in dose-proportional angle steps, and produce the acoustic and/or tactile signal.

The driving and dosing device has a dose limiter 13, in the form of a ring, a ring segment or a nut, having a thread 13b on its inner periphery that engages with a thread 4e arranged on the outer periphery of the housing 4, so that the limiter 13 can be screwed relative to the housing 4. At the outer periphery, the limiter 13 has an engagement element 13a, which engages in a longitudinal guide 3a on the inner periphery of the dosing element 3, so that the dose limiter 13 is rotationally fixed but axially displaceable relative to the dosing element 3. A stop projection, from which the limiter 13 has a distance proportional to the maximum product quantity that can be discharged from the product container 14, is formed on the dosing element 3 or the housing 4. Since the dosing element 3 rotates relative to the housing 4 during dose-setting and is not rotated during a dose discharge, the limiter 13 can form a counting mechanism, which adds to the already discharged individual doses and the currently set dose and correspondingly moves the housing 4 closer and closer to the stop projection of the dosing element 3. A dose increase causes the limiter 13 to be moved toward the stop projection. A dose reduction causes the limiter 13 to be moved away from the stop projection. If the remaining dose indicated in the product container 14 is less than the maximum dose that can be set with the driving and dosing device, the limiter 13 comes into contact with the stop projection, so that a rotation of the dosing element 3 relative to the housing 4 in a rotational direction that would result in an increase of the dose is blocked.

The clutch formed from the first, second and third coupling structures 9e, 1b, 2d, as well as optionally the fourth coupling structure, can also be referred to as a discharge clutch due to its interaction.

FIGS. 2a-2c show the driving and dosing device, which can also be referred to as an injection device, in the initial or delivery state, more particularly the state before first usage. The product dose indicated in the pointing device 4d is 0. Actuation of the actuating element 7 would result in no dose being discharged. The limiter 13 is a distance away from the stop projection that is proportional to the quantity of product contained or injectable in the product container 14, e.g. 300 IU.

To set the product dose, the dose setting element 3 is rotated relative to the housing 4, whereby the coupling element 2 and thus also the dose indicating element 10 are rotated relative to the housing 4 due to the clutch engagement 2b, 3c. In the process, the dose indicating element 10 is guided and screws along the bearing element 9 due to the thread engagement of the thread 10e with the thread 9a. In particular, the distance between the zero dose stop 10c and the zero dose mating stop 4f is increased proportionally to the dose shown in the pointing device 4d. In addition, an audible and tactile signal is generated during rotation on the basis of the snapping of the catch elements 2e over the toothing 9b.

FIGS. 3a-3c show the driving and dosing device in a state in which a maximum settable dose has been set, namely 80 IU in this example, which can be read out in the pointing device 4d. A further increase of the dose is not possible due to the interaction, more particularly the contact, of the maximum dose stop 10d with the maximum dose mating stop 9c. As can best be recognized from FIGS. 3b and 3c, the dose limiter 13 has been advanced or shifted toward the stop projection corresponding to 80 IU.

To discharge the dose shown for the sake of example in FIG. 3a, the actuating element 7 is actuated, more particularly pressed, i.e. displaced in the distal direction relative to the housing 4 and the dosing element 3, whereby the clutch element 2 and the bearing element 9 as well as the dose indicating element 10 are displaced distally relative to the housing 4, more particularly against the force of the coupling or reset spring 12. Because the dose indicating element 10 is displaced axially relative to the housing 4 and the pointing device 4d, the marking 10a shown in FIG. 1 appears in the pointing device 4d (FIG. 4a), whereby the user can read visually that the device has been actuated. The displacement of the dose indicating element 10 relative to the housing 4 and the pointing device 4d moves the marking 10a along the longitudinal axis L from a position in which it is concealed by the housing 4 into a position in which it is shown in the pointing device 4d.

The actuation of the actuating element 7 additionally causes the third clutch structure 2d to engage with the second clutch structure 1b and the first clutch structure 9e to disengage from the second clutch structure 1b, so that the rotation element 1 is no longer rotationally fixed in relation to the housing 4, but is rotatable and is rotationally fixed in relation to the clutch element 2 and the dose indicating element 10. Actuating the actuating element 7 also causes the dosing clutch 2b, 3c to disengage or be opened and the front teeth 7a to engage with the front toothing 4h. In the actuated state of the actuating element 7, the rotation element 1 is rotationally fixed relative to the dose indicating element 10, whereby the rotation element 1 and the dose indicating element 10 can rotate jointly relative to the housing 4. The force on the propulsion element 8 from the energy stored in the discharge spring 11 causes a rotation of the rotation element 1 and the dose indicating element 10 relative to the housing 4 due to the threaded engagement of the propulsion element 8 with the rotation element 1, whereby the dose indicating element 10 is screwed back on the bearing element 9 in the direction of the zero dose position and the dose indicated in the pointing device 4d is counted down. At the same time, the propulsion element 8 is moved by the discharge spring 11 in the distal direction relative to the housing 4 by the discharge stroke, which is proportional to the previously set dose. When the dose indicating element 10 has reached its zero position (FIGS. 4a-4c), the previously set dose or single dose has been discharged. If the user releases the actuating element 7, still shown pressed down in FIGS. 4a-4c, the coupling or reset spring 12 resets the actuating element 7, the clutch element 2, the bearing element 9 and the dose indicating element 10 into the position shown for example in FIG. 2a, wherein the marking 10a again disappears under the housing 4 or is concealed by the housing 4. During resetting, the aforementioned elements are displaced in the proximal direction relative to the housing 4 or the dosing element 3.

During resetting of the device by means of the spring 12, the first clutch structure 9e is engaged with the second clutch structure 1b, and the third clutch structure 2d is disengaged from the second clutch structure 1b. The rotation element 1 is now again rotationally fixed in relation to the housing 4, the dosing element 3 again being rotatable together with the dose indicating element 10 relative to the housing 4 and/or the pointing device 4d and/or the rotation element 1 for another setting of a product dose or single dose. In addition, the front toothings 7a and 4h are released from engagement during resetting and the dosing clutch 2b, 3c is reengaged, whereby the dosing element 3 is rotationally fixed relative to the clutch element 2 and the dose indicating element 10.

FIG. 5a shows the driving and dosing device in the position in which the limiter 13 assumes its stop position, i.e. strikes against the stop projection, whereby the limiter 13 blocks setting to a value that exceeds the residual amount contained in the product container 14. In the example shown, the product container 14 still contains 76 IU, while a maximum of 80 IU could be set with the driving and dosing device. Because the limiter 13 is already in contact with the stop projection at 76 IU, the dosing element 3 is blocked from a rotation in the second direction, which would cause an increase of the dose. Decreasing the dose, however, is possible by turning the dosing element 3 in the first rotational direction.

The dose shown in the pointing device 4d is discharged by actuating the actuating element 7. Since the product container 14 is then completely empty, the entire driving and dosing device, or injection device, is disposed of. This is therefore a disposable injection device. In principle, however, the driving and dosing devices shown herein can also be used in connection with multiple-use injection devices, in which an empty product container 14 is exchanged for a new one.

A second embodiment of a driving and dosing device is shown in FIGS. 6-7c. The features that differ from those of the first embodiment will be described below, and therefore the reader is referred to FIGS. 1-5 in other respects. Identical reference numbers designate parts that are at least functionally equivalent.

The driving and dosing device differs from the embodiment of FIGS. 1-5 particularly in that the discharge spring 11 is a torsion spring.

As can be best recognized from FIGS. 7b and 7c, the housing 4 comprises an inner sleeve 4a that is arranged concentrically with the outer sleeve 4b. Inner sleeve 4a and outer sleeve 4b are connected to one another via an annular web. The housing 4, particularly the annular web, forms an abutment 4i for the distal end of the spring 11.

The propulsion element 8 does not include inner and outer sleeves in this embodiment. The longitudinal rib 8a is preferably formed by the sleeve-shaped propulsion element 8. The propulsion element 8 has an internal thread 8c at its proximal end that engages with the external thread 1a of a rotation element 1 embodied as a threaded rod.

The housing 4, particularly the annular web connecting the outer and inner sleeves 4a and 4b, forms the abutment 4i for the discharge spring 11, which is supported at its proximal end on the abutment 4i, and in the area of the head of the rotation element 1, rotationally fixedly in each case.

The discharge spring 11 is formed as a helical or coil spring, which acts as a torsion spring and attempts to twist the rotation element 1 relative to the housing 4 and thereby indirectly displace the propulsion element 8 in the distal direction relative to the housing 4. At delivery, i.e. in the initial state of the driving and dosing device, the discharge spring 11 is rotationally preloaded sufficiently that the energy stored therein is sufficient to discharge the product contained in the product container 14 substantially completely, in particular with a number of individual discharges, between each of which a new dose setting is made.

The threaded engagement between the propulsion element 8 and the rotation element 1 can be, but need not be, sufficiently large that no self-locking of the threaded engagement occurs. The rotation element 1 is turnable or rotatable relative to the propulsion element 8 about the longitudinal axis L due to the torsional torque of the discharge spring 11.

The spring 12 in this case is preferably supported at its distal end on the rotation element 1, and at its proximal end, preferably on the actuating element 7. The spring 12 is preferably a helical spring or a coil spring for example, acting as a compression spring.

The dosing element 3 is engaged rotationally fixedly with the actuating element 7. The actuating element 7 is displaceable relative to the dosing element in the discharge direction along the longitudinal axis L. The actuating element could 7 optionally also be designed according to one of the other examples, however, although this is not shown.

The catch element 2e is arranged in the illustrated example in the proximal area of the clutch element 2, differing from the example of FIGS. 1-5, where the catch element 2e is arranged approximately centrally. The rotation of the clutch element 2 relative to the bearing element 9, during product discharging and dose-setting for example, causes the catch element 2e to snap over the toothing 9b, more particularly in dose-proportional angle steps, and produce the acoustic and/or tactile signal.

The torque on the rotation element 1 from the energy stored in the discharge spring 11 causes a rotation of the rotation element 1 and the dose indicating element 10 relative to the housing 4, whereby the dose indicating element 10 is screwed back on the bearing element 9 in the direction of the zero dose position and the dose indicated in the pointing device 4d is counted down. At the same time, the propulsion element 8 is moved by the discharge spring 11 in the distal direction relative to the housing 4 by the discharge stroke, which is proportional to the previously set dose. When the dose indicating element 10 has reached its zero position, the previously set dose or single dose has been discharged.

Although a limiter 13 is not shown in FIGS. 6-7c, one can be provided in a manner described herein.

A third embodiment of a driving and dosing device is shown in FIGS. 8a-9c. The features that differ from those of the first embodiment will be described below, and therefore the reader is referred to FIGS. 1-5 in other respects. Identical reference numbers designate parts that are at least functionally equivalent.

The driving and dosing device differs from the first embodiment particularly in that it provides a signal generation mechanism 2e, 1c between clutch element 2 and rotation element 1 for signaling the dose setting, and an additional signal generation element 1b, 9g between the rotation element 1 and the bearing element 9 for signaling product discharging. The signal generation mechanism 2e, 1c comprises in particular the catch element 2e of the clutch sleeve 2 and the internal toothing 1c of the rotation element 1. The signal generation mechanism 9g, 1b comprises in particular the catch element 9g of the bearing element 9 and the toothing, i.e. the clutch structure, 1b of the rotation element 1.

Teeth, which are used as a second clutch structure 1b, are arranged on the outer periphery of the head of rotation element 1, parallel to the longitudinal axis L. On the inner periphery of the head, which is surrounded by the outer periphery, a circumferential internal toothing 1c is arranged, with which at least one catch element 2e of the clutch sleeve 2 engages, preferably at least when the actuation element 7 is not actuated and particularly both when the actuating element 7 is actuated and not actuated.

A rotation of the sleeve-shaped clutch element 2 relative to the rotation element 1, as during dose-setting for example, i.e. rotation of the dose-setting element 3 with a non-actuated actuating element 7, causes the at least one catch element 2e to snap over the internal toothing 1c and generate the acoustic and/or tactile signal during dose-setting.

Particularly at the proximal end of the bearing element 9, there is a catch element 9g that is formed on an elastic catch arm and engages with the second clutch structure 1b, preferably at least with the actuating element 7 actuated, and in particular both with the actuating element 7 actuated and not actuated.

If actuating element 7 is actuated, i.e. if the engagement of the first clutch structure 9e is released by the second clutch structure 1b, the rotation element 1 can rotate relative to the housing 4 and the bearing element 9, whereby the teeth of the second clutch structure 1b snap over the at least one catch element 9g of the bearing element 9 and generate the acoustic and/or tactile signal during product discharging.

A fourth embodiment of a driving and dosing device is shown in FIGS. 10a-11c. The features that differ from those of the first embodiment will be described below, and therefore the reader is referred to FIGS. 1-5 in other respects. Identical reference numbers designate parts that are at least functionally equivalent.

The driving and dosing device differs from the first embodiment particularly in that the bearing element 9, with which the dose indicating element 10 engages by means of a thread, is absent and a signal generation mechanism 2e, 1c between the clutch element 2 and the rotation element 1 for signaling the dose setting, and an additional signal generation element 9g, 1b between the rotation element 1 and a switching sleeve 15 for signaling product discharging, are provided. The signal generation mechanism 2e, 1c comprises in particular the catch element 2e of the clutch element 2 and the internal toothing 1c of the rotation element 1. The signal generation mechanism 9g, 1b comprises in particular the catch element 9g of the switching sleeve 15 and the outer toothing, i.e. the second clutch structure 1b, of the rotation element 1.

The dose indicating element 10 is in threaded engagement with the external thread 9a that is formed on the inner sleeve 4a of the housing 4. The effect of this is that the dose indicating element 10 can be screwed back and forth on the housing 4, but is no longer axially displaceable relative to the housing 4 or the pointing device 4d apart from the screwing movement.

The task of the clutch and the generation of the signal during product discharging are taken on by a switching sleeve 15 instead of the bearing element 9. The switching sleeve 15 is rotationally fixed relative to the housing 4, but is arranged to be displaceable along the longitudinal axis L. The switching sleeve 15 preferably surrounds the inner sleeve 4a of the housing 4, while the clutch sleeve 2 in particular surrounds the switching sleeve 15. The switching sleeve 15 is engaged with the housing 4, more particularly the inner sleeve 4a, which permits a longitudinal movement of the switching sleeve 15 relative to the housing 4, but prevents a rotational movement. The engagement can be formed by a longitudinal guide 9f between the switching sleeve 15 and the inner sleeve 4a.

In particular, the switching sleeve 15 has, at its proximal end, the catch element 9g, which is formed on an elastic catch arm and engages with the second clutch structure 1 b, preferably at least when the actuating element 7 is actuated, and particularly both when the actuating element 7 is actuated and when it is not, and is used for generating an acoustic or tactile signal such as an audible and tactile click during product discharging.

The clutch element 2 is connected axially fixedly to the switching sleeve 15 and rotatably relative to the switching sleeve 15. For this purpose, the clutch element 2 extends around the switching sleeve 15 at the sides thereof pointing in the longitudinal direction by means of at least one projection extending across the inner circumference of the clutch element 2. The switching sleeve 15 is thus—like the bearing element 9—driven along by the displacement of the clutch element 2.

Teeth 1b, which are used as a second clutch structure, are arranged on the outer periphery of the head of rotation element 1, parallel to the longitudinal axis L. On the inner periphery of the head, which is surrounded by the outer periphery, a circumferential internal toothing 1c is arranged, with which at least one catch element 2e of the clutch sleeve 2 engages, preferably at least when the actuation element 7 is not actuated and particularly both when the actuating element 7 is actuated and not actuated.

A rotation of the sleeve-shaped clutch element 2 relative to the rotation element 1, as during dose-setting for example, i.e. rotation of the dose-setting element 3 with a non-actuated actuating element 7, causes the at least one catch element 2e to snap over the internal toothing 1 c and generate the acoustic and/or tactile signal during dose-setting.

If actuating element 7 is actuated, i.e. if the engagement of the first clutch structure 9e with the second clutch structure 1b is released, the rotation element 1 can rotate relative to the housing 4 and the bearing element 9, whereby the teeth of the second clutch structure 1b snap over the at least one catch element 9g of the switching sleeve 15 and generate the acoustic and/or tactile signal during product discharging.

Due to the rotationally fixed connection between clutch element 2 and dose indicating element 10, a rotation of the clutch element 2 relative to the switching sleeve 15 causes the dose indicating element 10 to likewise be rotated and, due to the threaded engagement with the thread 9a, to be screwed along the inner sleeve 4a, in particular, in addition to the clicking sounds produced by the catch elements 2e.

Actuating the actuating element 7 causes, in addition to the axial displacement thereof relative to the dosing element 3, the axial displacement of the switching sleeve 15 along the longitudinal axis L. The spring 12 is preferably supported at its distal end on the dosing element 3, and at its proximal end, on the actuating element 7. The spring 12 is preferably a helical spring or a coil spring for example, acting as a compression spring.

A fifth embodiment of a driving and dosing device is shown in FIGS. 12-13c. The features that differ from those of the first embodiment will be described below, and therefore the reader is referred to FIGS. 1-5 in other respects. Identical reference numbers designate parts that are at least functionally equivalent.

The embodiment from FIGS. 12-13c differs from the first embodiment particularly in that the rotation element 1 has a threaded nut, the propulsion element 8 has or is a threaded rod 8e, a signal generation mechanism 2e, 1b for signaling the dose-setting is arranged between the clutch element 2 and the rotation element 1, and an additional signal generation mechanism 1d, 9h, for signaling the discharging of product, is arranged between the rotation element 1 and the bearing element 9. In addition, the limiter 13 is designed somewhat differently and the spring 12 is supported at its proximal end on the clutch element 2, and at its distal end, on the rotation element 1. The signal generation mechanism 2e, 1b comprises in particular the catch element 2e of the clutch element 2 and the toothing, i.e. the second clutch structure 1b, of the rotation element 1. The signal generation mechanism 1d, 9h comprises in particular the catch element 1 d of the rotation element 1 and the internal toothing 9h of the bearing element 9.

The housing 4, particularly the inner sleeve 4a, is engaged rotationally fixedly with a propulsion element 8, which can also be referred to as a plunger. The propulsion element 8 has a threaded rod 8e, which in this example has an external thread that engages in an internal thread of the rotation element 1 embodied as a threaded nut.

The spring 11 is supported at its distal end on an annular web of the propulsion element 8, which connects the threaded rod 8e and the outer sleeve of the propulsion element 8. At its proximal end, the spring 11 is supported on the annular web formed by the housing 4 and protruding inward, which forms the abutment 4i.

The rotation element 1 is formed as a threaded nut, which forms the internal thread, and has teeth serving as the second clutch structure 1b across its outer periphery parallel to the longitudinal axis L. An annular friction surface area with a reduced inner diameter is arranged at the distal end of the rotation element 1 and is in contact with the inward-protruding annular web of the housing 4 that constitutes the abutment 4i. Due to the reduced diameter of the annular friction surface, the point of attack of the resulting friction is shifted closer to the longitudinal axis L, whereby the frictional moment between the rotation element 1 and the housing 4 is reduced.

The clutch element 2 has a catch element 2e, which engages with a toothing, more particularly the clutch structure 1b, formed across the periphery of the rotation element 1. A rotation of the sleeve-shaped clutch element 2 relative to the rotation element 1 causes the catch elements 2e to snap over the second clutch structure 1b and produce the acoustic and/or tactile signal.

At the distal end of the rotation element 1, or distally of the clutch structure 1b, the rotation element has the catch element 1d, which engages with the toothing 9h formed across the inner periphery of the bearing element 9. The rotation of the rotation element 1 relative to the bearing element 9 causes the catch element 1d to snap over the toothing 9h and produce the acoustic and/or tactile signal during discharging of the product.

The bearing element 9 has an annular protrusion 9d extended across the periphery at the proximal end of the bearing element. The clutch element 2 is connected axially fixedly to the bearing element 9 and rotatably relative to the bearing element 9. For this purpose, the clutch element 2 engages with the protrusion 9d by means of an annular groove 2c.

The actuation element 7 is freely rotatable or rotationally fixed relative to the dosing element 3, but is at least axially displaceable. A rotary bearing, which in the present example is formed by an approximately point-like contact surface arranged on the axis of rotation L of the clutch element 2, is formed between the actuation element 7 and the clutch element 2. Alternatively, a sliding bearing in the form of a sliding ring, made of Teflon for example, or a rolling bearing such as an axial ball bearing can serve as the rotary bearing.

The dose limiter 13, in the form of a ring in this example, has an external thread 13c that engages with an internal thread 41 of the housing 4, and on its internal periphery, has an engagement element 13a, which has a torsion-proof engagement with a longitudinal guide 3a of the dosing element 3. In this way the limiter 13 is screwable by rotating the dosing element 3 relative to the housing 4. The internal thread 41 of the housing 4 is formed by an inner limiter sleeve 4j connected rotationally-fixedly and axially fixedly to the outer sleeve 4b via connecting webs 4k. The longitudinal guide 3a is formed on the outer periphery of a dosing element inner sleeve, which is connected axially fixedly and rotationally fixedly to the outer sleeve of the dosing element 3, which can be gripped by the user. The inner sleeve of the dosing element 3 is arranged inside the inner limiter sleeve 4j, the limiter 13 being arranged between the inner sleeve of the dosing element 3 and the inner limiter sleeve 4j.

The sixth embodiment shown in FIGS. 14-15c corresponds substantially to the fifth embodiment, the signal generation mechanism 2e, 9b being constructed in principle as in the first embodiment. The signal generation mechanism 2e, 9b for signaling dose-setting and product discharging is arranged between the clutch element 2 and the bearing element 9 and comprises in particular the catch element 2e and the toothing 9b. The bearing element 9 has the toothing 9b extending over the periphery. The clutch element 2 has the catch element 2e engaging with the toothing 9b.

FIG. 16 presents a modification of the embodiments described herein that has two discharge springs 11a, 11b acting as compression springs, which are connected in series. The first discharge spring 11a is supported at its distal end on the propulsion element 8, and at its proximal end, on an intermediate element 11c. The second discharge spring 11b is supported at its distal end on the intermediate element 11c, and at its proximal end, on the abutment 4i. The second discharge spring 11b is concentric with and arranged inside the first discharge spring 11a. The sleeve-shaped intermediate element 11c, which forms in particular a support surface for the second injection spring 11b at the distal end of the intermediate element and a support surface for the first injection spring 11a at the proximal end of the intermediate element, is arranged between the first discharge spring 11a and the second discharge spring 11b.

FIG. 17 shows a modification of the embodiments described herein that comprises two discharge springs 11a and 11b acting as compression springs, which are connected in parallel. The first discharge spring 11a and the second discharge spring 11b are supported at their distal end on the propulsion element 8, and at their proximal ends on the abutment 4i. The second discharge spring 11b is concentric with and arranged inside the first discharge spring 11a. The sleeve-shaped intermediate element 11c, which prevents the two discharge springs 11a, 11b from becoming entangled with one another, is arranged between the first discharge spring 11a and the second discharge spring 11b.

The seventh through twelfth embodiments shown in FIGS. 18a-41b each represent a modification of the dose indicator for any of the embodiments of a driving and dosing device mentioned herein. Identical reference numbers refer to parts that are identical or at least functionally equivalent. For easier understanding, the dose indicators from the seventh through twelfth embodiments will be described on the basis of an embodiment similar to the first embodiment, so that this will be additionally referred to. In principle, any of the other of the embodiments mentioned herein could be modified with the dose indicators described herein.

The seventh through twelfth embodiments have substantially in common the fact that the pointing device 21 is connected to the actuating element 7, more particularly the actuating button that is formed at the proximal and of the device, in such a manner that the pointing device 21 is pushed along the longitudinal axis L relative to the housing 4 by actuating the actuating button 7. In general terms, the bearing element 9 is displaceable relative to the housing 4 and along the longitudinal axis L together with the dose indicating element 10 and the pointing device 21. That is to say, when the actuating element 7 is actuated, the bearing element 9 is displaced together with the dose indicating element 10 and the pointing device 21 relative to the housing along 4 the longitudinal axis L.

The housing 4, particularly the outer housing sleeve 4b, has a window 4d that enables a view of the pointing device 21 from the outside. The pointing device 21, together with the dose indicating element 10, is displaced in the window 4d along the longitudinal axis L by pressing and releasing the actuating button 7. The user of the device thus perceives a displacement of the dose scale 10b in the window 4d, but no displacement between the pointing device 21 and the dose scale 10b. The user can read out the set dose displayed in the pointing device 21 through the window 4d, as was already described in detail.

In the seventh through eleventh embodiments, the pointing device 21 is formed by a body 20 that is arranged between the housing 4, particularly the outer housing sleeve 4b or the window 4d of the housing 4, and the dose indicating element 10. The pointing device 21 is designed such that it allows a view of the dose indicating element 10 from the outside. The body 20 that forms the pointing device 21 has an opaque region 22a, 22b that adjoins the pointing device 21 proximally or distally. The pointing device 21 itself can be a window-like opening or a window made from a transparent material. The opaque region 22a, 22b can surround the alternative.

In the seventh embodiment, the pointing device 21 is formed by the clutch element 2. The clutch element 2 is engaged with the dose indicating element 10 in such a manner that the dose indicating element 10 is rotationally fixed relative to the clutch element 2 but is axially displaceable. The dose indicating element 10 has a groove that extends parallel to the longitudinal axis L and with which the clutch element 2 engages. The sleeve-shaped clutch element 2 surrounds the dose indicating drum 10, at least in certain portions.

The bearing element 9 is engaged with the clutch element 2 in such a manner that it is axially fixed relative to the clutch element 2 and the clutch element 2 is rotatable relative to the bearing element 9. The bearing element 9 itself is secured against torsion (i.e., rotation) and is axially guided movably on the housing 4.

Figure 21B:
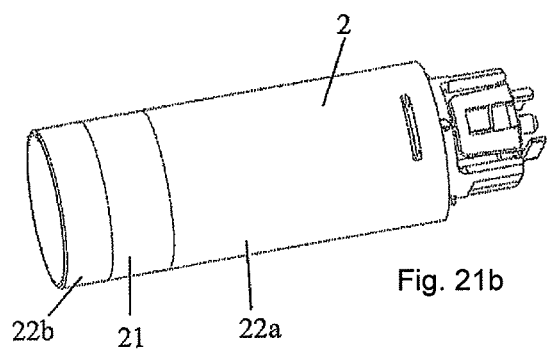
Figure 21A:
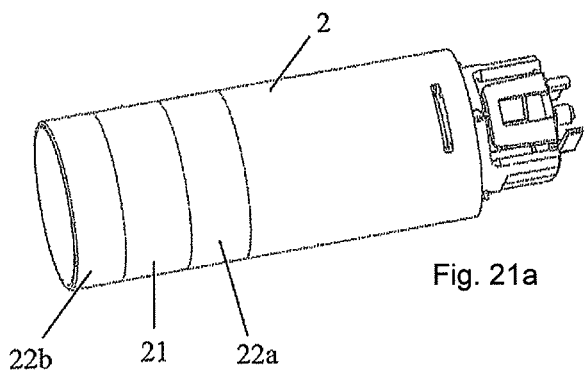
FIG. 21a shows a single part, i.e. a clutch element, for the device from FIGS. 18a-20b.
Figure 22A:
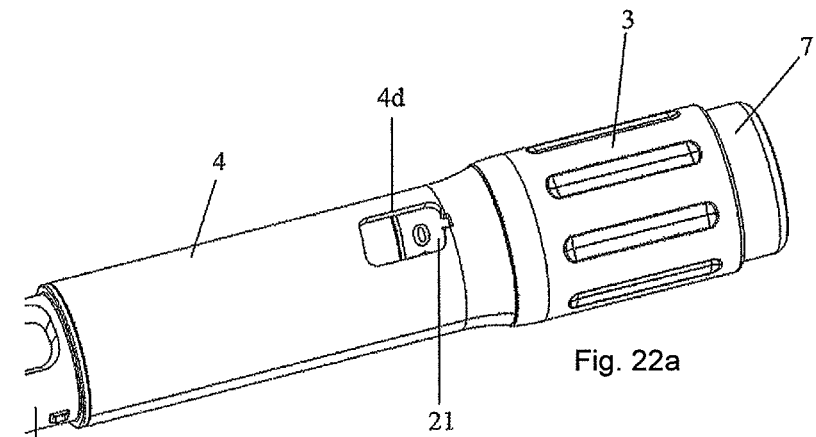
Figure 22B:
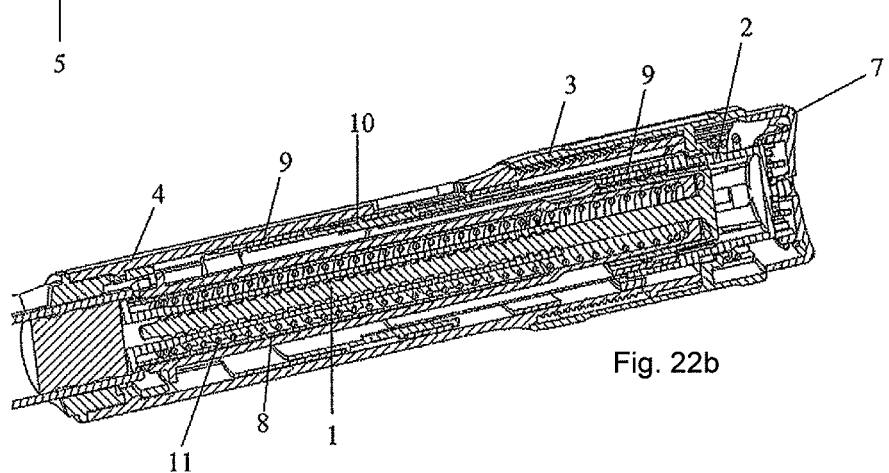

In the variant of the clutch element 2 shown in FIG. 21a, the clutch element is formed from a transparent, particularly completely transparent, material. Opaque portions 22a, 22b, which extend in an annular shape across the periphery of the clutch element 2, adjoin the pointing device 21 distally and proximally. The pointing device 21 likewise extends in an annular shape across the periphery. The opaque regions 22a, 22b are formed by processing the transparent material of the clutch element 2, such as by printing an opaque material as in this example.

In the variant from FIG. 21b, the clutch element 2 is formed from an opaque material, particularly plastic, wherein the annular pointing device 21 extending over the periphery is formed from a transparent plastic. The transparent region 21 can be overmolded or molded on during the original formation (injection molding) of the clutch element 2, for example. The distal and proximal adjoining regions 22a, 22b can be formed from the opaque plastic. At least one of these regions is formed from opaque plastic. The other region can likewise be formed from an opaque plastic or by subsequent processing of the transparent plastic, e.g. by printing. For example, the region 22a can consist of an opaque plastic, while the region 22b can be produced by printing an opaque material onto the transparent plastic forming the pointing device 21.

Figure 19:
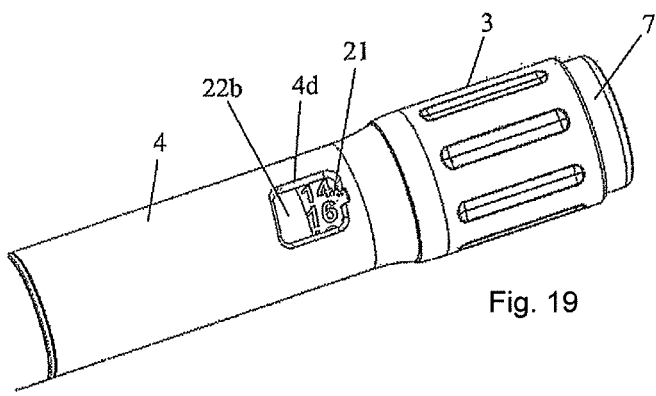
Figure 20A:
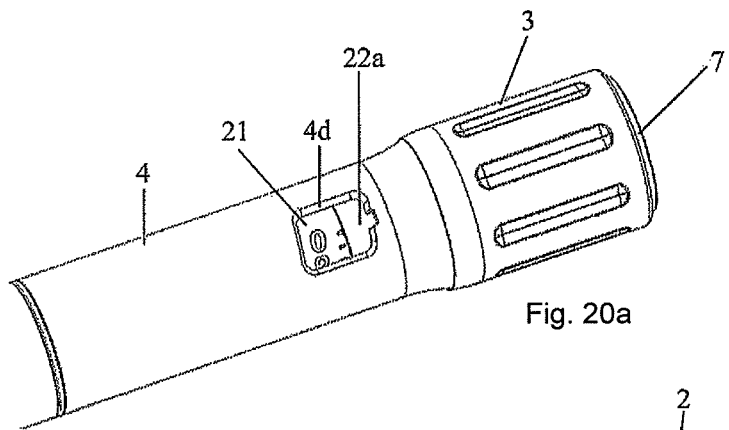
Figure 20B:
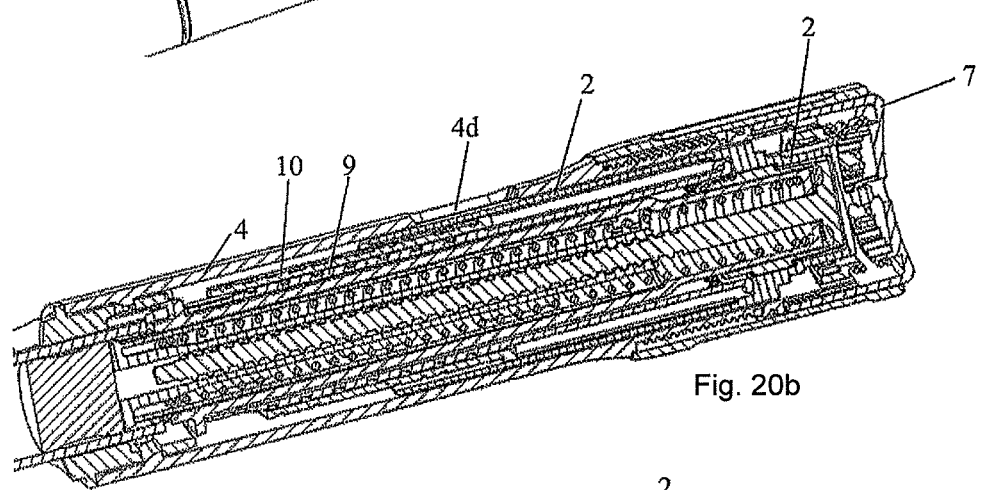

To set the desired product dose, the user of the device turns the dosing element 3 from the initial position (FIGS. 18a, 18b) relative to the housing 4 until the desired dose, e.g. 15 IU, has been set (FIG. 19). During this time, at least the distal opaque region 22b is visible in the window 4d.

To discharge the set product dose, the user actuates the actuating element 7, more particularly by pressing. Thereby the clutch element 2, together with the bearing element 9 and the dose indicating element 10, is displaced relative to the housing 4 and particularly relative to the window 4d. The pointing device 10 is therefore also displaced relative to the housing 4d. Thus the proximal opaque region 22a is recognizable in the window 4d. In general terms, particularly for the seventh through eleventh embodiments, the window 4d is dimensioned such that at least one of the opaque regions, proximal opaque region 22a and distal opaque region 22b, is visible in the window 4d in every position of the actuating element 7.

The proximal and distal opaque regions 22a, 22b, which act like a screen, prevent additional numbers on the dose scale 10b of the dose indicating element 10 from appearing in the window 4d when the actuating element 7 is being actuated and/or is not actuated. Optionally, at least one of the regions 22a and 22b, particularly the proximal opaque region 22a, can have the marking described herein.

In the seventh embodiment, the body 20 forming the pointing device 21 is formed by the clutch element 2.

In the eighth embodiment, which is shown in FIGS. 22a-25b, the body 20 forming the pointing device 21 is formed by the bearing element 9. Bearing element 9 and body 20 form a monolithic component. Between the portion forming the body 20 and a cylindrical portion of the bearing element 9, a gap is formed, in which the dose indicating element 10, i.e. the wall thereof, is arranged. The bearing element 9 surrounds the dose indicating element 10 at the inner periphery and at least in part at the outer periphery. The portion forming the body 20 is connected to the cylindrical portion of the bearing element 9 via a radial web, which is arranged distally from the dose indicating element 10.

The dose indicating element 10 is in a threaded engagement with the bearing element 9. Although the dose indicating element 10 can in principle engage with an internal thread of the bearing element 9, in preferred embodiments the body 20, forms an internal thread that is engaged with an external thread of the dose indicating element 10 (FIGS. 25a, 25b). The dose indicating element 10 can thus be screwed back and forth on the bearing element 9 or the body 20.

The pointing element 21 is a window-like opening through the body 20. The pointing device 21 is arranged between a proximal opaque portion 22a and a distal opaque portion 22b of the body 20.

In the embodiment from FIG. 25a, the pointing device 21, more particularly the window of the body 20, is formed such that at least one and preferably several of the thread courses of the external thread of the dose indicating element 10 are visible through the pointing device 21.

In the embodiment of the bearing element 9 from FIG. 25b, the window 21 of the body 20 is designed such that the thread courses of the dose indicating element 10 are concealed, i.e. cannot be seen.

The bearing element 9 is axially fixedly and rotatably connected to the clutch element 2 in a manner known from the present application. The bearing element 9 is rotationally fixed and is axially guided movably on the housing 4. The clutch element 2 is rotationally fixedly but axially displaceably connected to the dose indicating element 10.

Figure 23:
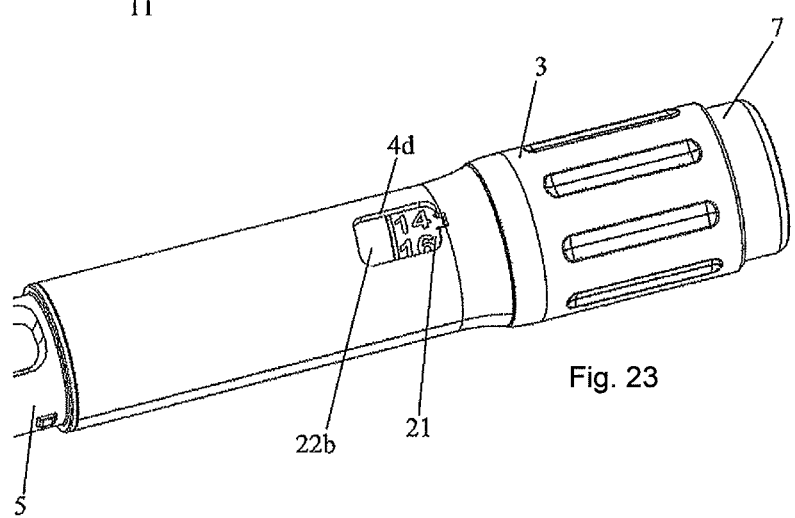
Figure 26A:
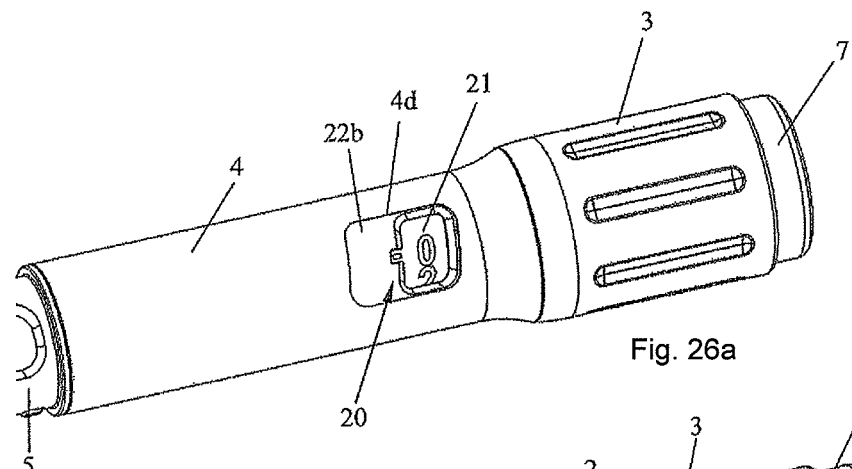
Figure 26B:
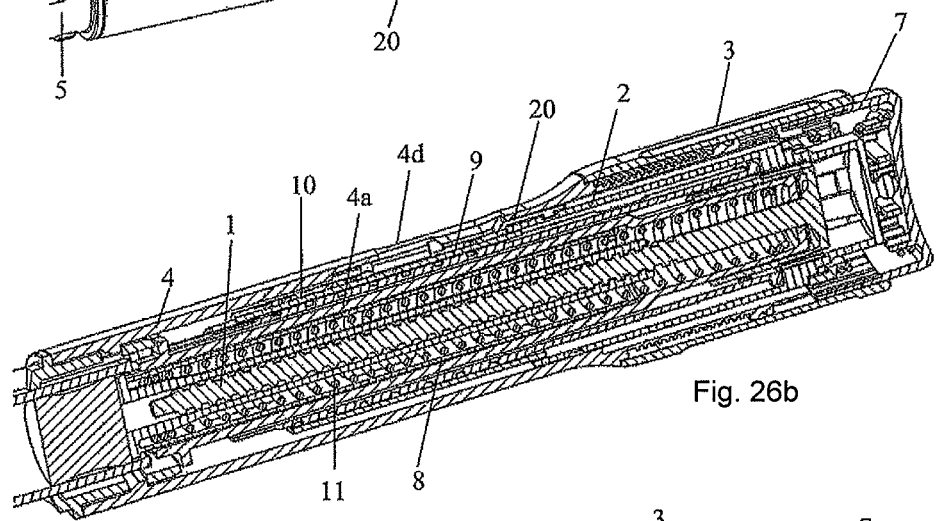

By rotating the dosing element 3 out of the initial position (FIGS. 22, 22b) relative to the housing 4, the desired dose is set and can be read out in the window 4d and in the pointing device 21 (FIG. 23). By rotating the dosing element 3 relative to the housing 4, the dose indicating element 10 is screwed along the bearing element 9.

Actuating the actuating element 7 displaces the clutch element 2, together with the bearing element 9 and the dose indicating element 10, along the longitudinal axis L, whereby the pointing device 21 is displaced relative to the housing 4.

Figure 28A:
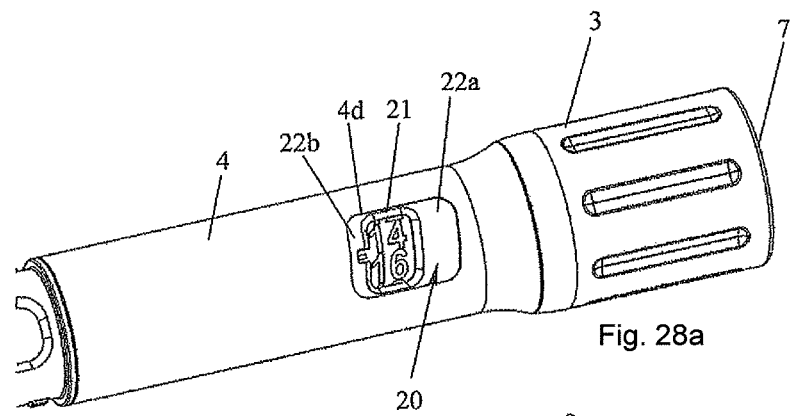
Figure 28B:
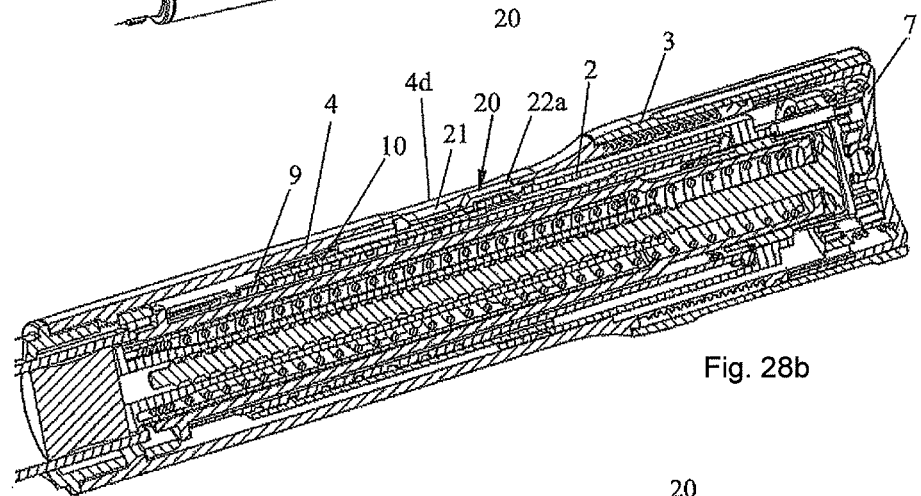
Figure 29:
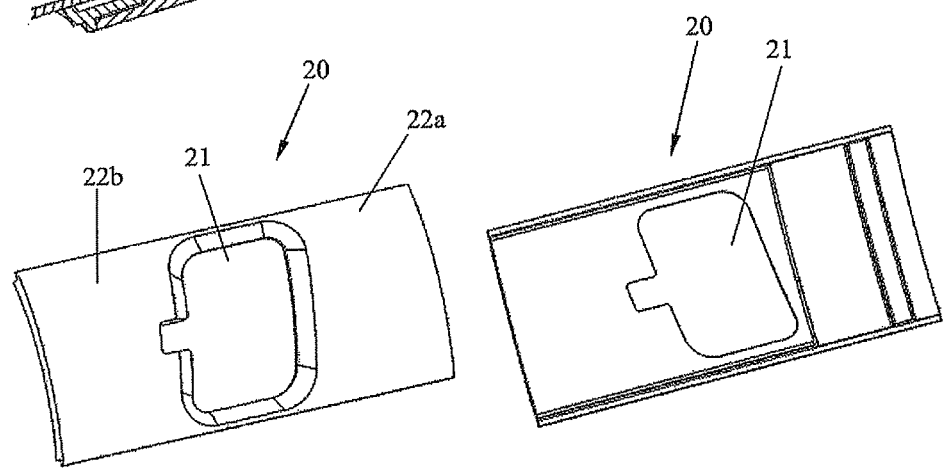
FIG. 29 shows various views of a single part, i.e. a body forming the pointing device, for the device from FIGS. 26a-28b.
Figure 30A:
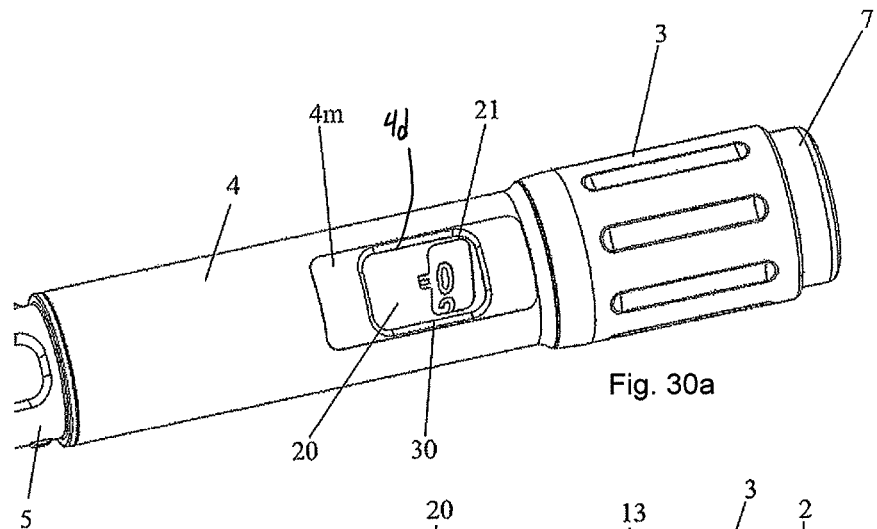
Figure 30B:
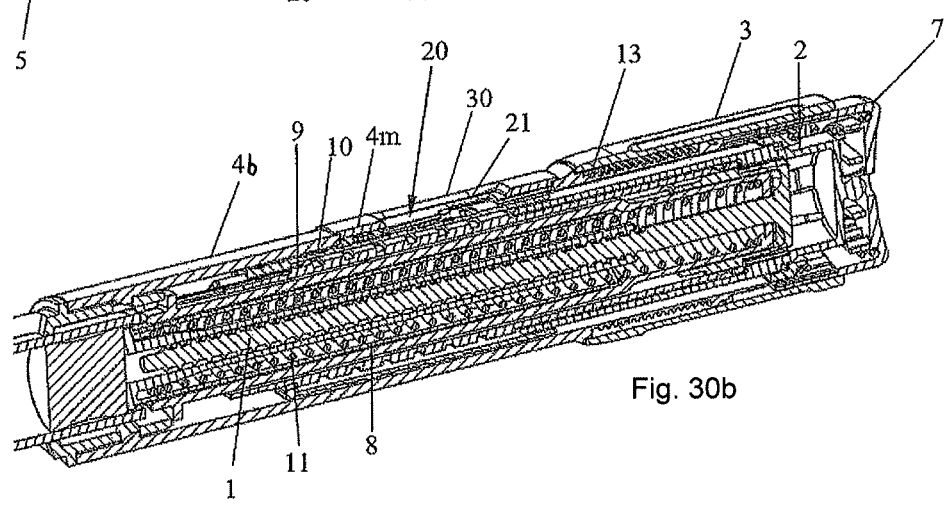
Figure 31:
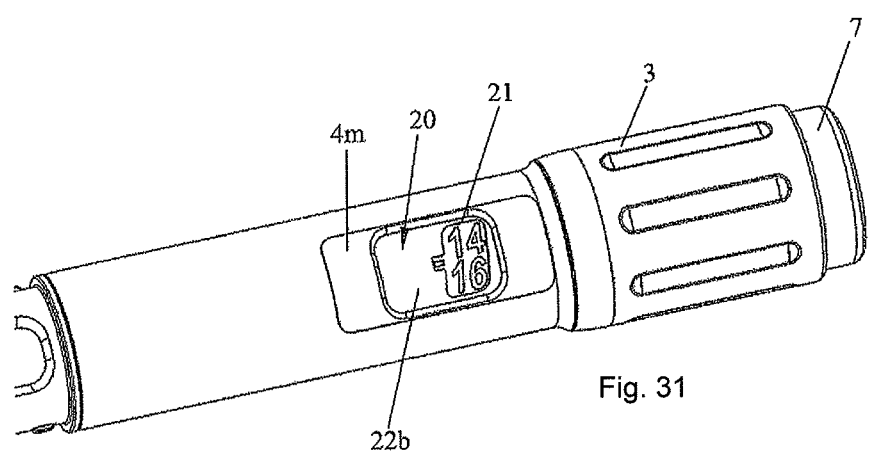

In the ninth embodiment, shown in FIGS. 26a-29, the body 20 forming the pointing device 21 is formed by a part separate from the bearing element 9 (FIG. 29). The body 20 is guided by the housing 4, particularly the outer housing sleeve 4b, particularly on the inner periphery thereof, rotationally fixedly in relation to the longitudinal axis L and displaceably along the longitudinal axis L. The body 20 therefore forms a slider.

A guide, with which the side edges of the body 20 extending parallel to the longitudinal direction L are engaged, is formed on the inner periphery of the outer housing sleeve 4b.

The body 20 is shell-shaped and extends only in portions over the periphery of the outer sleeve 4b of the housing 4.

The body 20 has a pointing device 21, likewise in the form described herein, particularly in the form of a window. Opaque regions 22a, 22b are arranged distally and proximally from the window 21.

The clutch element 2 and the body 20 are engaged in such a manner that the clutch element 2 is axially fixed and rotatable in relation to the body 20. For this purpose, the body 20 has an annular web on its inner side, which engages in an annular groove on the outer periphery of the clutch element 2. Alternatively, the body 20 can have an annular groove portion and the clutch element 2 can have an annular web on its outer periphery that engages with the annular groove.

Figure 27:
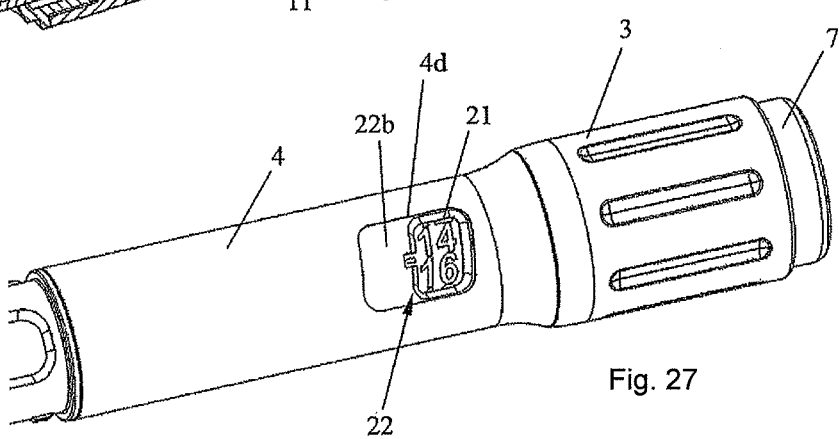

To set the desired product dose, the dose-setting element 3 is rotated out of the initial position (FIGS. 26a, 26b) in relation to the housing 4 until the desired dose can be read out in the pointing device 21 (FIG. 27). Rotating the dosing element 3 in relation to the housing 4 rotates the clutch element 2 relative to the housing 4 and the body 20, wherein the dose indicating element 10, which has a threaded engagement with the bearing element 9, is also rotated by the clutch element 2, whereby the dose indicating element 10 is moved along the bearing element 9.

By actuating the actuating element 7, the clutch element 2 is displaced, which carries along the bearing element 9 and the body 20. The dose indicating element 10 is also displaced together with the bearing element 9 (FIGS. 28a, 28b).

In the tenth embodiment, from FIGS. 30a-33, the outer housing sleeve 4b comprises a portion in which a housing insert 4m is inserted that guides the body 20 forming the pointing device 21 secured against torsion (e.g., rotation) and along the longitudinal axis L. The insert 4m has the window 4d that provides a view of the pointing device 21. The housing insert 4m has two longitudinal guides 4n, which guide the shell-shaped body 20 longitudinally displaceably on its lateral edges. The guides 4n each reach around a lateral edge of the body 20. The cutout in the outer housing sleeve 4b is matched to the insert 4m in such a manner that the insert 4m can be inserted from the exterior into the cutout 1. The insert 4m can be glued or welded to the outer housing sleeve 4b, or preferably snapped into place.

The body 20, which extends only partially over the inner periphery of the outer housing sleeve 4b, has a web-shaped threaded portion 4p on its inner periphery, which engages with an external thread of the dose indicating element 10. The dose indicating element 10 further comprises an internal thread 10e, with which it engages with an external thread 9a of the bearing element 9. The external thread 9a of the bearing element 9 and the internal thread 10e of the dose indicating element 10 have the same thread pitch. The fact that the thread pitches are the same has the effect that the body 20 does not shift in relation to the housing 4 or the housing insert 4m when the dose-setting element 3 is rotated out of its initial position (FIGS. 30a, 30b) relative to the housing 4 (FIG. 31) in order to set the desired dose. During the dose-setting, the dose indicating element 10 screws along the bearing element 9 and the body 20. The clutch element 2 and the dose indicating element 10 are engaged rotationally fixedly but axially displaceably with one another. The clutch element 2 and the bearing element 9 are connected rotatably and axial fixedly to one another.

Figure 32A:
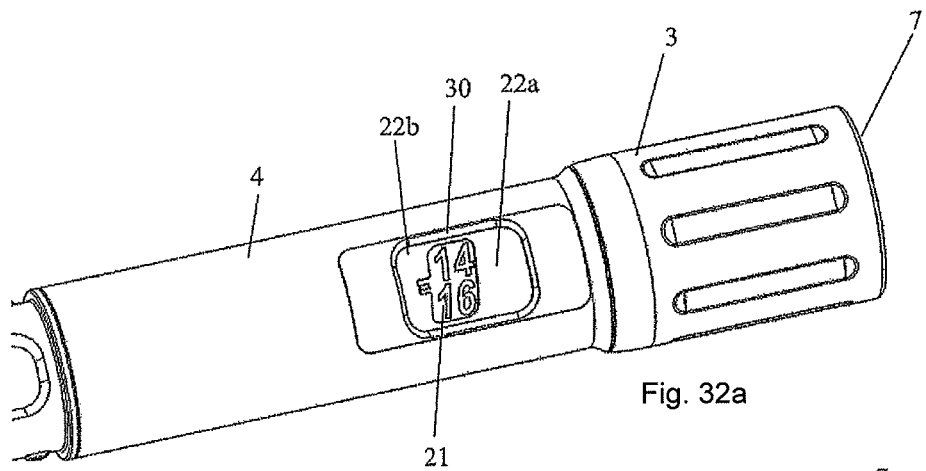
Figure 32B:
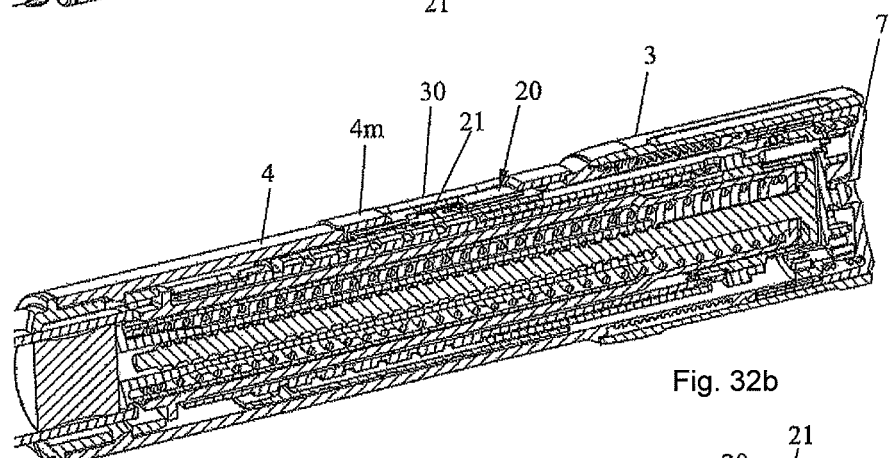
Figure 33:
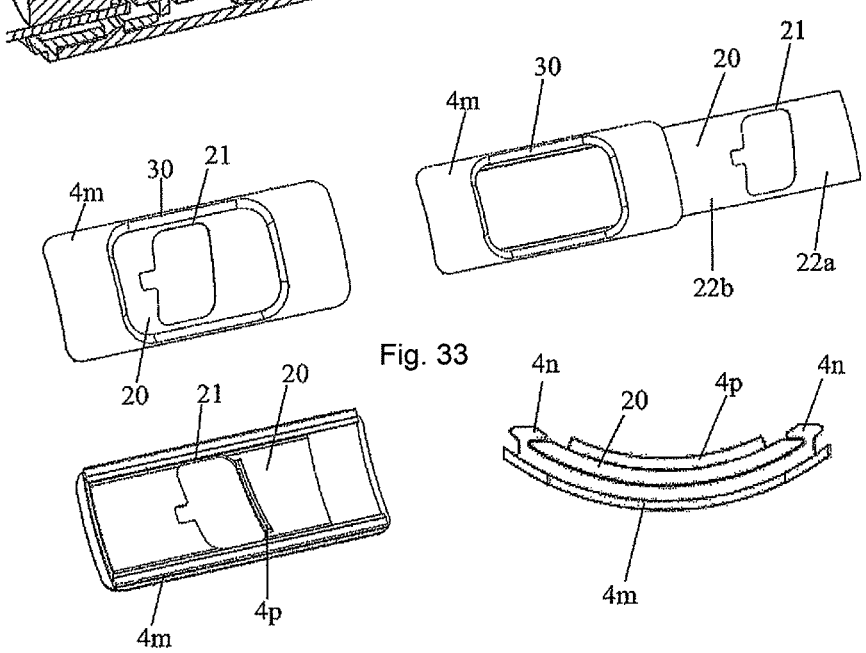
FIG. 33 shows various views of a housing insert with a body displaceably received therein for forming a pointing device.
Figure 34A:
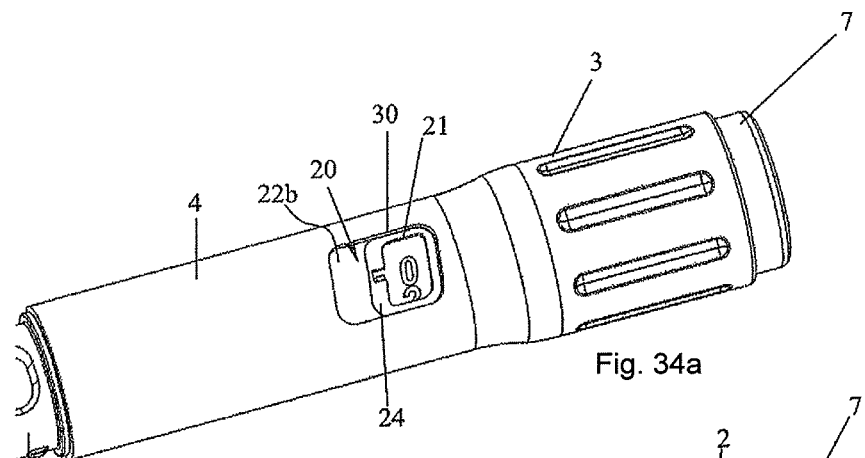
Figure 34B:
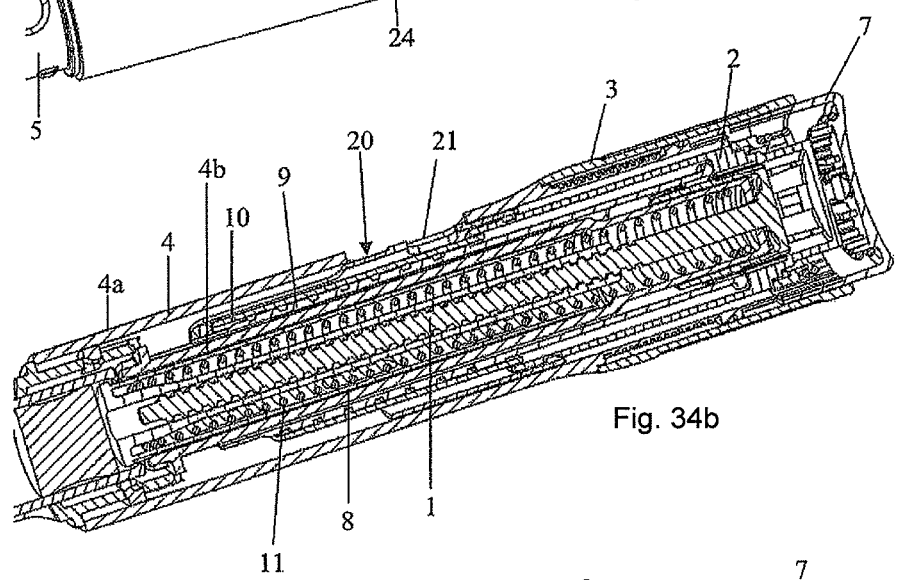
Figure 35:
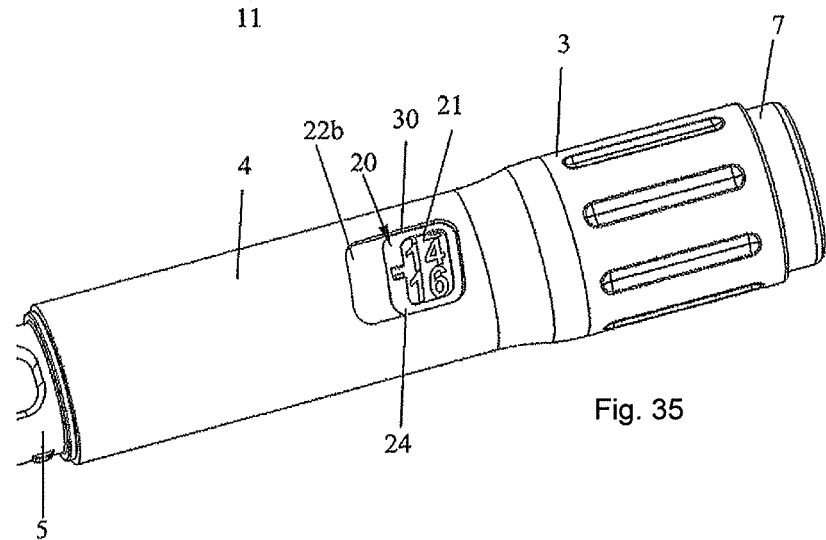
Figure 40A:
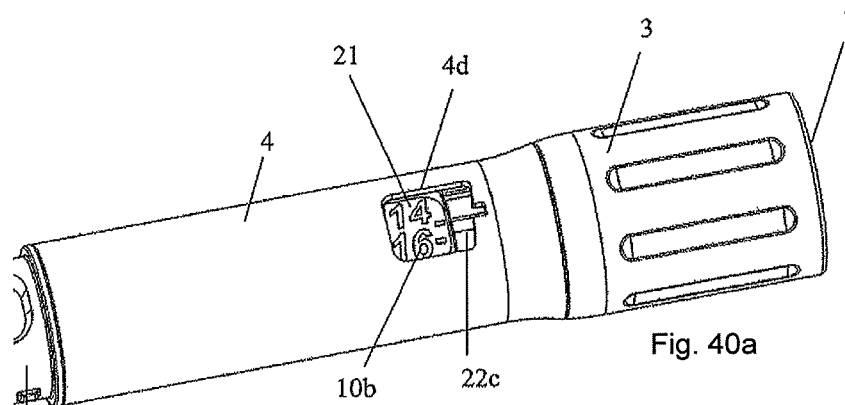
Figure 40B:
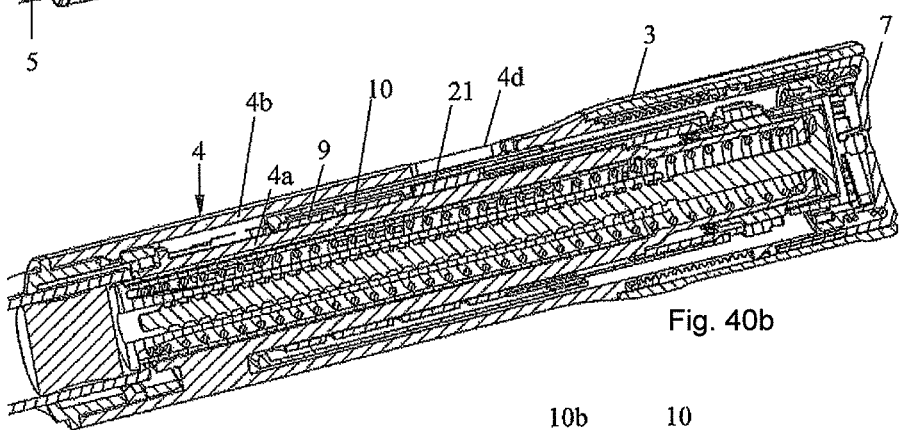
Figure 41A:
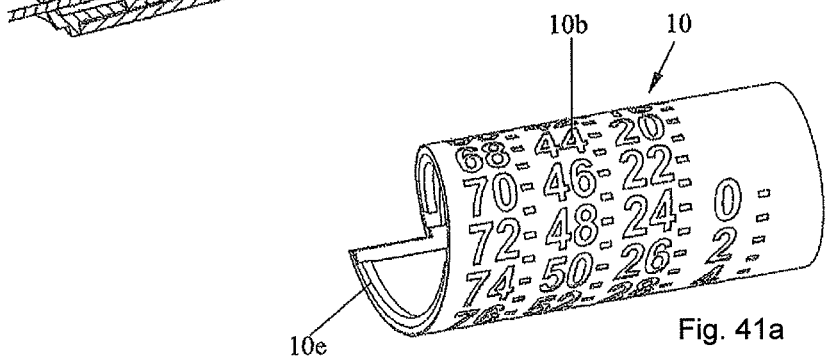
FIG. 41a shows a single part, i.e. a dose indicating element, for the device from FIGS. 38a-40b.
Figure 41B:
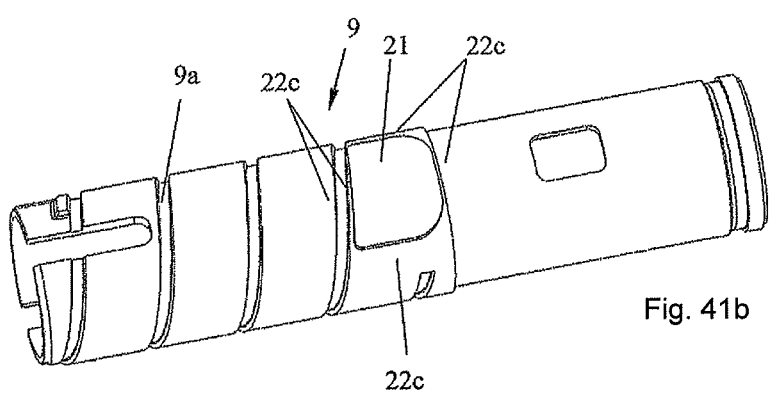
FIG. 41b shows a single part, i.e. a bearing element, for the device from FIGS. 38a-40b.

If the desired dose has been set (FIG. 31), the dose is discharged by pressing the actuating element 7 (FIGS. 32a, 32b). Actuating the actuating element 7 displaces the bearing element 9 together with the dose indicating element 10 along the longitudinal axis L. Because the body 20 is engaged with the external thread of the dose indicating element 10, it is carried along by the dose indicating element 10, i.e. it is likewise displaced along the longitudinal axis L relative to the housing 4 and/or the housing insert 4m when the actuating element 7 is actuated.

The advantage of a housing insert 4m is that the driving and dosing device is easier to assemble since it need not be initially ensured during assembly that the dose indicating element 10 is in threaded engagement with the internal thread portion of the body 20. The insert 4m can be inserted into the cutout of the housing 4 provided for it only after the device is nearly completely assembled, whereby the threaded portion is also brought into engagement with the external thread of the dose indicating element 10.

In the eleventh embodiment of the driving and dosing device, shown in FIGS. 34a-37b, the body 20 forming the pointing device 21 is a part separate from the bearing element 9 but at least axially fixedly connected to the bearing element 9, preferably also rotationally fixedly, in particular interlocked.

As can best be seen from FIGS. 37a and 37b, the body 20 is sleeve-shaped and surrounds the bearing element 9. The dose indicating element 10 is arranged between the bearing element 9 and the body 20. The sleeve-like portion of the body 20 is adjoined by a portion 23 extending in the distal direction, in particular an elongated portion, having an inward-directed protrusion 23a, more particularly a cam, which engages with a corresponding cutout 9i of the bearing element 9, in order to produce the axially fixed, preferably also rotationally fixed connection between the bearing element 9 and the body 20.

On its sleeve-shaped portion, the body 20 further comprises an outward-directed protrusion, particularly an annular protrusion 24, in which the pointing device 21 is formed in the shape of a window, wherein the flanks of the protrusion extending along the axis L are guided by the flanks of the window 4d of the housing 4, particularly the outer housing sleeve 4b. In general terms, the body 20 forming the pointing device 21 is connected to the housing 4 in such a manner that it is rotationally fixed thereto and axially displaceable in the longitudinal direction L. The body 20 has no threaded engagement with the dose indicating element 10, i.e. no threaded engagement between the dose indicating element 10 and the body 20 is necessary.

After the desired dose has been set by rotating the dosing element 3 out of the initial position (FIGS. 34a, 34b) relative to the housing 4 and the desired dose is displayed in the pointing device (FIG. 35), the actuating element 7 is actuated, i.e. pressed, whereby the clutch element 2 is displaced in the distal direction and drives the bearing element 9, which drives the body 20 and the dose indicating element 10.

The twelfth embodiment, shown in FIGS. 38a-41b, has a pointing device 21 that is formed by a body, more particularly the bearing element 9. The dose indicating element 10 is formed from a transparent material (FIG. 41 a), over the periphery of which and in the manner described herein, scale values 10*b* are applied along a helical track.

The symbols of the dose scale 10*b* form a symbol color, black for example.

Differently from the seventh through the eleventh embodiments, the pointing device 21 in the twelfth embodiment is not arranged between the window 4*d* of the housing 4 and the dose indicating element 10, but rather inside the dose indicating element 10. The dose indicating element 10 is arranged between the bearing element 9, more particularly the pointing device 21, and the window 4*d* or the outer housing sleeve 4*b*.

A region forming the pointing device 21 and having a first color is positioned behind the dose indicating element 10 in the region of the window 4*d* of the housing 4. In addition, a second region 22*c* adjoining the first region or the pointing device 21 distally and/or proximally is arranged behind the dose indicating element 10. The second region 22*c* has a second color. The contrast between the symbol color and the first color is greater than the contrast between the symbol color and the second color. For example the first color can be white and the second color black. Since the symbol color is likewise black in the example mentioned, the black digits are unrecognizable or barely recognizable (low contrast) against the black background, while the black digits are quite legible (high contrast) against the white background. The bearing element 9 can be formed from plastic, for example, which forms the first or second color while the other of the first and second colors is printed. Preferably the first color is printed.

The window of the outer housing sleeve 4*b* is dimensioned such that in every position of the actuating element 7, the first region 21 and the second region 22*c* are at least partially recognizable.

The first region 21 and the second region 22*c* are connected indirectly or directly to the bearing element 9 at least in such a mariner that they follow the movement of the bearing element 9 along the longitudinal axis L. In this case, the first region 21 and the second region 22*c* are formed by the bearing element 9. The bearing element 9 is secured against torsion (e.g., rotation) and is connected axially displaceably to the housing 4. The bearing element 9 is additionally connected rotatably and axially fixedly to the clutch element 2. The clutch element 2 is connected axially displaceably and rotationally fixedly to the dose indicating element 10. There is a threaded engagement between the dose indicating element 10 and the bearing element 9.

What is claimed is:

1. A driving and dosing device configured to set a dose to be administered from an injection device for administering a liquid product, the driving and dosing device comprising:
   a) a housing;
   b) a pointing device;
   c) a dosing element configured to be gripped by a user and to be rotated relative to the pointing device about an axis of rotation for setting the dose to be administered;
   d) a dose indicating element comprising a dose scale arranged over an exterior of the dose indicating element; and
   e) a bearing element in an engagement with the dose indicating element,
      wherein by rotating the dosing element relative to the pointing device to set the dose, the dose indicating element is rotated or screwed relative to the pointing device about the axis of rotation such that a value of the dose scale corresponding to a set dose can be read by means of the pointing device,
      wherein the engagement of the bearing element with the dose indicating element guides a rotational movement or a screwing movement of the dose indicating element relative to the pointing device,
      wherein the bearing element is arranged rotationally fixed relative to the housing but displaceable relative to the housing and along the axis of rotation, and
      wherein the dose indicating element is displaceable relative to the housing and along the axis of rotation and lacks a threaded engagement with the housing.

2. The driving and dosing device of claim 1, wherein the bearing element and the dose indicating element are movable relative to the pointing device and wherein the bearing element is in thread engagement with the dose indicating element.

3. The driving and dosing device of claim 2, wherein displacement of the bearing element along the axis of rotation causes a marking arranged on the dose indicating element to appear in a region of the pointing device, wherein the marking is different from the dose scale.

4. The driving and dosing device of claim 1, further comprising an actuating element, the actuation of which: 1) causes the bearing element, together with the dose indicating element and the pointing device, to be displaced relative to the housing and along the axis of rotation and/or 2) causes a propulsion element, for acting on a piston of a product container, to be displaced in the distal direction.

5. The driving and dosing device of claim 1, further comprising an actuating element, the actuation of which causes the dose indicating element to be rotated or screwed relative to the bearing element such that values of the dose scale moving past the pointing device count down.

6. The driving and dosing device of claim 1, wherein the driving and dosing device is configured such that energy necessary for rotating the dose indicating element back and/or displacing a propulsion element in the distal direction is exerted automatically by a spring and whereby the dosing element is connected axially fixedly to the housing.

7. A driving and dosing device configured to set a dose to be administered from an injection device for administering a liquid product, the driving and dosing device comprising:
   a) a housing;
   b) a pointing device;
   c) a dosing element configured to be gripped by a user and to be rotated relative to the pointing device about an axis of rotation for setting the dose to be administered, wherein a body of the pointing device is movable relative to the housing and along the axis of rotation;
   d) a dose indicating element comprising a dose scale arranged over an exterior of the dose indicating element; and
   e) a bearing element in an engagement with the dose indicating element,
      wherein by rotating the dosing element relative to the pointing device to set the dose, the dose indicating element is rotated or screwed relative to the pointing device about the axis of rotation such that a value of the dose scale corresponding to a set dose can be read by means of the pointing device,
      wherein the engagement of the bearing element with the dose indicating element guides a rotational movement or a screwing movement of the dose indicating element relative to the pointing device,
      wherein the bearing element is arranged rotationally fixed relative to the housing but displaceable relative to the housing and along the axis of rotation, and wherein the dose indicating element is displaceable relative to the housing and along the axis of rotation.

8. The driving and dosing device of claim 7, wherein displacement of the bearing element along the axis of rotation causes a marking arranged on the dose indicating element or on the body of the pointing device to appear in a region of the pointing device, wherein the marking is different from the dose scale.

9. The driving and dosing device of claim 7, wherein the housing comprises a window that enables the pointing device to be viewed from an exterior of the housing.

10. The driving and dosing device of claim 9, wherein the pointing device is arranged at least one of: between the window of the housing and the dose indicating element or the body of the pointing device is arranged between the dose indicating element and the housing.

11. The driving and dosing device of claim 9, wherein the pointing device is configured such that it enables the dose indicating element to be viewed through the pointing device.

12. The driving and dosing device of claim 9, further comprising opaque regions adjoining the body of the pointing device, wherein the pointing device is arranged between the opaque regions.

13. The driving and dosing device of claim 12, wherein the body of the pointing device comprises an opaque material defining at least a portion of the opaque regions, and the pointing device comprises a cutout defined in the body or is a window of transparent material.

14. The driving and dosing device of claim 12, wherein the body of the pointing device comprises a transparent material, and the opaque regions adjoining the pointing device are at least one of: an imprint, a coating or a processed region of the transparent material that has made the transparent material opaque.

15. The driving and dosing device of claim 9, wherein the housing or a housing insert defining the window of the housing comprises a guide configured to displaceably guide the body of the pointing device, wherein the body of the pointing device is mounted axially fixedly and rotatably on a clutch element, and wherein the clutch element is connected secured against rotation and axially displaceable relative to the dose indicating element.

16. The driving and dosing device of claim 9, wherein the housing or a housing insert defining the window of the housing comprises a guide that displaceably guides the body of the pointing device, wherein the body of the pointing device and the bearing element are separate, secured against rotation along the longitudinal axis, wherein the dose indicating element comprises an external thread configured to engage with the body of the pointing device and an internal thread configured to engage with the bearing element, wherein the external thread and the internal thread of the dose indicating element have a thread pitch that is the same.

17. The driving and dosing device of claim 9, wherein the housing or a housing insert defining the window of the housing comprises a guide that displaceably guides the body of the pointing device, wherein the body of the pointing device and the bearing element are separate, and wherein the body of the pointing device is joined axially fixedly and non-rotatably to the bearing element.

18. The driving and dosing device of claim 9, wherein the dose indicating element comprises a transparent material and symbols of the dose scale of the dose indicating element include a symbol color, wherein at the window of the housing, a first region of the pointing device includes a first color and a second region of the pointing device includes a second color and the first and second regions are positioned behind the dose indicating element, wherein the first region is positioned behind one part of the dose scale and the second region is positioned behind another part of the dose scale, and wherein a contrast between the symbol color of the dose scale and the first color of the pointing device is relatively stronger than a contrast between the symbol color of the dose scale and the second color of the pointing device.

19. The driving and dosing device of claim 18, wherein the first region and the second region of the pointing device are joined indirectly or directly to the bearing element such that the first and second regions are slaved in movement of the bearing element along the longitudinal axis.

20. The driving and dosing device of claim 7, wherein the dose indicating element and the body of the pointing device interpenetrate one another by a threaded connection, wherein the body of the pointing device is indirectly or directly connected to the bearing element such that the body follows a movement of the bearing element along the longitudinal axis.

21. The driving and dosing device of claim 7, further comprising an actuating element, the actuation of which causes the bearing element, together with the dose indicating element and the pointing device, to be displaced relative to the housing and along the axis of rotation.

22. A driving and dosing device configured to set a dose to be administered from an injection device for administering a liquid product, the driving and dosing device comprising:
   a) a housing;
   b) a pointing device;
   c) a dosing element configured to be gripped by a user and to be rotated relative to the pointing device about an axis of rotation for setting the dose to be administered;
   d) a dose indicating element comprising a dose scale arranged over an exterior of the dose indicating element; and
   e) a bearing element in an engagement with the dose indicating element,
      wherein by rotating the dosing element relative to the pointing device to set the dose, the dose indicating element is rotated or screwed relative to the pointing device about the axis of rotation such that a value of the dose scale corresponding to a set dose can be read by means of the pointing device,
      wherein the engagement of the bearing element with the dose indicating element guides a rotational movement or a screwing movement of the dose indicating element relative to the pointing device,
      wherein the bearing element is arranged rotationally fixed relative to the housing but displaceable relative to the housing and along the axis of rotation,
      wherein the dose indicating element is displaceable relative to the housing and along the axis of rotation, and
      wherein the driving and dosing device is configured such that energy necessary for rotating the dose indicating element back and/or displacing a propulsion element in the distal direction is exerted automatically by a spring and whereby the dosing element is connected axially fixedly to the housing.

23. The driving and dosing device of claim 22, wherein the bearing element and the dose indicating element are movable relative to the pointing device.

24. The driving and dosing device of claim 23, wherein displacement of the bearing element along the axis of rotation causes a marking arranged on the dose indicating element to appear in a region of the pointing device, wherein the marking is different from the dose scale.

25. The driving and dosing device of claim 22, further comprising an actuating element, the actuation of which: 1) causes the bearing element, together with the dose indicating element and the pointing device, to be displaced relative to the housing and along the axis of rotation and/or 2) causes a propulsion element, for acting on a piston of a product container, to be displaced in the distal direction.

26. The driving and dosing device of claim 22, further comprising an actuating element, the actuation of which causes the dose indicating element to be rotated or screwed relative to the bearing element such that values of the dose scale moving past the pointing device count down.

* * * * *